(12) United States Patent
Zhou et al.

(10) Patent No.: US 7,923,437 B2
(45) Date of Patent: *Apr. 12, 2011

(54) WATER SOLUBLE β-GLUCAN, GLUCOSAMINE, AND N-ACETYLGLUCOSAMINE COMPOSITIONS AND METHODS FOR MAKING THE SAME

(75) Inventors: Shuang Zhou, Oskaloosa, IA (US); Tzyy-Jan Han, Pella, IA (US); Lawrence E. Fosdick, Oskaloosa, IA (US); Jess Vasina, Pella, IA (US)

(73) Assignee: Cargill, Incorporated, Wayzata, MN (US)

( * ) Notice: Subject to any disclaimer, the term of this patent is extended or adjusted under 35 U.S.C. 154(b) by 1230 days.

This patent is subject to a terminal disclaimer.

(21) Appl. No.: 11/394,981

(22) Filed: Mar. 31, 2006

(65) Prior Publication Data
US 2006/0172392 A1 Aug. 3, 2006

Related U.S. Application Data

(63) Continuation-in-part of application No. 10/685,125, filed on Oct. 13, 2003, which is a continuation-in-part of application No. 10/326,549, filed on Dec. 19, 2002, now Pat. No. 7,049,433, which is a continuation of application No. 09/785,695, filed on Feb. 16, 2001, now abandoned, application No. 11/394,981, which is a continuation-in-part of application No. PCT/US03/34846, filed on Oct. 31, 2003, application No. 11/394,981, which is a continuation-in-part of application No. PCT/US02/25121, filed on Aug. 7, 2002.

(60) Provisional application No. 60/423,119, filed on Nov. 1, 2002.

(51) Int. Cl.
*A01N 43/04* (2006.01)
*A61K 31/715* (2006.01)
*A61K 31/70* (2006.01)

(52) U.S. Cl. .............................. 514/54; 514/62; 435/171

(58) Field of Classification Search .................... 514/54, 514/62; 435/171
See application file for complete search history.

(56) References Cited

U.S. PATENT DOCUMENTS

| | | |
|---|---|---|
| 2,040,879 A | 5/1936 | Rigby |
| 3,232,836 A | 2/1966 | Carlozzi et al. |
| 3,632,754 A | 1/1972 | Balassa |
| 3,683,076 A | 8/1972 | Rovati |
| 3,903,268 A | 9/1975 | Balassa |
| 3,911,116 A | 10/1975 | Balassa |
| 3,914,413 A | 10/1975 | Balassa |
| 4,034,121 A | 7/1977 | Dunn et al. |
| 4,056,432 A | 11/1977 | Slagel et al. |
| 4,211,846 A | 7/1980 | Lafferty |
| 4,282,351 A | 8/1981 | Muzzarelli |
| 4,642,340 A | 2/1987 | Senin et al. |
| 4,806,474 A | 2/1989 | Hershberger |
| 4,810,646 A | 3/1989 | Jamas et al. |
| 4,886,541 A | 12/1989 | Hadwiger |
| 4,948,881 A | 8/1990 | Naggi et al. |
| 4,954,440 A * | 9/1990 | Johal et al. ..................... 435/101 |
| 4,970,150 A | 11/1990 | Yaku et al. |
| 4,983,304 A | 1/1991 | Tsugita et al. |
| 5,141,964 A | 8/1992 | Noel |
| 5,219,749 A | 6/1993 | Bouriotis et al. |
| 5,232,842 A | 8/1993 | Park et al. |
| 5,262,310 A | 11/1993 | Karube et al. |
| 5,401,727 A | 3/1995 | Rorstad et al. |
| 5,488,040 A * | 1/1996 | Jamas et al. .................... 514/54 |
| 5,532,223 A | 7/1996 | Jamas et al. |
| 5,622,939 A | 4/1997 | Jamas et al. |
| 5,663,324 A | 9/1997 | Jamas et al. |
| 5,702,939 A | 12/1997 | Fujishima et al. |
| 5,730,876 A | 3/1998 | You et al. |
| 5,783,569 A | 7/1998 | Jamas et al. |
| 5,811,542 A | 9/1998 | Jamas et al. |
| 5,814,341 A | 9/1998 | Fankhauser et al. |
| 5,817,643 A | 10/1998 | Jamas et al. |
| 5,843,923 A | 12/1998 | Schleck et al. |
| 5,859,263 A | 1/1999 | Ghorpade et al. |
| 5,902,801 A | 5/1999 | Schleck et al. |
| 5,905,035 A | 5/1999 | Okada et al. |
| 5,985,644 A | 11/1999 | Roseman et al. |
| 5,998,173 A | 12/1999 | Haynes et al. |
| 6,060,429 A | 5/2000 | Ben-Shalom et al. |
| 6,117,851 A | 9/2000 | Sherman et al. |
| 6,143,883 A | 11/2000 | Lehmann et al. |
| 6,225,493 B1 | 5/2001 | Prakash et al. |
| 6,242,594 B1 | 6/2001 | Kelly |
| 6,248,570 B1 | 6/2001 | Michon et al. |

(Continued)

FOREIGN PATENT DOCUMENTS

CN 1496408 5/2004

(Continued)

OTHER PUBLICATIONS

Ruiz-Herrera, Antonie van Leeuwenhoek, 1991, Kluwer Academic Publishers, vol. 60, pp. 73-81.*
Houssain et. al., Applied Microbiol. Biotechnol., 1984, Springer-Verlag, pp. 393-397.*
Aldrich, Catalog Hand book of Fine Chemicals, p. 756 (1996).
Alonso, I. et al., "Determination of the Degree of Acetylation of Chitin and Chitosan by Thermal Analysis," *Journal of Thermal Analysis*, vol. 28, pp. 189-193 (1983).
Arcidiacono, S. et al., "Molecular Weight Distribution of Chitosan isolated from *Mucor rouxii* under Different Culture and Processing Conditions," *Biotechnology and Bioengineering*, vol. 39, pp. 281-286 (1992).

(Continued)

*Primary Examiner* — Sreeni Padmanabhan
*Assistant Examiner* — Sarah Pihonak
(74) *Attorney, Agent, or Firm* — Klarquist Sparkman, LLP

(57) ABSTRACT

Glucosamine, N-acetylglucosamine and β-glucan compositions suitable for human or animal consumption or use are disclosed. The glucosamine, N-acetylglucosamine and β-glucan compositions are derived from fungal biomass containing chitin. Various methods of producing glucosamine, N-Acetylglucosamine and β-glucan compositions are also disclosed.

28 Claims, 13 Drawing Sheets

U.S. PATENT DOCUMENTS

| | | | |
|---|---|---|---|
| 6,284,885 B1 | 9/2001 | Tamura et al. | |
| 6,333,399 B1* | 12/2001 | Teslenko et al. | 536/20 |
| 6,369,216 B1 | 4/2002 | Patchen et al. | |
| 6,372,457 B1 | 4/2002 | Berry et al. | |
| 6,432,929 B1 | 8/2002 | Stone | |
| 6,444,448 B1 | 9/2002 | Wheatcroft et al. | |
| 6,486,307 B1 | 11/2002 | Gandhi et al. | |
| 6,495,531 B2 | 12/2002 | Vanden Berghe | |
| 6,512,166 B1 | 1/2003 | Harman et al. | |
| 6,548,075 B1 | 4/2003 | Bengs et al. | |
| 6,693,188 B2 | 2/2004 | Bohlmann et al. | |
| H2218 H | 6/2005 | Hwang et al. | |
| 6,939,864 B1 | 9/2005 | Johnson et al. | |
| 7,049,433 B2 | 5/2006 | Fan et al. | |
| 2002/0115639 A1 | 8/2002 | Fan et al. | |
| 2002/0160459 A1 | 10/2002 | Berry et al. | |
| 2003/0134825 A1 | 7/2003 | Bahoshy | |
| 2003/0138543 A1 | 7/2003 | Bahoshy | |
| 2003/0170374 A1 | 9/2003 | Bahoshy | |
| 2003/0181419 A1 | 9/2003 | Hwang et al. | |
| 2004/0077055 A1 | 4/2004 | Fosdick et al. | |
| 2005/0065114 A1 | 3/2005 | Yvin et al. | |
| 2005/0095686 A1 | 5/2005 | Federici et al. | |
| 2005/0130273 A1 | 6/2005 | Versali et al. | |
| 2006/0178344 A1 | 8/2006 | Anderson et al. | |

FOREIGN PATENT DOCUMENTS

| | | |
|---|---|---|
| CN | 1796395 | 7/2006 |
| EP | 566 349 | 10/1993 |
| EP | 768 320 | 4/1997 |
| EP | 0 885 954 A1 | 12/1998 |
| EP | 997 480 | 5/2000 |
| GB | 458839 | 12/1936 |
| GB | 785525 | 10/1957 |
| GB | 833264 | 4/1960 |
| GB | 896940 | 5/1962 |
| GB | 2101585 | 1/1983 |
| GB | 2 372 509 | 8/2002 |
| JP | 55012109 | 1/1980 |
| JP | 62070401 A2 | 3/1987 |
| JP | 63097633 A2 | 4/1988 |
| JP | 63225602 A2 | 9/1988 |
| JP | 2149335 A2 | 6/1990 |
| JP | 2180903 A2 | 7/1990 |
| JP | 2200196 A2 | 8/1990 |
| JP | 2229832 A2 | 9/1990 |
| JP | 2258740 A2 | 10/1990 |
| JP | 5068580 A2 | 10/1993 |
| JP | 7330808 A2 | 12/1995 |
| JP | 8-41106 A | 2/1996 |
| JP | 10297913 A2 | 11/1998 |
| JP | 2000281696 | 10/2000 |
| JP | 2001-292792 | 10/2001 |
| WO | WO 98/30713 | 7/1998 |
| WO | WO 98/42755 | 10/1998 |
| WO | WO 99/41294 | 8/1999 |
| WO | WO 00/04182 | 1/2000 |
| WO | WO 01/01992 A1 | 1/2001 |
| WO | WO 01/93847 | 12/2001 |
| WO | WO 02/066667 | 8/2002 |
| WO | WO 03/013435 | 2/2003 |
| WO | WO 2004/041199 | 5/2004 |

OTHER PUBLICATIONS

Atrih, A. et al., "Analysis of Peptidoglycan Structure from Vegetative Cells of *Bacillus subtilis* 168 and Role of PBP 5 in Peptidoglycan Maturation," *Journal of Bacteriology*, vol. 181, No. 13, pp. 3956-3966 (Jul. 1999).

Bartnicki-Garcia, S., "Cell Wall Chemistry, Morphogenesis, and Taxonomy of Fungi," *Chemistry of Fungal Cell Wall*, pp. 87-108 (1968).

Benjakul, S. et al., "Improvement of Deacetylation of Chitin from Black Tiger Shrimp (*Penaeus monodon*) Carapace and Shell," *ASEAN Food Journal*, vol. 9, No. 4, pp. 136-140 (1994).

Beri, R., et al., "Characterization of Chitosans via Coupled Size-Exclusion Chromatography and Multiple-Angle Laser Light-Scattering Technique," *Carbohydrate Research*, vol. 238, pp. 11-26 (1993).

Biermann, C., "Hydrolysis and Other Cleavage of Glycosidic Linkages," Chapter 3, pp. 29-41 (Date Unknown).

Carlson, T. et al., "Chitin/Chitosan Extraction from *A. niger* Mycelium," *Cargill Central Research*, 16 pages (Aug. 1997).

"Chitin/Chitosan Specifications," *Biopolymer Engineering, Inc.*, http://www.biopolymer.com/spec.htm, 1 page (Date printed Mar. 4, 1999).

Davies, D., et al., "Determination of the Degree of Acetylation of Chitin and Chitosan," *Methods in Enzymology*, vol. 161, Part B, pp. 442-446 (1988).

Deal, C. et al., "Nutraceuticals as Therapeutic Agents in Osteoarthritis. The Role of Glucosamine, Chondroitin Sulfate, and Collagen Hydrolysate," *Osteoarthritis*, vol. 25, No. 2, pp. 379-395 (May 1999).

Domanski et al., "Use of a Chitinase Complex and β-(1,3)-Glucanase for Spheroplast Production from *Candida albicans*," *J. Bacteriol.*, vol. 96, pp. 270-271 (1968).

Domszy, J. et al., "Evaluation of Infrared Spectroscopic Techniques for Analyzing Chitosan," *Makromal. Chem.*, vol. 186, pp. 1671-1677 (1985).

Eichner, "Antioxidative Effect of Maillard Reaction Intermediates," *Prog. Fd. Nutr. Sci.*, vol. 5, pp. 441-451 (1981).

Farkas, V., "Fungal Cell Walls: Their Structure, Biosynthesis and Biotechnological Aspects," *Acta Biotechnol.*, vol. 10, No. 3, pp. 225-238 (1990).

Ferrer, J., "Acid Hydrolysis of Shrimp-Shell Wastes and the Production of Single Cell Protein from the Hydrolysate," *Bioresourcc Technology*, vol. 57, pp. 55-60 (1996).

Fleet, G. et al., "17 Fungal Glucans—Structure and Metabolism," *Encyclopedia of Plant Physiology*, vol. 13B, New Series, pp. 416-440 (1981).

Freimund, S. et al., A New Non-Degrading Isolation Process for 1,3-β-D-Glucan of High Purity from Baker's Yeast *Saccharomyces cerevisiae*, *Carbohydrate Polymers*, vol. 54, pp. 159-171 (2003).

"The Fungal Cell," Chapter 2, pp. 22-39 (Date Unknown).

Gassner, G. et al., "Teichuronic Acid Reducing Terminal *N*-Acetylglucosamine Residue Linked by Phosphodiester to Peptidoglycan of *Micrococcus luteus*," *J. Bacteriol.*, vol. 172, No. 5. pp. 2273-2279 (May 1990).

Ghorpade et al., "Industrial Applications for Levulinic Acid," Industrial Agricultural Product Center, University of Nebraska (visited Oct. 8, 2003) http://agproducts.unl.edu/levu.htm, 8 pages.

"Glucosamine Hydrochloride," *Pharmacopeial Forum*, vol. 26, No. 5, pp. 1449-1450 (Sep.-Oct. 2000).

Gobin, P. et al., "Structural Chemistry of Fungal Polysaccharides," pp. 367-417 (1968).

Gomyo et al., "On the Interaction of Melanoidin with Metallic Ions," *Agr. Biol. Chem.*, vol. 40, No. 1, pp. 33-40 (1976).

Hayase et al., "Scavenging of Active Oxygens by Melanoidins," *Agr. Biol. Chem.*, vol. 53, No. 12, pp. 3383-3385 (1989).

Huang et al., "Development and Validation of Oxygen Radical Absorbance Capacity Assay for Lipophilic Antioxidants Using Randomly Methylated β-Cyclodextrin as the Solubility Enhancer," *J. Agric. Food Chem.*, 7 pp. (2002).

Huang et al., "High-Throughput Assay of Oxygen Radical Absorbance Capacity (ORAC) Using a Multichannel Liquid Handling System Coupled with a Microplate Fluorescence Reader in 96-Well Format," *J. Agric. Food. Chem.*, vol. 50, pp. 4437-4444 (2002).

Jacobson, R., "Berichte der Deutschen Chemischen Gesellschaft," pp. 2192-2200 (1898) (German).

Johnston, I., "The Composition of the Cell Wall of *Asperigillus niger*," *Biochem. J.*, vol. 96, pp. 651-658 (1965).

Kimura, K. et al, "Determination of the Mode of Hydrolysis of Chitooligosaccharides by Chitosanase Derived from *Aspergillus oryzae* by Thin Layer Chromatography," *Chemistry Letters*, pp. 223-226 (1992).

Kostina et al., "Chitin of mycelial fungi of the Penicillium genus," Prikl. Biokhim. Mikrobiol. Abstract, vol. 14, No. 4, pp. 586-593 (1978).

Kurita, K., "Controlled Functionalization of the Polysaccharide Chitin," *Prog. Polym. Sci.*, vol. 26, pp. 1921-1971 (2001).

Kurita, K. et al., "Studies on Chitin, 3, Preparation of Pure Chitin, Poly(N-acetyl-D-glucosamine), from the Water-Soluble Chitin," *Makromol. Chem.*, vol. 178, pp. 2595-2602 (1977).

Kurita, K. et al., "Studies on Chitin, 4, Evidence for Formation of Block and Random Copolymers of N-Acetyl-D-glucosamine and D-Glucosamine by Hetero- and Homogeneous Hydrolyses," *Makromol. Chem.*, vol. 178, pp. 3197-3202 (1977).

Maghami, G. et al., "Evaluation of the Viscometric Constants for Chitosan," *Makromol. Chem.*, vol. 189, pp. 195-200 (1988).

Maitre, N. et al., "Primary T-Cell and Activated Macrophage Response Associated with Tumor Protection Using Peptide/Poly-N-Acetyl Glucosamine Vaccination," *Clinical Cancer Research*, vol. 5, pp. 1173-1182 (May 1999).

Methacanon, P. et al., "Structural Elucidation of Bioactive Fungi-Derived Polymers," *Carbohydrate Polymers*, vol. 60, pp. 199-203 (2005).

Mima, S. et al., "Highly Deacetylated Chitosan and Its Properties," *Journal of Applied Polymer Sciences*, vol. 28, pp. 1909-1917 (1983).

Muzzarelli, R. et al., "Chelating, Film-Forming, and Coagulating Ability of the Citosan-Glucan Complex from *Aspergillus niger* Industrial Wastes," *Biotechnology and Bioengineering*, vol. XXII, pp. 885-896 (1980).

Nanjo, F. et al., "Purification, Properties, and Transglycosylation Reaction of β-N-Acetylhexosaminidase from *Nocardia orientalis*," *Agric. Biol. Chem.*, vol. 54, No. 4, pp. 899-906 (1990).

Nanjo, F. et al., "Purification and Characterization of an Exo-β-D-glucosaminidase, a Novel Type of Enzyme, from *Nocardia orientalis*," *The Journal of Biological Chemistry*, vol. 265, No. 17, pp. 10088-10094 (Jun. 15, 1990).

Nanjo, F. et al., "Enzymatic Method for Determination of the Degree of Deacetylation of Chitosan," *Analytical Biochemistry*, vol. 193, pp. 164-167 (1991).

Nguyen, T. et al., "Composition of the Cell Walls of Several Yeast Species," *Abstract*, vol. 50, No. 2, pp. 206-212 (1998).

Nikolaeva et al., CAPLUS Abstract, AN 1968:62461 (1968).

Nikolaeva et al., "Preparation of glucosamine from shrimp shells, and its use in medicine," Tr. Vses. Nauchno Issled. Inst. Morsk. Rybn. Khoz Okeanogr., pp. 165-169 (1967) (Abstract).

Nilsson et al., "Chitin as an indicator of the biomass of two wood-decay fungi in relation to temperature, incubation time, and media composition," Abstract, *Canadian Journal of Microbiology*, vol. 44, No. 6, pp. 575-581 (1998).

Niola, F. et al., "A Rapid Method for the Determination of the Degree of N-acetylation of chitin-chitosan samples by acid hydrolysis and HPLC," *Carbohydrate Research*, vol. 238, pp. 1-9 (1993).

No, H. et al. "Preparation and Characterization of Chitin and Chitosan—A Review," *Journal of Aquatic Food Product Technology*, vol. 4, No. 2, pp. 27-51 (1995).

Nogawa, M. et al., "Purification and Characterization of Exo-β-D-Glucosaminidase from a Cellulolytic Fungas, *Trichoderma reesei* PC-3-7," *Appl. Environ. Microbiol.*, vol. 64, No. 3, pp. 890-895 (Mar. 1998).

Novikov, V. et al., "Synthesis of D(+)-Glucosamine Hydrochloride," *Russian Journal of Applied Chemistry*, vol. 70, No. 9, pp. 1467-1470 (1997).

Novikov, "Kinetics of formation of D-(+)-glucosamine in acid hydrolysis of chitin," *Russian Journal Abstract* (Sankt-Peterburg), vol. 72, No. 1, pp. 147-152 (1999).

Ottoy, M. et al., "Preparative and Analytical Size-exclusion Chromatography of Chitosans," *Carbohydrate Polymers*, vol. 31, pp. 253-261 (1996).

Ou et al., "Analysis of Antioxidant Activities of Common Vegetables Employing Oxygen Radical Absorbance Capacity (ORAC) and Ferric Reducing Antioxidant Power (FRAP) Assays: A Comparative Study," *J. Agric. Food Chem.*, 7 pages (2002).

Pelletier, A. et al., "Chitin/Chitosan Tranformation by Thermo-Mechano-Chemical Treatment Including Characterization by Enzymatic Depolymerization," *Biotechnology and Bioengineering*, vol. 36, pp. 310-315 (1990).

Plassard et al., "Estimation of mycelial growth of basidiomycetes by means of chitin determination," Abstract, *Phytochemistry* (Oxford), vol. 21, No. 2, pp. 345-349 (1982).

Rege, P. et al. "Chitosan Processing: Influence of Process Parameters During Acidic and Alkaline Hydrolysis and Effect of the Processing Sequence on the Resultant Chitosan's Properties," *Carbohydrate Research*, vol. 321, Nos. 3-4, pp. 235-245 (Oct. 15, 1999).

Roberts, G. et al., "Determination of the Viscomtric Constants for Chitosan," *Int. J. Biol.*, vol. 4, pp. 374-377 (Oct. 1982).

Rokem, J. et al., "Degradation of Fungal Cell Walls Taking into Consideration the Polysaccharide Composition," *Enzyme Microb. Technol.*, vol. 8, No. 10, pp. 588-592 (Oct. 1986) (Abstract).

Ruiz-Herrera, J., "Chemical Components of the Cell Wall of *Aspergillus species*," *Archives of Biochemistry and Biophysics*, vol. 122, pp. 118-125 (1967).

Sabnis, S. et al., "Improved Infrared Spectroscopic Method for the Analysis of Degree of N-deacetylation of Chitosan," *Polymer Bulletin*, vol. 39, pp. 67-71 (1997).

Sakai, K. et al., "Purification and Hydrolytic Action of a Chitosanase from *Nocardia orientalis*," *Biochimica et Biophysica Acta.*, vol. 1079, pp. 65-72 (1991).

Sannan, T. et al., "Studies on Chitin, 2, Effect of Deacetylation on Solubility," *Makromol. Chem.*, vol. 177. pp. 3589-3600 (1976).

Shahidi, F. et al., "Food Applications of Chitin and Chitosans," *Trends in Food Science & Technology*, vol. 10, pp. 37-51 (1999).

Shu, C-K, "Degradation Products Formed from Glucosamine in Water," *J. Agric. Food Chem.*, vol. 46, pp. 1129-1131 (1998).

Sigma, Biochemicals and Reagents, p. 461 (2000).

Stagg, C. et al., The Characterization of a Chitin-Associated D-Glucan from the Cell Walls of *Aspergillus niger*, vol. 320, pp. 64-72 (1973).

Stainer, R. et al., "The Microbial World," *Prentice-Hall, Inc.*, pp. 332-336 (1970).

Tan, S. et al., "The Degree of Deacetylation of Chitosan: Advocating the First Derivative UV-spectrophotometry Method of Determination," *Talanta*, vol. 45, pp. 713-719 (1998).

Wessels, J. et al., "15 Fungal Cell Walls: A Survey," *Plant Carbohydrates II, Extracellular Carbohydrates*, pp. 352-394 (1981).

Wu, A. et al., "Determination of Molecular-Weight Distribution of Chitosan by High-performance Liquid Chromatography," *Journal of Chromatography*, vol. 128, pp. 87-99 (1976).

Xin et al., "Primary study on the production of chitosan by the method of culturing microorganism," Food Science, p. 22 (3 pp.) (and a partial English translation) (Jul. 1997).

Yang et al., "Acidic hydrolysis and determination of fungal mycelium in cereals," Chinese Journal Abstract, *Chinese Agricultural Chemical Society*, vol. 36, No. 6, pp. 555-564 (1998).

Yen et al., "Antioxidant and Prooxidant Activity of Xylose-Lysine Maillard Reaction Products," *The Maillard Reaction in Foods and Medicine*, Ed. J. O'Brien et al., pp. 231-236 (1998).

Yen et al., "Antioxidative Activity and Scavenging Effects on Active Oxygen of Xylose-Lysine Maillard Reaction Products," *J. Sci. Food Agric.*, vol. 67, pp. 415-420 (1995).

Cargill Acidulants, "Proposal for making a "Substantial Equivalence" notification for Non-Shellfish Glucosamine Hydrochloride under Regulation (EC) No. 258/97 for the European Parliament and the Council of 27 Jan. 1997 concerning novel foods and novel food ingredients," (Feb. 5, 2004).

Cargill, Incorporated, "Gras Notification for Regenasure™ Glucosamine Hydrochloride," (Apr. 6, 2004).

Glucosamine product label from Twinlab Flexi-licious (with shellfish allergy warning).

Glucosamine product label from HyVee HealthMarket (with shellfish allergy warning).

Glucosamine product label from Osteo Bi-flex (2 pages) (with shellfish allergy warning), (2000).

Database Caplus on STN: Accession No. 1976-519336 (1976).

Database Caplus on STN: Accession No. 1999:816485 (1999).

Department of Health and Human Services, *FDA Increases Sampling of Imported Shrimp and Crayfish*, FDA News (2002) (available at www.fda.gov.bbs.topics/NEWS/2002/NEW00815.html, last visited Oct. 18, 2002).

Federal Trade Commission, *Shark Cartilage Receives 10M Draft Monograph*, FTC Notice (2002) (available at www.ftc.gov/opa/2002/09/fdacomments.htm, as of Sep. 2002).

"Glycoprotein Monosaccharide Analysis Using High-Performance Anion-Exchange Chromatography with Pulsed Amperometric Detection (HPAE-PAD)," Dionex, Technical Note 40, 6 pages. (1998).

Jeremy Appleton, *Inadequate Screening of Imported Food and Dietary Supplements*, 2 Integrative Medicine, 58-65 (available at www.ifr.bbsrc.ac.uk/protall/infosheet.htm, Feb./Mar. 2003).

Xianchang Gong, *Heavy Metal Contaminates in the Glucosamine Product* (a paper regarding a crab shell glucosamine product) (date unknown).

Office action dated Mar. 29, 2006 for U.S. Appl. No. 10/382,251, filed Mar. 5, 2003.

English Translation of JP2000281696, published Oct. 10, 2000.

International Search Report and Written Opinion for PCT/US2007/007365, filed Mar. 22, 2007 (Mailed Oct. 22, 2007).

International Search Report and Written Opinion for PCT/US2007/007258, filed Mar. 22, 2007 (Mailed Aug. 29, 2007).

Matsubara, Machiko et al., "Physiological and Biochemical Studies on Germinating Fungal Spores. VII. Chemical Composition of Cell Walls in Conidia of *Cochliobolus miyabeanus*," Chem. Pharm. Bull., vol. 33, No. 3, pp. 1175-1180 (1985).

White, Stephen A. et al., "Production and Isolation of Chitosan from *Mucor rouxii*," Applied and Environmental Microbiology, vol. 38, No. 2, pp. 323-328 (Aug. 1979).

Cao, G., "Preparation of Glucosamine Hydrochloride from Chitin," Journal: Huaxue Shijie, vol. 39, No. 5, pp. 250-253 (1998).

Ekbald, A. et al., "Determination of chitin in fungi and mycorrhizal roots by an improved HPLC analysis of glucosamine," Plant and Soil, vol. 178, pp. 29-35 (1996).

Hicks, R.E. et al., "A comparison of glucosamine and biovolume conversion factors for estimating fungal biomass," Oikos, vol. 42, pp. 355-360 (1984).

Novikov, V. Yu., "Kinetics of Formation of D(+)-Glucosamine by Acid Hydrolysis of Chitin," Russian Journal of Applied Chemistry, vol. 72, No. 1, pp. 156-161 (1999).

Office Action from the Canadian Intellectual Property Office for Canadian Patent Application No. 2,438,233, dated Apr. 7, 2009.

Ride, J.P. et al., "A rapid method for the chemical estimation of filamentous fungi in plant tissue," Physiol. Plant Pathol, vol. 2, pp. 7-15 (1972).

Schmitz, O. et al., "Quantification of vesicular-arbuscular mycorrhiza by biochemical parameters," J. Plant Physiol, vol. 139, pp. 106-114 (1991).

Wu, T. et al., "Chitin and Chitosan—Value-Added Products from Mushroom Waste," J. Agric. Food Chem., vol. 52, No. 26, pp. 7905-7910 (Dec. 12, 2004).

Bangliang, Li et al., "The Preparation and Analysis of Low-molecular Weight Chitosan," Chinese Journal of Biochemical Pharmaceutics, vol. 20, No. 6, pp. 292-294 (1999) (English translated title and abstract).

Cai, Jingping et al., "Study on Production of Amino Chitosan Oligosaccharide," Food Science, vol. 21, No. 9 pp. 21-24 (2000) (English translated title and abstract).

Chang, Ke Liang B. et al., "HPLC Analysis of N-acetyl-chitooligosaccharides during the Acid Hydrolysis of Chitin," Journal of Food and Drug Analysis, vol. 8, No. 2, pp. 75-83 (2000).

Falk, Michael et al., "Studies on Chitan ($\beta$-(1$\rightarrow$4),-Linked 2-Acetamido-2-Deoxy-D-Glucan) Fibers of the Diatom Thalassiosira Fluviatilis Hustedt" Canadian Journal of Chemistry, vol. 44, pp. 2269-2281 (1966).

Fan, Jian-Qiang et al., "Comparison of Acid Hydrolytic Conditions for Asn-Linked Oligosaccharides," Analytical Biochemistry, vol. 219, pp. 375-378 (1994).

Final Office action from the U.S. Patent and Trademark Office for U.S. Appl. No. 10/685,125, dated Jul. 13, 2009.

Final Office action from the U.S. Patent and Trademark Office for U.S. Appl. No. 11/395,013, dated Jul. 6, 2010.

Guoqi, Wu et al., "The Preparation and Application of Oligochitosan," Abstract Only, pp. 14 (1996).

Notice of Allowance from the U.S. Patent and Trademark Office for U.S. Appl. No. 10/685,125, dated Jun. 28, 2010.

Office Action from the Chinese Patent Office for Chinese Patent Application No. 02806321.X, dated Apr. 29, 2005.

Office Action from the Chinese Patent Office for Chinese Patent Application No. 02806321.X, dated Jul. 21, 2006.

Office Action from the Chinese Patent Office for Chinese Patent Application No. 02806321.X, dated Apr. 6, 2007.

Office Action from the European Patent Office for European Patent Application No. 02742474.6, dated Jul. 10, 2007.

Office Action from the European Patent Office for European Patent Application No. 02742474.6, dated Sep. 17, 2008.

Office Action from the European Patent Office for European Patent Application No. 07753854.4, dated Aug. 3, 2009.

Office Action from the European Patent Office for European Patent Application No. 07753949.2, dated Apr. 9, 2010.

Office Action from the Japanese Patent Office for Japanese Patent Application No. 2002-566371, dated Apr. 17, 2006.

Office action from the U.S. Patent and Trademark Office for U.S. Appl. No. 10/685,125, dated Jan. 28, 2010.

Office action from the U.S. Patent and Trademark Office for U.S. Appl. No. 11/395,013, dated Oct. 14, 2009.

Restriction Requirement from the U.S. Patent and Trademark Office for U.S. Appl. No. 11/395,013, dated Jun. 2, 2009.

Rupley, J.A., "The Hydrolysis of Chitin by Concentrated Hydrochloric Acid, and the Preparation of Low-Molecular-Weight Substrates for Lysozyme," Biochimica et Biophysica Acta, vol. 83, No. 3, pp. 245-255 (Nov. 1, 1964).

Sandula, J. et al., "Microbial (1 $\rightarrow$ 3)-$\beta$-D-glucans, their preparation, physico-chemical characterization and immunomodulatory activity," Carbohydrate Polymers, vol. 38, pp. 247-253 (1999).

Shahidi, Fereidoon et al., "Chitin, Chitosan, and Co-Products: Chemistry, Production, Applications, and Health Effects," in Advances in Food and Nutrition Research, vol. 49, pp. 93-135 (2005).

Summons from the European Patent Office for European Patent Application No. 02742474.6, dated Feb. 22, 2010.

Chen, George C. et al., "Improved Colorimetric Determination of Cell Wall Chitin in Wood Decay Fungi," Applied and Environmental Microbiology, vol. 46, No. 1, pp. 13-16 (Jul. 1983).

Nilsson, Kent et al., "Chitin as an indicator of the biomass of two wood-decay fungi in relation to temperature, incubation time, and media composition," Can. J. Microbiol., vol. 44, pp. 575-581 (1998).

Novikov, V. Yu., "Kinetics of formation of D-(+)-glucosamine in acid hydrolysis of chitin," Russian Journal (Sankt-Peterburg), vol. 72, No. 1, pp. 147-152 (1999).

Plassard, Claude S. et al., "Estimation of Mycelial Growth of Basidiomycetes by Means of Chitin Determination," Phytochemistry, vol. 21, No. 2, pp. 345-348 (1982).

Office Action from the Canadian Intellectual Property Office for Canadian Patent Application No. 2,438,233, dated Sep. 20, 2010.

* cited by examiner

WATER SOLUBLE β-GLUCAN, GLUCOSAMINE, AND N-ACETYLGLUCOSAMINE COMPOSITIONS AND METHODS FOR MAKING THE SAME

CROSS REFERENCE TO RELATED APPLICATIONS

The present application is a continuation-in-part of pending U.S. patent application Ser. No. 10/685,125, filed Oct. 13, 2003, which is a continuation-in-part of U.S. patent application Ser. No. 10/326,549 filed Dec. 19, 2002, now U.S. Pat. No. 7,049,433 which is a continuation of U.S. patent application Ser. No. 09/785,695 filed Feb. 16, 2001, now abandoned and claims priority from PCT Application No. PCT/US02/04468 filed Feb. 15, 2002, each of which is incorporated herein by reference. This application is also a continuation-in-part of pending PCT Application No. PCT/US03/34846 filed Oct. 31, 2003, which claims the benefit of U.S. Provisional Application No. 60/423,119, filed Nov. 1, 2002, and is a continuation-in-part of PCT/US02/25121, filed Aug. 7, 2002, which claims priority from U.S. application Ser. No. 09/924,865, filed Aug. 8, 2001, which is now U.S. Pat. No. 6,693,188, each of which is also incorporated herein by reference.

FIELD

The present invention is directed to glucosamine and/or N-acetylglucosamine and/or water soluble β-glucan compositions and to methods of making the same from fungal biomass.

BACKGROUND

Glucosamine is a nutraceutical supplement that has been shown to provide significant therapeutic relief for arthritis and joint pain. Although the mechanism is not entirely known, it is believed that glucosamine functions to aid in restoration of the cartilage to relieve inflammation in the joints, thereby providing significant benefit to users. N-acetylglucosamine is useful for various applications such as food additives and for use in cosmetics and pharmaceutical compositions.

Presently, glucosamine is primarily derived from harvested natural sources, such as shellfish and other aquatic organisms. Chitin from the shell or exoskeleton of these organisms is converted into glucosamine and/or N-acetylglucosamine using various production techniques. These natural sources are acceptable for producing glucosamine and/or N-acetylglucosamine for some applications, but they have limitations. These limitations include the fact that wild shellfish can have significant variations in their shell composition because they grow naturally under uncontrolled circumstances. The shellfish can vary in such aspects as their size and composition depending upon the growing conditions as well as their species. Also, without control over the growing conditions, the shellfish can be exposed to environmental contaminants, including heavy metals, that can be retained in glucosamine, N-acetylglucosamine or other products derived or produced from the shellfish. Shellfish harvests are often seasonal, and thus the supply and price of shellfish shows significant variation over time.

A further concern with glucosamine and/or N-acetylglucosamine derived from shellfish is that significant portions of the human population have shellfish allergies and are unable to use products that contain ingredients derived from shellfish. A large percentage of shellfish allergens are specific proteins. Shellfish allergens, such as muscle proteins (e.g., tropomyosin) are found in glucosamine derived from the shellfish sources. It is not economically practical, if even possible to ensure that glucosamine and/or N-acetylglucosamine products derived from shellfish sources are completely free of all traces of shellfish allergens. Thus, hyper allergenic individuals who must avoid all shellfish products cannot ingest materials derived from shellfish, such as glucosamine and/or N-acetylglucosamine.

An additional problem associated with existing sources of shellfish-derived glucosamine and/or N-acetylglucosamine is that some of the shellfish supply is harvested from the seas and oceans of the world. Excessive harvest of shellfish could have a great negative environmental impact. Thus, it is believed that some consumers would prefer to use glucosamine that is not harvested at the expense of sea life. Even if the environmental impact of harvesting shellfish is not negative, there remains concern that the supply of wild shellfish is limited in quantity and inconsistent in quality from year to year.

Another problem associated with glucosamine and/or N-acetylglucosamine compositions derived from shellfish is that such compositions are not "kosher." "Kosher" means fit or proper, and is generally used to describe foods that are prepared in accordance with special Jewish dietary laws. Many people that practice Judaism will only ingest kosher products. All shellfish are non-kosher foods and thus all products derived from shellfish are not immediately considered kosher. For certain medicinal applications, a shellfish glucosamine product can receive special dispensation such that it is considered kosher. Specially dispensed kosher shellfish-derived glucosamine may be used for medicinal applications only and even then may only be ingested in pill or tablet form. Accordingly, "fully certified kosher" glucosamine and/or N-acetylglucosamine compositions (i.e., kosher products not requiring special dispensation or restricted to medicinal uses in pill or tablet form) are needed. Likewise, many vegans require animal-product free glucosamine and/or N-acetylglucosamine compositions such that glucosamine and/or N-acetylglucosamine compositions derived from shellfish do not meet their dietary needs.

Therefore, a need exists for a source of safe, kosher, non-animal product derived, high-quality glucosamine and/or N-acetylglucosamine compositions that can be created economically and with minimal environmental impact.

In addition, fungal sources to produce glucosamine and N-acetylglucosamine contain β-glucans and other components. β-Glucans are polymers of glucose containing glycosidic bonds between the glucose units. β-Glucans are glucans where the glycosidic bonds are predominantly β linkages. The β-glucans in these sources comprise β-1,3-glucans, as well as β-1,4 and β-1,6 glycosidic bonds and branches comprising β-1,3,6 glycosidic linkages. The types and number of the glycosidic linkages depends to a large extent on the source of the β-glucans. For example, yeast sources of β-glucans have not been reported to include β-glucans having the β-1,4 linkages.

β-glucans are naturally insoluble in water, acidic or basic solutions, or in organic solvents. A number of processes for the isolation and purification of β-glucans have been developed. The known methods, however, use hot alkali, acids, or a combination of both to solubilize proteins and other components of the biomass, leaving the insoluble β-glucans. The acid or base must then be removed from the insoluble β-glucans by washing with water. The high water-absorbing capacity of β-glucans causes them to swell significantly, making this step difficult and tedious.

The digestibility or applicability of β-glucans from these sources is limited by their insolubility. Converting β-glucans to soluble forms has required uses of acids, bases, or oxidizing agents to break down the polymers into smaller polymers to render them soluble. These same chemical agents can have adverse effects on the glucose units, such as oxidizing the alcohol to aldehyde or acid forms. This is disadvantageous not only because β-glucan applications prefer β-glucans that are not chemically altered but also because such oxidations are difficult to control precisely. Further, chemical treatments require additional purification steps to remove the acids, bases, or oxidizing agents. A process requiring a minimal chemical treatment and minimal or no chemical structure change to the β-glucan structure are desirable.

To keep the native structure of the β-glucans while rendering the β-glucans water soluble by, e.g., controlling molecular weight there is a need for a mild manufacturing process in which β-glucan is not degraded or chemically altered during the process, a sufficient yield of β-glucan is obtained and undesirable components such as proteins, lipids, other polysaccharides as well as other undesirable components in the β-glucan source are removed from the β-glucan compositions.

Nonetheless, β-glucans are recently in demand for a variety of applications such as immunostimulants for animal feed use, immunostimulants, and/or cholesterol treatments, and/or as ingestible fiber sources for human use, as treatment for agriculture, and for use in skin treatment products such as moisturizers.

The mechanism of the effect of β-glucans, and β-1,3-D-glucans in particular, is not yet fully understood but appears to depend upon, in part, the specific molecular structure, which is influenced by the molecular weight and the solubility of the polymers. Certain β-glucans have been found to be more effective than others, with β-1,3-D-glucans being especially effective.

SUMMARY

Disclosed are glucosamine and/or N-acetylglucosamine compositions, including glucosamine and/or N-acetylglucosamine composition products suitable for human or animal consumption. The disclosed glucosamine and/or N-acetylglucosamine compositions are derived from fungal biomass containing chitin. Suitable starting materials include microbial fungal sources, such as fungal sources derived from *Aspergillus* sp., *Penicillium* sp., *Mucor* sp., and combinations thereof. Use of a fungal biomass results in high quality glucosamine compositions that are generally uniform with low levels of impurities. The glucosamine compositions normally have relatively low ash content, and are free of or substantially free of heavy metal contaminants. In addition, as a product of fungal biomass, the glucosamine and/or N-acetylglucosamine compositions do not pose a hazard to persons who have shellfish allergies. That is, tropomyosin and other such muscle-derived proteins are not present in fungal biomass. Because the disclosed glucosamine and/or N-acetylglucosamine compositions are not derived from shellfish (or any animal source), the disclosed compositions are both kosher and may be consumed by strict vegetarians. Shellfish and products derived from shellfish are not considered kosher by any guidelines regarding kosher products.

Particular embodiments of the disclosed glucosamine compositions comprise glucosamine and no shellfish allergens. Other embodiments of the disclosed glucosamine compositions include kosher glucosamine. Other embodiments of the disclosed glucosamine compositions comprise glucosamine and an absence of animal-derived products. Yet other embodiments of the disclosed glucosamine compositions comprise glucosamine and melanoidins. Further embodiments of the disclosed glucosamine compositions comprise glucosamine, melanoidins, and/or levulinic acid. Other embodiments of the disclosed glucosamine compositions have lipophilic oxygen radical absorbance capacity (ORAC) values of from 30 μmole TE/g to 150 μmole TE/g or from 35 μmole TE/g to 100 μmole TE/g or from 35 μmole TE/g to 50 μmole TE/g. Certain of the N-acetylglucosamine compositions are kosher N-acetylglucosamine compositions and are free of shellfish allergen (and the threat or uncertainty of containing any shellfish allergens), and are free of such allergens without need for any purification of the compositions so as to remove doubt of existence of such allergens in the compositions.

Also disclosed are various methods for producing glucosamine compositions by acid hydrolysis of fungal biomass. The methods for obtaining glucosamine compositions from microbial biomass include, for example, reacting chitin-containing biomass in a relatively concentrated acidic solution at a relatively elevated temperature. Also disclosed are methods for obtaining glucosamine compositions from fungal biomass by, for example, reacting the chitin-containing biomass in a relatively mild acidic solution and then in a relatively concentrated acidic solution. In an alternative embodiment, the microbial chitin-containing biomass is reacted with a basic solution before or after acid hydrolysis treatment. In yet another embodiment, fungal biomass is treated with an acidic solution at an elevated temperature and/or pressure to produce glucosamine compositions.

Also disclosed are methods for producing either glucosamine or N-acetylglucosamine. In certain of these embodiments greater than about 80% of the chitin remaining in the fungal biomass is converted to N-acetylglucosamine (NAG). In particular embodiments the fungal biomass is pretreated with an enzymatic pretreatment and/or a mild acid pretreatment to partially breakdown the biomass cell walls and to convert certain undesirable products to soluble forms. The solids are separated and an enzymatic treatment is next utilized to convert the chitin to NAG. In certain embodiments the resulting product including the desired N-acetylglucosamine product also includes undesirable products such as glucose. Accordingly, in some embodiments, the N-acetylglucosamine and glucose mixture is treated again with certain enzymes to convert the glucose to ionic forms that are readily removed from the N-acetylglucosamine in the mixture. In other embodiments, the enzymes to convert chitin to NAG and the enzymes to convert glucose to ionic forms are applied in a single step.

Some embodiments of the disclosed method also include a further purification of the N-acetylglucosamine composition. In yet other of the disclosed methods, the purified N-acetylglucosamine is treated to form N-acetylglucosamine crystals. In other of the disclosed methods, the purified N-acetylglucosamine composition is deacetylated to form glucosamine hydrochloride.

In alternative embodiments, the biomass is pretreated enzymatically and/or with a mild acid precook, the chitin is enzymatically converted to N-acetylglucosamine and the resulting composition is then deacetylated to form glucosamine. In other embodiments, the biomass is pretreated enzymatically and/or with a mild acid treatment, the chitin is converted enzymatically to N-acetylglucosamine, the glucose is converted enzymatically to ionic forms, and the N-acetylglucosamine is deacetylated to form glucosamine. In other embodiments the biomass is pretreated enzymatically and/or with a mild acid pretreatment, the chitin is converted to N-acetylglucosamine enzymatically, and glucose present in the N-acetylglucosamine composition is enzymatically treated for removal, the N-acetylglucosamine composition is next purified and the purified N-acetylglucosamine composition is deacetylated to form glucosamine.

Also disclosed are β-glucan compositions comprising water-soluble β-glucans. In certain composition embodiments the β-glucan compositions comprise water-soluble β-glucans derived from fungal biomass. In some embodiments the water-soluble β-glucans compositions comprise β-1,3-D-glucans having an average molecular weight of less than about 1,000,000. Certain embodiments include water-soluble β-glucans compositions comprising β-1,3-D-glucans having a molecular weight range of from about 346 to about 5,000,000. In other embodiments the water-soluble β-glucan compositions comprise at least about 50% by weight β-1,3-D-glucans. In other embodiments the water-soluble β-glucan compositions comprise at least about 70% by weight β-1,3-D-glucans. In certain embodiments the water-soluble β-glucan compositions comprise a ratio of α to β of about 1 to about 8. In other embodiments the water-soluble β-glucan compositions comprise a ratio of α glycosidic linkages to β glycosidic linkages of from about 1 to about 20 to about 1 to about 5. In certain embodiments the water-soluble β-glucan compositions comprise at least about 50 to 70% by dry weight 1,3-β-D-glucans and less than about 8% by dry weight 1,4-β-D-glucans.

In some embodiments the β-glucans in the water-soluble β-glucan compositions have solubilities in aqueous solution of from about 20 wt % to about 60 wt % or from about 30 wt % to about 50 wt % or from about 40 wt % to about 50 wt %.

Also disclosed are (1) methods of producing the above-described β-glucan compositions, (2) methods of isolating β-glucans, (3) methods of isolating β-glucans from fungal biomass sources by forming aqueous soluble fungal β-glucans, (4) methods of treating animal feed, crops, and/or humans with the disclosed β-glucan compositions. Particular embodiments of the disclosed methods produce β-glucan compositions include a mild manufacturing process in which β-glucan molecular weights are controlled by the process, a sufficient yield of β-glucan obtained and undesirable components such as proteins, lipids, other polysaccharides as well as other undesirable components in the β-glucan source are removed from the β-glucan compositions.

DRAWINGS

DETAILED DESCRIPTION

Figure 1:
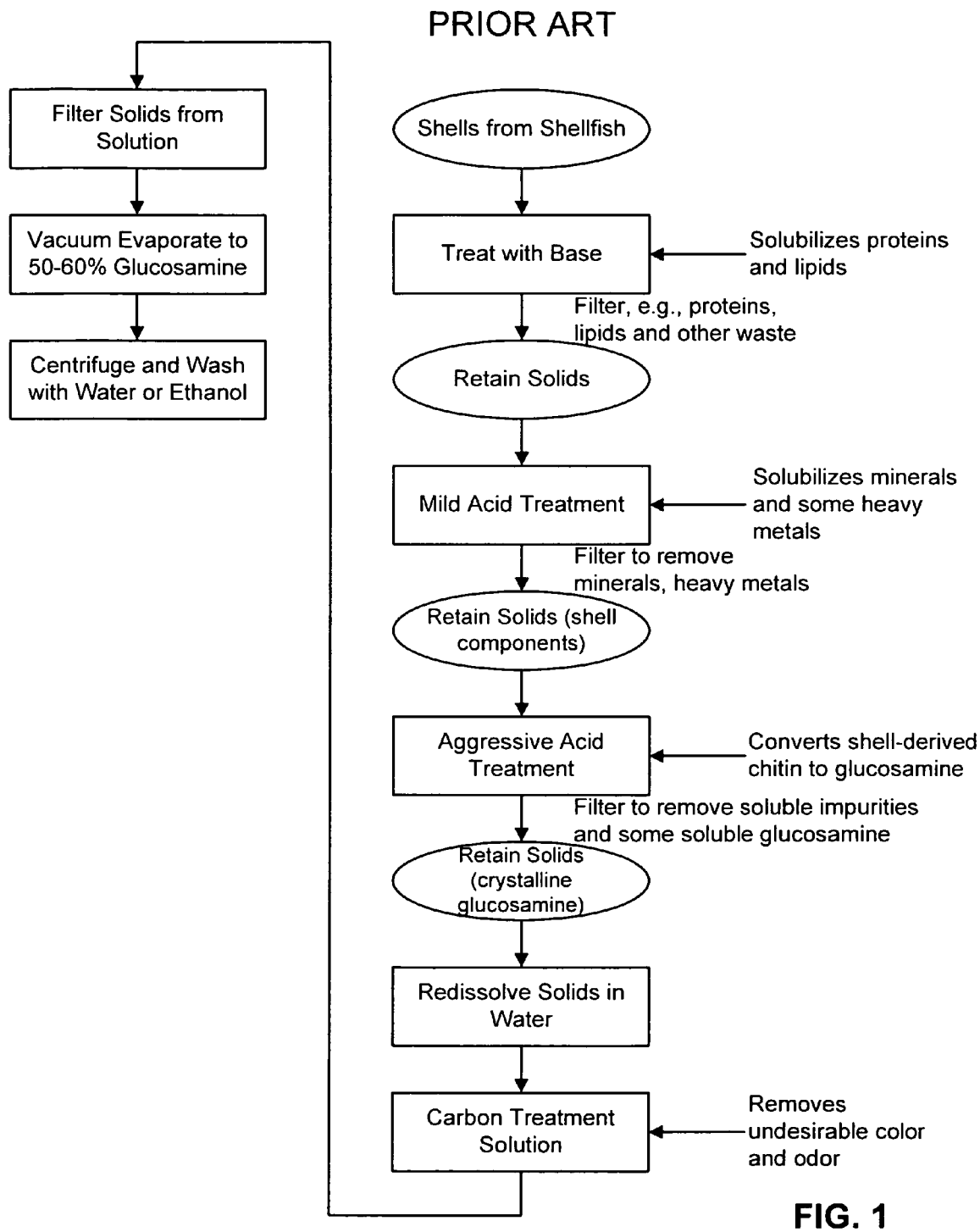
FIG. 1 is a prior art flow diagram illustrating a process for producing glucosamine from shellfish.

Disclosed are glucosamine and/or N-acetylglucosamine compositions and glucosamine and/or N-acetylglucosamine composition products, such as food supplements, suitable for human or animal consumption. The glucosamine and/or N-acetylglucosamine compositions are derived from chitin present in various types of fungal biomass. Chitin is a natural polysaccharide, with the structure of an unbranched polymer of 2-acetoamido-2-deoxy-D-glucose (poly(N-acetyl-D-glucosamine)). Chitin contains N-acetylglucosamine units and may also contain up to about 50% deacetylated units. The formula for chitin can be represented by the general repeating structure:

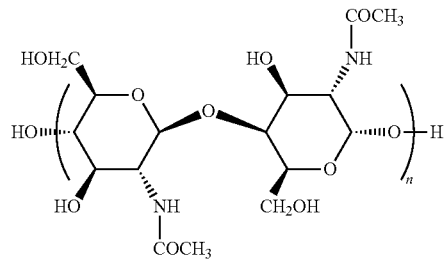

Chitin is typically an amorphous solid that is largely insoluble in water, dilute acids, and alkali. Although chitin has various commercial applications, commercial utility can be found by transforming the polymeric structure into individual components of 2-amino-2-deoxy-D-glucose, which is known as glucosamine. Structurally, glucosamine is modified glucose with an amine group replacing the OH group found on the carbon two (C-2) atom. The general structure of glucosamine is:

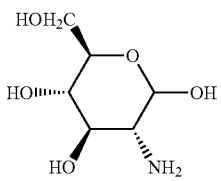

Chitin can also be depolymerized to form the amino sugar N-acetylglucosamine (NAG). N-acetylglucosamine compositions typically include a single acetylglucosamine monomer, but also can include small amounts of oligomers that have, e.g., two or three acetylglucosamine units. N-acetylglucosamine can be used for various applications, such as food additives, dietary supplements, cosmetics, or in pharmaceutical compositions.

As stated above, glucosamine compositions disclosed herein include glucosamine and N-acetylglucosamine derived from fungal biomass containing chitin and may include other components as well. Suitable starting materials for producing the glucosamine and/or N-acetylglucosamine compositions include substantially uniform microbial fungal sources, such as fungal sources derived from *Aspergillus* sp., *Penicillium* sp., *Mucor* sp. *Absidia* sp., *Actinomucor* sp., *Actostelium* sp., *Agaricus* sp., *Allomyces* sp., *Amylomyces* sp., *Coprinus*, sp., *Cunninghamella* sp., *Didymium* sp., *Fusarium* sp., *Gongronella* sp., *Lentinula* sp., *Mortierella* sp., *Mucoriopsis* sp., *Phycomyces* sp., *Rhizomucor* sp., and *Rhizopus* sp., and combinations thereof. Other useful sources of fungal biomass may include, without limitation, *Absidia ramosa, Gongronella butlerii, Mortierella spinosa, Mucor racemosus, Rhizopus nigricans, R. stolonifer, R. oryzae, A. nidulans, Thielavia terricola, Saccharomyces cerevisiae, Cheatomium lunasporium*, and combinations thereof. Use of a fungal biomass results in a high-quality product that produces glucosamine compositions having low levels of impurities, such as undesirable minerals. The glucosamine compositions normally have relatively low ash content and thus, no or at most trace levels of heavy metals. In addition, low ash content provides relatively clear solutions made from the glucosamine compositions.

In addition, because the glucosamine compositions are products of fungal biomass, the glucosamine compositions disclosed herein are not subject to inclusion of the protein allergens found in glucosamine produced from shellfish.

A. Glucosamine and N-acetylglucosamine Compositions

The glucosamine and N-acetylglucosamine compositions may be derived from relatively uniform fungal biomass sources, so that the glucosamine compositions are generally uniform. "Uniform fungal biomass" refers to fungal biomass comprising substantially the same species grown on substantially the same media, grown in a relatively controlled environment or other such conditions that lead to substantial uniformity in the biochemical make-up of the biomass. Depending upon the methodology used to purify the glucosamine compositions such as desired glucosamine salt compositions, the resulting glucosamine containing compositions can be produced with varying amounts of glucosamine, including compositions that exceed 95 percent glucosamine, 98 percent glucosamine, and even 99.8 percent glucosamine. The glucosamine compositions can contain additional ingredients, such as salts, melanoidins and acids, e.g., levulinic acid (as discussed below). Certain of the glucosamine compositions include 0.01 to 10% glucose, 0.01 to 5% glucose, or 0.01 to 2% glucose.

Likewise, depending upon the methodology used to purify the N-acetylglucosamine compositions, the resulting N-acetylglucosamine containing compositions can be produced with varying amounts of N-acetylglucosamine, including compositions that exceed 90 percent N-acetylglucosamine, 95 percent N-acetylglucosamine, and even 99.8 percent N-acetylglucosamine, by weight. In addition, certain embodiments of the methods (discussed in detail below) disclosed herein for forming the N-acetylglucosamine convert at least about 80% of the chitin obtained from the biomass to N-acetylglucosamine, and some methods disclosed convert at least about 95% of the chitin obtained from the biomass to N-acetylglucosamine.

Unless otherwise indicated, all numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

The glucosamine in the disclosed compositions has the general formula represented below:

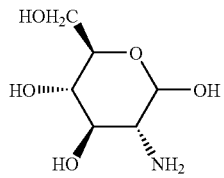

This general formula varies in different embodiments of the glucosamine compositions depending upon the presence of various salts of the glucosamine, including citrate, acetate, phosphate, sulfate, chloride, lactate, gluconate, etc. Also, the glucosamine in the glucosamine compositions can be substituted or modified without diverging from the scope of the invention. Thus, as used herein, the term glucosamine refers to the various forms of glucosamine, including salt complexes and substituted glucosamine. Likewise, the term glucosamine composition refers to compositions including glucosamine in such various forms.

Embodiments of the glucosamine compositions include particular components in addition to glucosamine, such as chitooligosachharides and products of glucan depolymerization, reaction, and degradation, such as glucose, melanoidins and levulinic acid.

Melanoidins are relatively complex, high molecular weight, irregular polymers and are present in particular embodiments of the glucosamine compositions. For example, particular embodiments of the disclosed glucosamine compositions include from 0.001 to 15 wt. % melanoidins or from 0.001 to 1.0 wt. % melanoidins or from 0.01 to 0.1 wt. % melanoidins. Without being tied to any particular theory, melanoidins are likely formed by the conversion of glucans to glucose to hydroxymethylurfural (HMF) to produce the melanoidins. (The reaction may produce other glucan-derived products and amines from proteins in a biomass source as well as lipids in such a source.) Such a chemical process is known as the Maillard Reaction.

Levulinic acid (also known as acetyl-propionic acid) is present in particular embodiments of the disclosed glucosamine compositions. Without being tied to any particular theory, levulinic acid is likely formed when glucans in the fungal biomass are converted to glucose, which is converted to HMF to finally form formic and levulinic acids. Levulinic acid is a non-hazardous component that is a valuable acidulant used in such products as carbonated and fruit juice beverages, jams, and jellies. Thus, addition of embodiments of the glucosamine compositions to such products provides an acidulant benefit as well as the benefits provided by the glucosamine in the composition. Particular embodiments of the glucosamine compositions include from 0.0001 to 1 wt. % levulinic acid, or from 0.001 to 0.7 wt. % levulinic acid or from 0.01 to 0.4 wt. % levulinic acid.

Because the melanoidins and levulinic acid are formed when producing the glucosamine compositions according to the disclosed methods, no additional steps must be taken to include such components in the compositions. Melanoidins and levulinic acid were not expected in glucosamine compositions derived from shellfish, and analysis of six lots of glucosamine derived from shellfish (obtained from five different suppliers) did not contain any detectable amounts of melanoidins or levulinic acid.

Figure 7:
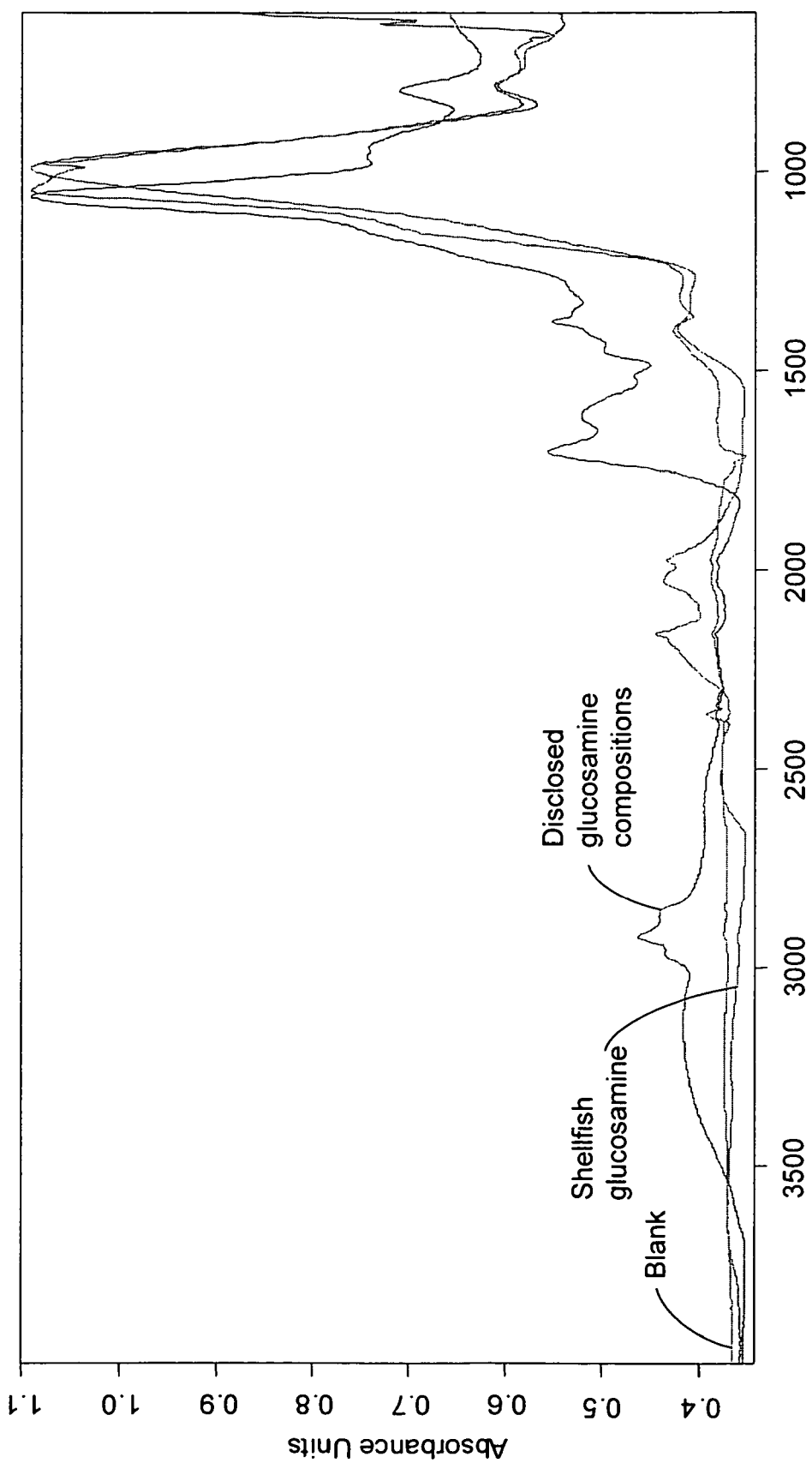
FIG. 7 is a series of FTIR spectra showing comparison of certain of the presently disclosed glucosamine compositions to glucosamine materials derived from shellfish.

As discussed, complex carbohydrates in fungal biomass, such as glucans, are converted to melanoidins in the reducing environment of the process. These complex carbohydrates are not present in the shellfish carapaces used in other processes, and so the melanoidins do not form. Comparison of FTIR spectra (FIG. 7) of water-insoluble materials in certain embodiments of the disclosed glucosamine compositions to those found in a typical shellfish-derived glucosamine shows that melanoidins are not present in shellfish derived glucosamine compositions. The FTIR spectrum of the insoluble material from the disclosed glucosamine composition has several broad bands with no fine structure, typical of polymeric materials. The bands between 2800 and 3000 wave numbers in the spectrum of the present compositions are typical of amide groups in melanoidins. The insoluble material from the shellfish derived glucosamine product has no such indications of the presence of melanoidins in the FTIR spectra.

Because melanoidins are irregular polymers with reduced carbon, some degree of conjugation exists between the pi bonds. This conjugation results in the typical tan to brown color of melanoidins. Such coloration was clearly present in embodiments of the presently disclosed glucosamine compositions but was absent in the shellfish-derived glucosamine samples again indicating that shellfish derived glucosamine compositions do not include melanoidins.

Melanoidins are reported to possess antioxidant and/or free radical scavenging character. See, e.g., Gow-Chin Yen, et al., *Antioxidant Activity and Scavenging Effects on Active Oxygen of Xylose-Lysine Maillard Reaction Products*, J. Sci. Food Agric., 67, 415-420 (1995); K. Eichner, *Antioxidant Effect of Maillard Reaction Intermediates*, Prog. Fd. Nutr. Sci., 5, 441-451 (1981); Fumitaka Hayase, et al., *Scavenging of Active Oxygens by Melanoidins*, Agric. Biol. Chem, 53(12), 3383-3385 (1989); Dejian Huang, et al., *High-Throughput Assay of Oxygen Radical Absorbance Capacity (ORAC) Using a Multichannel Handling System Coupled with a Microplate Fluorescence Reader in 96-Well Format*, J. Agric. Food Chem., 50, No. 16, 4437-4444 (2002), each of which is incorporated herein by reference. Certain embodiments of the glucosamine compositions disclosed have lipophilic oxygen radical absorbance capacity values (lipo-ORAC values) of from 30 μmole TE/g (TROLOX equivalent per gram) to 150 μmole TE/g or lipo-ORAC values of from 35 μmole TE/g to 100 μmole TE/g or from 35 μmole TE/g to 50 mmole TE/g. TROLOX is also known as 6-hydroxy-2,5,7,8-tetramethyl-2-carboxylic acid.

The lipo-ORAC values may be determined, e.g., by use of an ORAC assay using fluorescein (FL) as a fluorescent probe as discussed in Dejian Huang, et al., *Development and Validation of Oxygen Radical Absorbance Capacity Assay for Lipophilic Antioxidants Using Randomly Methylated β-Cyclodextrin as the Solubility Enhancer*, J. Agric. Food Chem., 50, No. 7 (2002), which is incorporated herein by reference. Randomly methylated β-cyclodextrin (RMCD) is used as a water solubility enhancer for lipophilic antioxidants. Seven percent RMCD (w/v) in a 50% acetone-water mixture is used to solubilize the lipophilic antioxidants in 75 mM phosphate buffer (pH 7.4). When using TROLOX as the standard (1.0), α-tocopherol, (+)-γ-tocopherol, (+)-δ-tocopherol, α-tocopherol acetate, tocotrienols, 2,6-di-tert-butyl-4-methylphenol, and γ-oryzanol have ORAC values of 0.5+/−0.02, 0.74+/−0.03, 1.36+/−0.14, 0.00, 0.91+/−0.04, 0.16+/−0.01, and 3.00+/−0.26, respectively, when using this method.

Levulinic acid and glucose, present in certain embodiments of the disclosed glucosamine compositions are not expected to be present in glucosamine derived from shellfish. High performance liquid chromatography demonstrates the differences between embodiments of the glucosamine composition disclosed herein and shellfish-derived glucosamine compositions. Neither levulinic acid nor glucose was detected in any shellfish-derived glucosamine products.

Figure 8:
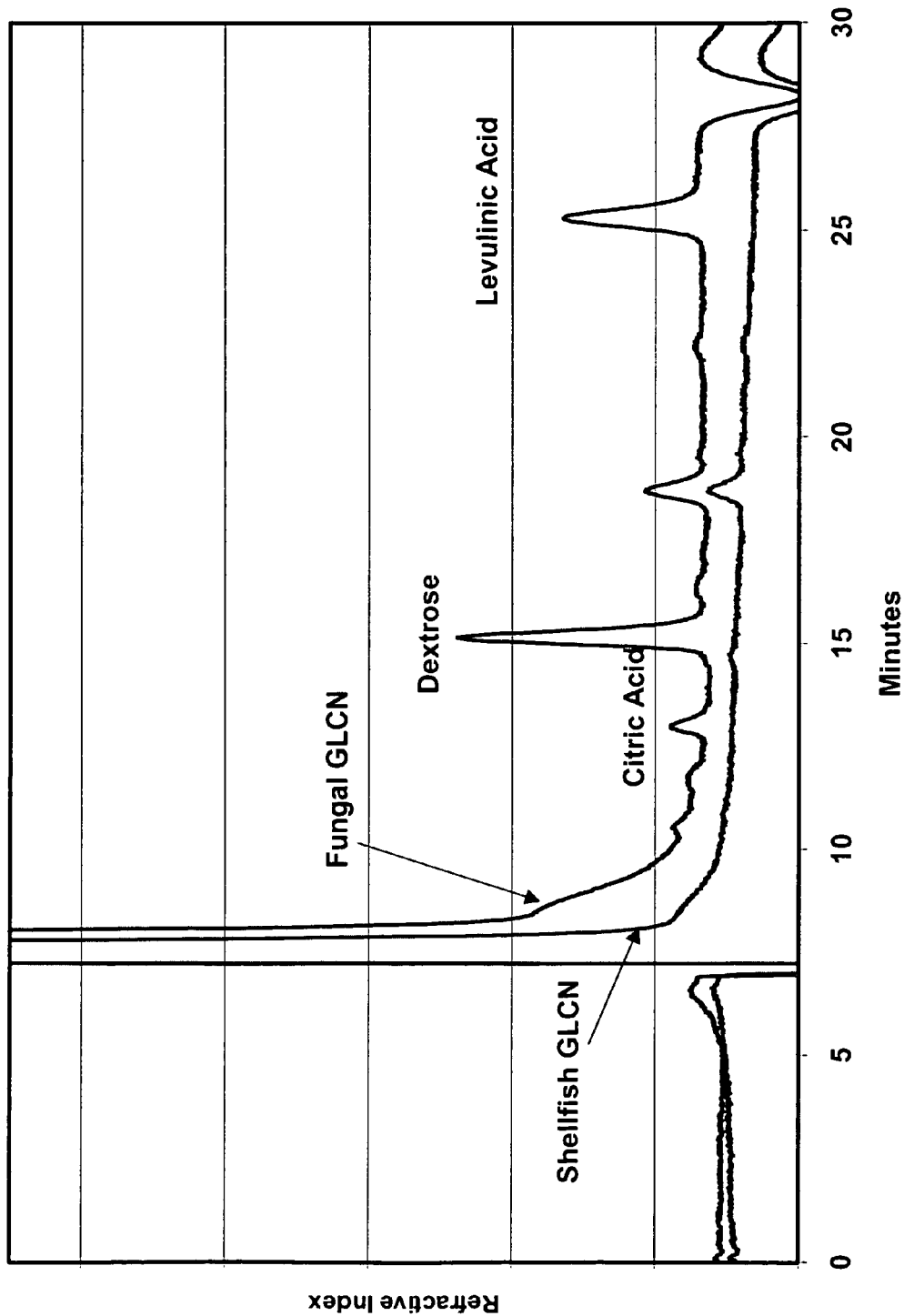
FIG. 8 is an HPLC chromatogram that compares water-soluble components of an embodiment of the disclosed composition to glucosamine derived from fungal biomass indicating that no levulinic acid or glucose was detected in the shellfish-derived glucosamine.

Specifically, samples of the present compositions and shellfish-derived glucosamine compositions were dissolved in 0.01 N sulfuric acid at a concentration of 4% w/v. Diluted samples were filtered through 0.2 mm nylon filters into HPLC vials. Chromatograms were collected using a Metacarb H Plus column (Varian, Inc., Torrence, Calif.) using 0.01 N sulfuric acid as the eluent at 0.4 mL/min. Peaks were identified by retention time against known standards. As is apparent in FIG. 8, levulinic acid and glucose were present only in the presently disclosed glucosamine compositions and not in the shellfish derived compositions.

With reference to Table 1, embodiments of the glucosamine compositions comprise glucosamine derived from fungal biomass and may also comprise one or more of the listed components in Table 1, those shown in Table 2 and other components as discussed herein. Concentrations of each component may be within the ranges shown or may be varied by altering any of a variety of production parameters.

TABLE 1

| Glucosamine Composition Components | Representative Embodiment Percent by Weight | Representative Embodiment Percent by Weight | Representative Embodiment Percent by Weight |
|---|---|---|---|
| Glucosamine | 85-99.8 | 95-99.8 | 98-99.8 |
| Melanoidins | 0.001-15 | 0.001-1.0 | 0.01-0.1 |
| Levulinic Acid | 0.0001-1 | 0.001-0.7 | 0.01-0.4 |
| Glucose | 0.001-10 | 0.001-5 | 0.001-2 |
| Citric Acid | 0.001-10 | 0.01-1.0 | 0.025-0.5 |

With reference to Table 2, two specific embodiments of the glucosamine compositions are set forth. The methods utilized to determine the components present and concentrations of the same are set forth below.

TABLE 2

| Composition Component | *Embodiment 1 (GP-11) | *Embodiment 2 (GP-17C) |
|---|---|---|
| Ash Content | 0.03% | 0.02% |
| Si | 140 ppm | 150 ppm |
| Na | 10-100 ppm | 10-100 ppm |
| K | 10-100 ppm | 10-100 ppm |

TABLE 2-continued

| Composition Component | *Embodiment 1 (GP-11) | *Embodiment 2 (GP-17C) |
|---|---|---|
| Ca | 10-100 ppm | 10-100 ppm |
| HCL | 0.16% | 0.19% |
| Citric Acid | 0.045% | 0.074% |
| Levulinic Acid | 0.39% | 0.3% |
| Melanoidins | 0.04-0.07% | 0.02-0.03% |
| Water-insoluble matter soluble in gastric juice at ~40° | 0.05% | 0.02% |

*Percentages listed are percents by weight

Certain embodiments of the glucosamine compositions have relatively low ash content. The ash content may be less than 5 percent, less than 2 percent, or less than 1 percent. There are little if any heavy metal components in the glucosamine compositions; the heavy metal component concentrations in the disclosed glucosamine compositions are well below 100 parts per million, more typically below 50 parts per million, even more typically below 20 parts per million. In certain embodiments the heavy metal components are present in less than 10 parts per million.

The glucosamine component of the glucosamine compositions can have a positive specific rotation, such as a positive 69 to 74 degree specific rotation for the glucosamine hydrochloride salt. The glucosamine compositions are usually relatively white when in purified dry form, but colorless when dissolved in an aqueous solution. In one example, a 20 percent by weight solution of the glucosamine has an American Public Health Association (APHA) color of less than 50.

The N-acetylglucosamine in the disclosed compositions has the general formula represented below:

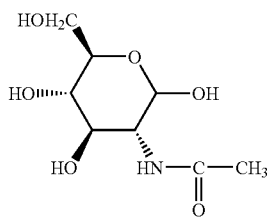

This general formula varies in different embodiments of the N-acetylglucosamine compositions depending upon the presence of oligomers of N-acetylglucosamine, such as dimers, trimers, and so on, up to about ten repeat units. Also, the N-acetylglucosamine in the N-acetylglucosamine compositions can be substituted or modified without diverging from the scope of the invention. Thus, as used herein, the term N-acetylglucosamine refers to the various forms of N-acetylglucosamine, including oligomers. Likewise, the term N-acetylglucosamine composition refers to compositions including N-acetylglucosamine in such various forms.

The glucosamine and/or N-acetylglucosamine compositions may also be combined with further components to form a food supplement for human and/or animal ingestion. For example, the glucosamine and/or N-acetylglucosamine compositions may be further combined with excipients, common pharmaceutical binders (e.g., sucrose, glucose, ethyl cellulose, methyl cellulose, polyvinyl pyrrolidone, polyethylene glycol, lactose, dicalcium phosphate, crosprovidone, croscarmellose, and the like), common organic acids (e.g., citric acid, malic acid, tartaric acid, lactic acid, and the like), and/or carbohydrates (e.g., starch, glucose, sucrose, and the like). Such glucosamine and/or N-acetylglucosamine compositions may also be combined with sugars, artificial sweeteners, natural and artificial colors, natural and artificial flavorings, acidulants, thickeners, and the like, to form a variety of food supplements. Such glucosamine and/or N-acetylglucosamine composition food supplements are typically made into food and/or supplement beverages, bars, concentrates, dry or concentrated drink mixes, powders, chews, confections, gums, yogurts, patches, lozenges, and the like.

B. Fungal Biomass Starting Materials

Suitable starting materials for producing the disclosed glucosamine compositions include microbial biomass sources, typically fungal biomass, such as filamentous fungi having greater than 10 percent chitin by total dry cell weight, such as fungal sources derived from *Aspergillus* sp., *Penicillium* sp., *Mucor* sp., *Absidia* sp., *Actinomucor* sp., *Actostelium* sp., *Agaricus* sp., *Allomyces* sp., *Amylomyces* sp., *Coprinus*, sp., *Cunninghamella* sp., *Didymium* sp., *Fusarium* sp., *Gongronella* sp., *Lentinula* sp., *Mortierella* sp., *Mucoriopsis* sp., *Phycomyces* sp., *Rhizomucor* sp., and *Rhizopus* sp., and combinations thereof. Suitable fungal biomasses include *Aspergillus niger*, *Aspergillus terreus*, *Aspergillus oryzae*, *Mucor rouxii*, *Penicillium chrysogenum*, *Penicillium notatum*, *Saccharomyces cerevisiae*; *Saccharomyces uvarum*; *Absidia ramosa*, *Gongronella butlerii*, *Mucor racemosus*, and in particular *Candida guillermondi*, *Aspergillus niger*, and *Aspergillus terreus*. The biomass may be recovered from a commercial fermentation reaction, such as the commercial production of organic acids, including citric acid. Also, biomass suitable for production of glucosamine and/or N-acetylglucosamine can be generated specifically for this process and not as a byproduct of other processes. As used herein, the term microbial does not include phyto-plankton and crustaceans or mollusks.

Biomasses having chitin levels in excess of 5 percent of the dry biomass weight are suitable for practicing the methods disclosed. Such biomass usually has between 5 and 25 percent chitin, and can have from 10 to 20 percent chitin, based upon dry weight of the biomass. Also, in order to prepare food or supplemental grade glucosamine and/or N-acetylglucosamine compositions it is sometimes desirable that the microbial biomass be grown in a substantially controlled manner having relatively uniform temperature and/or nutrient levels during the growth of the biomass. Nutrient levels can be controlled by any suitable manner, for example as disclosed in U.S. Pat. Nos. 2,739,923, 2,353,771, and 2,674,561, which are incorporated herein by reference.

The same microbial biomass sources, typically fungal biomass sources, may be used for producing the β-glucan compositions disclosed herein. In certain embodiments, the β-glucan source is the "waste" product separated from the liquids in the glucosamine and/or N-acetyl glucosamine methods disclosed herein. As disclosed herein (see, e.g., FIGS. 2, 3, and 9-11) presently disclosed is an overall process for developing glucosamine compositions, N-acetylglucosamine compositions, and β-glucan compositions all from a single starting source of fungal biomass. Conventional processes for producing glucosamine and/or N-acetylglucosamine composition products require the undesirable shellfish source and any of the three compositions require the use of undesirable chemical processes and/or produce relatively large amounts of process chemical waste, including strong acid and base wastes that can be expensive to dispose of properly. In addition, the existing processes for producing glucosamine compositions, N-acetylglucosamine compositions, or β-glucans compositions recovered only those individual compositions from the source (i.e., produce only the glucosamine or N-acetylglucosamine or β-glucan products but did not produce more than one product). The multiple product approach disclosed herein results in more efficient use of capital, lower costs to manufacture, less process chemical waste and more efficient use of the raw materials (less waste of the source materials).

C. Methods for Producing Fungal Biomass Glucosamine Compositions

Also disclosed are methods for producing glucosamine compositions from fungal biomass sources, including producing such compositions by acid hydrolysis of fungal biomass. Acid hydrolysis breaks ether linkages in the biomass and deacetylates chitin molecules to generate free glucosamine. Acid hydrolysis can break the chitin into glucosamine, but leaves the glucosamine molecule substantially intact. Depending upon the acid hydrolysis parameters, acid hydrolysis conditions break down other components (such as glucans, proteins, and lipids) that exist in the fungal biomass.

In one specific of the disclosed method for producing glucosamine compositions from fungal biomass, acid hydrolysis is performed by treating fungal biomass for a relatively long period of time, for example greater than 4 hours, in a relatively aggressive acid solution.

Figure 2:
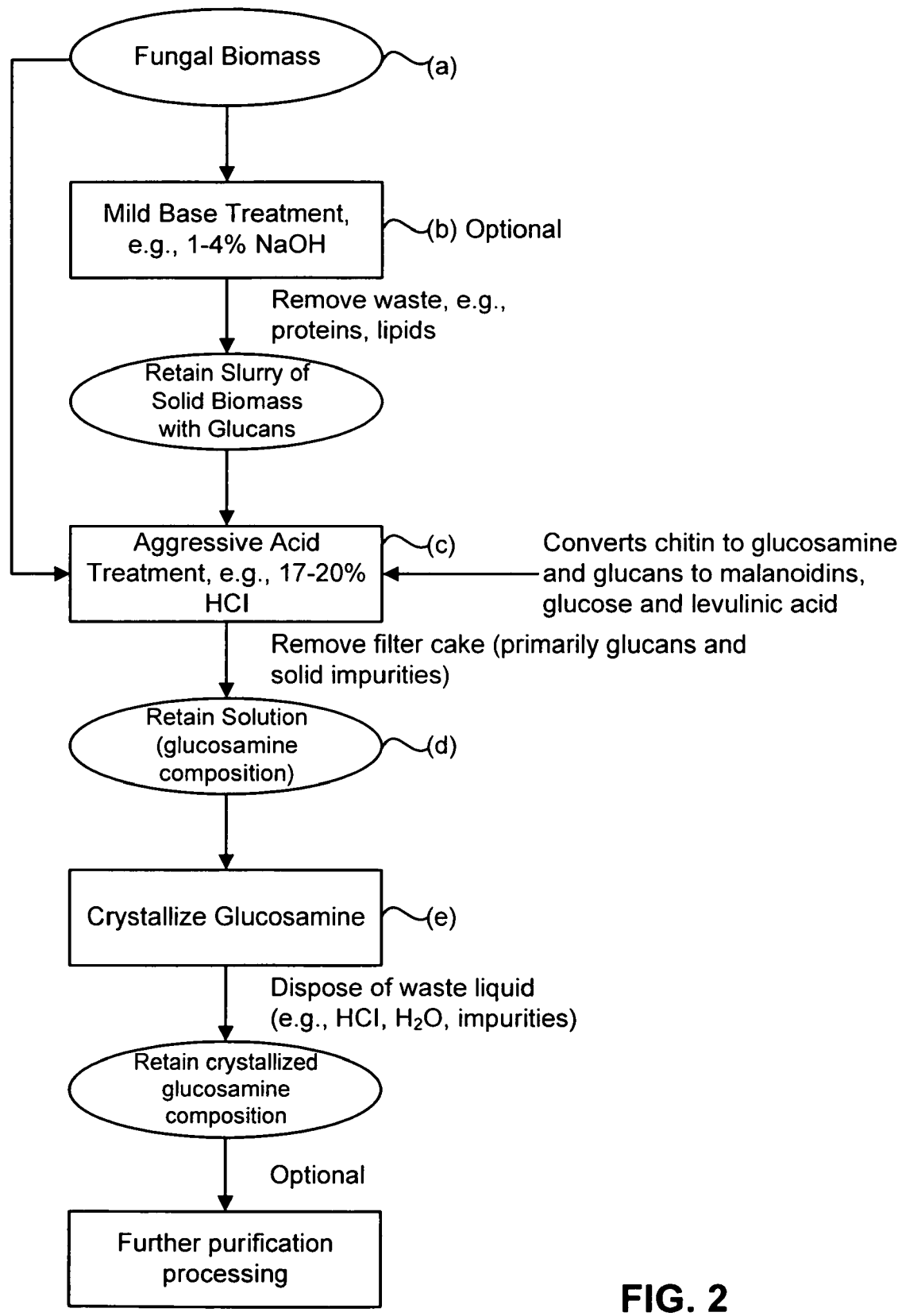
FIG. 2 is a flow diagram of one of the disclosed methods for producing particular embodiments of the glucosamine compositions.

With reference to FIG. 2, chitin-containing fungal biomass (a) may first be reacted in a relatively aggressive acidic solution (c). Relatively strong (aggressive) acids may be used to hydrolyze the fungal biomass, including acids of concentrations less than 50 percent. Acids of concentrations of from 5 to 25 percent are also suitable. Suitable strong acids include hydrochloric, sulfuric, phosphoric, and citric acid at appropriate concentrations.

In particular embodiments of the disclosed methods particular glucosamine compositions are formed by an aggressive acid treatment, reacting from 5 to 20 percent acid with from 2 to 50 percent pretreated biomass (based upon dry weight, although the biomass is typically processed with water present) and from 35 to 93 percent water. In certain implementations the reaction mixture comprises from 8 to 12 percent hydrochloric acid, from 4 to 8 percent biomass (based upon dry weight), and from 80 to 90 percent water. In yet another embodiment, the acid solution is from 17 to 20 percent hydrochloric acid solution.

The aggressive acid treatment mixture containing the biomass, acid, and water is heated and maintained at a relatively elevated temperature. The mixture is usually heated to a temperature at or near its boiling point (typically 90° C. to 106° C.) and maintained under reflux conditions for 5 hours or greater, more typically greater than 8 hours, and usually less than 16 hours. The reaction may continue long enough to have a complete breakdown of the chitin, but not so long as to be inefficient or to excessively decompose the glucosamine compositions.

Although reaction in the relatively aggressive acid solution produces a glucosamine composition, subsequent purification steps may be taken. A first purification step may include a separation step, such as filtration, to remove particulate impurities, resulting in a substantially clear solution of the glucosamine composition, (d) in FIG. 2. The solution contains an embodiment of glucosamine composition as well as small quantities of glucose and other components of the composition. The glucosamine composition can be concentrated and some of the acid recovered can be recycled and reused.

The glucosamine composition may be crystallized, (e) in FIG. 2. For example, the glucosamine composition may be crystallized by adding ethanol to the concentrated solution or by continuing evaporation to the glucosamine composition solubility limit.

The glucosamine composition can be recovered by a separation process, such as filtration or centrifugation, followed by drying. The dried glucosamine composition is optionally further treated to remove undesirable residual sugars. One method of removing such sugars is by dissolving the glucosamine composition in water and adding ethanol to again precipitate the glucosamine composition while undesirable sugars remain in solution. Alternatively, the solution can be treated by electrodialysis, chromatography, membrane filtration, or other suitable procedures to further increase the concentration of glucosamine in the glucosamine composition. The glucosamine composition may optionally be decolorized and/or deodorized by, for example, treating the composition with ethanol, carbon, or other suitable material or method.

Such an aggressive acid hydrolysis method typically has a yield of glucosamine composition of greater than 50 percent of the total chitin content of the fungal biomass starting material.

In an alternative embodiment of the method set forth above, the biomass can initially be treated to remove some impurities and/or to improve glucosamine composition production. These treatments can include, for example, heating the biomass, adding digestive enzymes, mixing with an acid or base, mechanical agitation, ultrasonic cell disruption, or dewatering by compression. One optional treatment for removing proteins, lipids, and residual citric acid involves pretreating the biomass in the presence of a base, such as sodium hydroxide ((b) in FIG. 2).

In certain embodiments a concentration of less than 10 percent sodium hydroxide is added to the fungal biomass. The basic solution is heated to a relatively elevated temperature for a period of time sufficient to remove a desirable amount of the non-chitin containing material, such as proteins and lipids. This period of time may be less than two hours. One specific example of this pretreatment method involves heating the fungal biomass to from 100° to 125° C. in a 1 to 8 percent solution of sodium hydroxide for 20 to 60 minutes. Alternatively, the sodium hydroxide concentration may be 1 to 4 percent. Embodiments wherein the biomass is treated with a basic solution, protein and glucans are hydrolyzed in the biomass. These byproducts may optionally be removed by, for example, filtration. The removal of such proteins and other waste products may be followed by treatment to remove soluble proteins, amino acids, and other impurities.

An alternative to treating the biomass with a basic solution could include, for example, treating the fungal biomass in solution with protease enzymes or other suitable enzymes to remove undesirable components such as proteins and lipids. Yet another alternative embodiment comprises mechanically treating the fungal biomass to physically break down the cell walls so that undesirable proteins and lipids within the cells can be removed prior to extracting the chitin from the cell walls themselves. In yet another alternative embodiment, alcohols are used to remove undesirable components from the fungal biomass prior to acid hydrolysis.

In another embodiment of the method for producing glucosamine compositions from fungal biomass, the biomass material may undergo a mild acid pre-treatment followed by an aggressive acid treatment.

Figure 3:
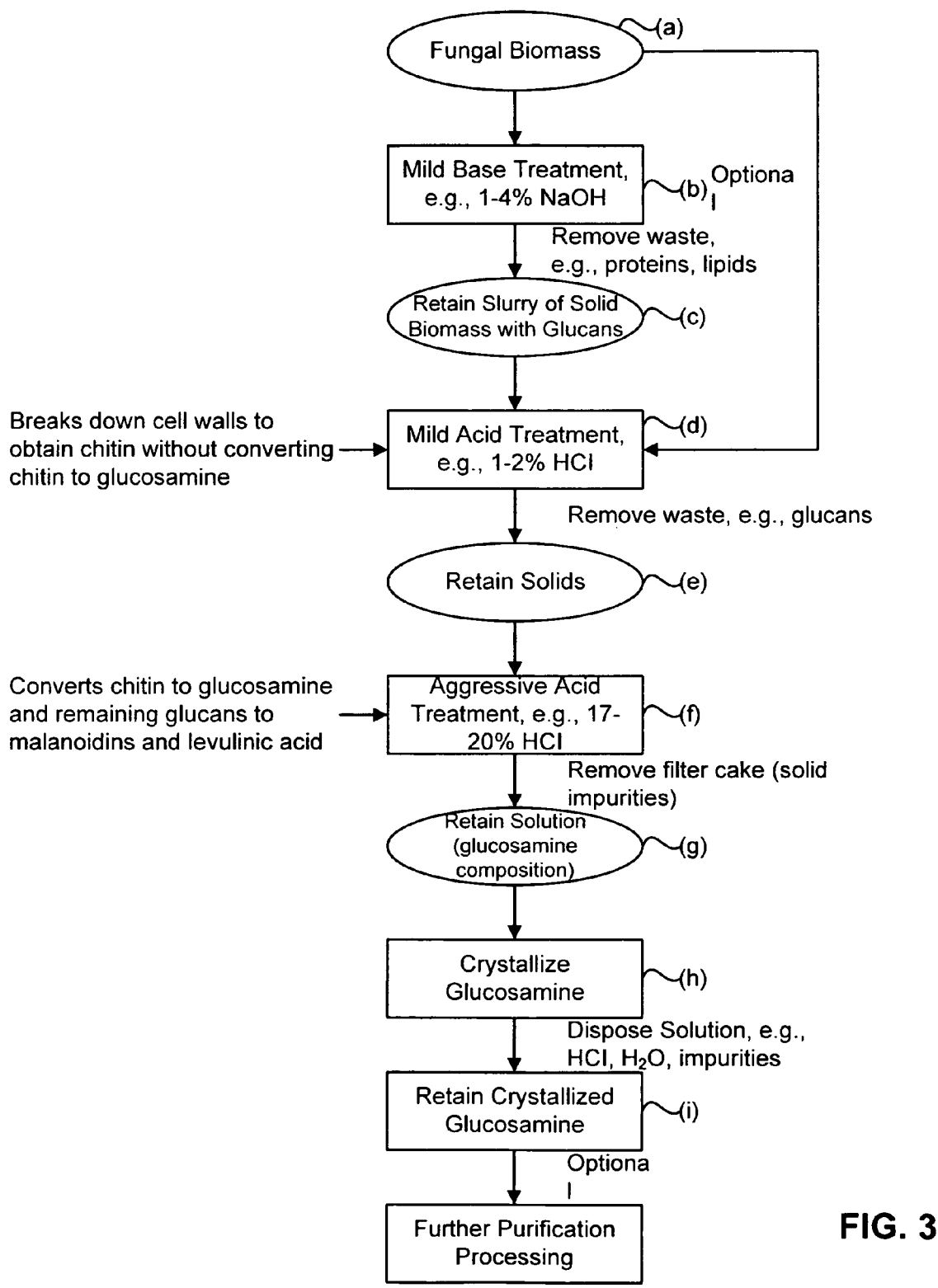
FIG. 3 is a flow diagram of another of the disclosed methods for producing embodiments of the glucosamine compositions.

More specifically, with reference to FIG. 3 chitin-containing biomass (a) may first undergo a mild acid pre-treatment (d). The acid hydrolysis conditions (parameters comprising time, temperature, and acid concentration) used are "mild" in comparison to the subsequent aggressive acid treatment (f). The acid hydrolysis that occurs under the relatively mild conditions allows removal of undesirable constituents from the biomass prior to the aggressive acid treatment (f). A mild acid treatment therefore may be used to improve any one of several aspects of producing the glucosamine composition from fungal biomass. A mild acid can be used to break down the cell walls of the fungal biomass such that extraneous biomass constituents, such as proteins, lipids and undesirable polysaccharides can be removed prior to hydrolyzing the chitin. The acid concentration during mild acid treatment may be from 0.01 to 20% or 0.1 to 15%, or from 0.5 to 5% w/w acid, such as HCl. The mild acid pretreatment may also be carried out using organic acids, such as citric, oxalic, malic, maleic, itaconic, or succinic acids. These organic acids may be used at concentrations ranging from 0.01 to 16 wt % at temperatures between 110° C. to 200° C. for 10 minutes to 15 hours. Lower acid concentrations require longer reaction times, higher temperatures, or both. For example, 0.1% citric acid can be used at a temperature of about 130 to 160° C. for two to six hours. A 15% citric acid solution can be used at temperatures between about 110 and 130° C. for 15 minutes to three hours. Higher concentrations of strong acid solutions or the use of different acids or mixed acids may be used to break down the cell walls more quickly, yet reaction conditions must be adapted to control the undesirable, premature conversion of the chitin to glucosamine. Likewise lower concentrations of strong acids, weak acids or mixed acids may be used (especially at relatively higher temperatures, for longer time periods, or at higher concentrations) such that the cell walls are sufficiently broken down to afford removal of a substantial or desirable portion of the extraneous biomass constituents, e.g., lipids, proteins and undesirable polysaccharides.

A mild acid treatment (d) may be performed by reacting the following components: from 0.05 to 20 percent acid, and from 1 to 50 percent biomass (based upon dry weight). In certain implementations the mild acid reaction mixture comprises from 0.1 to 12 percent hydrochloric acid, and from 3 to 25 percent biomass (based upon dry weight). In yet another embodiment the solution amounts comprise from 0.5 to 5 percent hydrochloric acid and from 5 to 15 percent biomass (based upon dry weight).

The mild acid treatment may be carried out at a temperature of 60° C. to 200° C. or from 100° C. to 165° C., or at a temperature of 125° C. to 145° C. Higher temperatures may be used as long as it is not so high as to convert a significant amount of the chitin to soluble forms. Likewise, lower temperatures (such as 60° C.-90° C.) may be used (especially with relatively concentrated strong acids, such as HCl) as long as the cell walls are sufficiently broken down to release the waste products, e.g., lipids, proteins, and undesirable polysaccharides, without converting a significant amount of chitin to soluble forms. As used herein "a significant amount of chitin to soluble forms" in regard to the described processes means less than an amount that would provide a low yield of glucosamine in the final glucosamine composition, less than 10% of the chitin, or less than 5% of the chitin, or less than 2% of the chitin.

Prior to or following the mild acid treatment, the fungal biomass (a) (or the solids (e) retained after the mild acid treatment (d) removal of the undesirable products) may optionally be treated with a mildly basic solution (b) as described above and as referenced in FIG. 3. Although method steps are shown and described in specific orders, it is to be understood that the order of these steps may be varied without departing from the disclosed methods.

The solids (e) retained after the mild acid treatment (and optionally the mild base treatment (b)) are then treated with an aggressive acid (f) as discussed in the embodiment above. In this embodiment, however, a large portion of the impurities, primarily glucans, have already been removed from the solution (between steps (d) and (e)). Accordingly, the aggressive acid treatment (f) to convert chitin in the remaining solids from the fungal biomass to a glucosamine composition requires significantly less acid. For example, with an aggressive acid treatment under conditions such as 17% HCl and 10% dry biomass solids for 9 hours at 100° C., the hydrochloric acid needed in the aggressive acid step could be reduced by from 20 to 60%.

When a mild acid pretreatment and waste product removal process is performed prior to an aggressive acid treatment, because less acid need be used, the amount of final resulting waste solution (between steps (h) and (i)) is a significantly smaller volume as compared to the method omitting the mild acid pretreatment. The acid needed to treat the biomass is typically expensive; a smaller volume of acid is a significant cost savings, especially when producing the product on a commercial scale. The smaller volume of acidic solution also allows for smaller separation apparatus to separate the glucosamine composition from the acidic solution. Because apparatus needed to separate such a concentrated acid solution must be formed of special (and expensive) materials resistant to the corrosive activities of concentrated acids, smaller separation apparatus saves a significant amount in costs of manufacturing glucosamine compositions from fungal biomass, especially on a commercial scale. When a mild acid pretreatment precedes the aggressive acid treatment the smaller volume of acidic solution results in less waste solution to be treated once the glucosamine composition is removed therefrom.

Glucosamine compositions are formed during the aggressive acid treatment following a mild acid pretreatment in the same manner as compositions formed with aggressive acid treatment alone.

When the chitin in the remaining solid (e) is treated with the aggressive acid (f), glucans not removed in the preceding separation process are converted to beneficial glucosamine composition components, such as melanoidins and levulinic acid. To alter the concentrations of such components of the glucosamine composition, one may allow more of the glucans to remain in the remaining solid (e).

Process steps following the aggressive acid treatment (f) are substantially similar to those discussed above.

In yet another embodiment of the methods for producing glucosamine compositions from fungal biomass, increased temperatures and/or pressures are utilized with an aggressive acid treatment. This allows the reaction to occur using less acid or in a shorter time period than the above-mentioned aggressive acid treatment. Temperature ranges for this the increased temperature, aggressive acid treatment are from 90° C. to 160° C., for example, from 105° C. to 160° C. The pressure may be allowed to build as a function of reactions taking place in a sealed vessel.

More specifically, fungal biomass is treated at the aggressive acid treatment phase with an acid, such as from 4 to 20% acid or from 6 to 13%. The lower concentrations of acid still convert the chitin in solution to glucosamine because the reaction conditions are changed to increase the temperature and/or the pressure parameters. Specifically, the acid/biomass solution is placed in a sealed vessel such that the reaction may take place at pressures of slightly over atmospheric to 10 atmospheres, or slightly over atmospheric to 4 atmospheres, such as at 2 atmospheres. The increased pressures may be due to the reaction taking place at an increased temperature in a sealed vessel or the reaction may take place in a vessel in which the pressure is otherwise made to increase.

The temperature, if elevated, is preferably from 90° C. to 160° C., or 100° C. to 140° C., such as 110° C. to 130° C. The reaction may take place at such elevated temperatures at the pressures set forth above or outside a closed vessel at atmospheric pressure. If the temperature of the reaction takes place at from 90° C. to 160° C. in a closed vessel, the pressures will generally be at atmospheric pressure to 5 atmospheres (65 psig). Good results are obtained with, e.g., a reaction temperature of 120° C. and a pressure of 1 atmosphere (or 15 psig).

Other methods of increasing the temperature are available and included in the methods proposed, for example, increasing the boiling point by adding salts.

The remainder of the increased temperature and/or pressure methods for producing glucosamine compositions from fungal biomass follows those steps outlined in the above-described methods (such as shown in FIG. 2 or 3). Specific examples of the increased temperature and/or pressure methods for producing glucosamine compositions are set forth below.

D. Methods for Producing Fungal Biomass N-acetylglucosamine Compositions or Glucosamine Compositions Also disclosed are methods for making N-acetylglucosamine (NAG) and/or glucosamine compositions from fungal biomass wherein an enzymatic pretreatment step, a separation step and subsequent second enzymatic step are utilized. In addition, disclosed are methods for making N-acetylglucosamine and/or glucosamine compositions from fungal biomass wherein a mild acid pretreatment step (or other pretreatment step), a separation step and subsequent enzymatic step to convert chitin to N-acetylglucosamine are utilized. Further disclosed are methods wherein glucose present in the composition after converting chitin to N-acetylglucosamine is enzymatically treated to convert the glucose to removable ionic forms. Also disclosed are methods wherein the N-acetylglucosamine compositions are deacetylated to form glucosamine compositions.

Fungal biomass typically includes a significant portion (at least 15% and up to about 50% to about 60%) of glucans intermixed with the chitin. In addition, because glucans are not water soluble they are not readily removable from the fungal biomass. In prior methods, such as disclosed in U.S. Pat. No. 6,693,188, enzymes are utilized to degrade glucans in the biomass at the same time as the chitin is degraded by the enzymes to convert the chitin to NAG. Unfortunately, such methods provide a disappointing amount of chitin in the biomass being converted to NAG, in large part because the glucans are still present in the biomass when the available chitin is being converted to N-acetylglucosamine by enzymatic treatment. Such glucans interfere with the availability of chitin for interaction with the enzymes, leaving a large portion of the chitin intact (that is, a large portion of the chitin is not converted to NAG). In addition to the '188 patent method's low percent conversion of chitin in the fungal biomass to NAG, the conversion rate is also relatively slow (about 72 hours is needed to attain maximum conversion of chitin to NAG). Table 3 below shows comparison data for the treatment of biomass with a pretreatment step prior to a conversion step with such a method wherein no pretreatment was performed prior to conversion of the chitin to N-acetylglucosamine.

Table 3 shows a comparison of high NAG yields obtained by enzymatic digestion of chitin from pretreated fungal biomass, versus, low yields and long reaction times in untreated biomass.

TABLE 3

| Treatment | Time (hr) | Solids (g/l) | Theoretical Chitin (g/l) | Theoretical NAG (g/l) | Sample NAG (g/l) | Sample Glc (g/l) | % NAG Liberated |
|---|---|---|---|---|---|---|---|
| 188 Patent | 24 | 17.6 | 3.161 | 3.45 | 0.235 | 0 | 6.8 |
| 188 Patent | 48 | 17.6 | 3.161 | 3.45 | 0.508 | 0 | 14.7 |
| 188 Patent | 72 | 17.6 | 3.161 | 3.45 | 0.65 | 0 | 18.9 |
| mild acid chitinase/cell | 20 | 29.6 | 11.11 | 12.1 | 11.6 | 6.6 | 95.5 |
| Mild acid chitinase | 7 | 25 | 7.5 | 8.18 | 8.24 | 6.37 | 100.7 |

Glc = glucose

The first three listed treatments in Table 3 were performed as described in U.S. Pat. No. 6,693,188. The fourth and fifth treatments utilized the presently disclosed methods using an embodiment of the mild (0.1% citric acid) acid-pretreated biomass. Enzymatic digestion in treatment 4 used a combination of chitinase and cellulase, whereas, the enzymatic digestion in treatment 5 used only chitinase. Treatments 4 and 5 demonstrate rapid conversion of chitin to NAG, as compared to the art described in the '188 patent. Moreover, greater than 95% of the chitin was digested in treatments 4 and 5, indicating greater availability of chitin to enzyme digestion due to biomass pretreatment. The ability of chitinase to bind and rapidly digest chitin in pretreated biomass is further demonstrated in FIG. 10, which shows the relative rate of NAG formation during the conditions used in treatment 4 of Table 3. In this treatment, over 80% of chitin digestion has occurred by 7 hours.

Unexpected superior results were found when the presently disclosed methods were utilized such that the fungal biomass was treated first with an enzyme pretreatment such that a large portion of the glucans were readily removable so as no longer present to compete with the chitin for exposure to and conversion by the enzyme treatment. More specifically, in certain embodiments of the disclosed methods the fungal biomass is first subjected to an enzymatic pretreatment step. The biomass is pretreated not only to release for separation at least a portion of proteins, lipids, and polysaccharides from the biomass but also such that a significant portion of the glucans (about 30% of the glucans present in the biomass or more) are pretreated with enzymes so as to convert the glucans to soluble and thus removable form.

Figure 9:
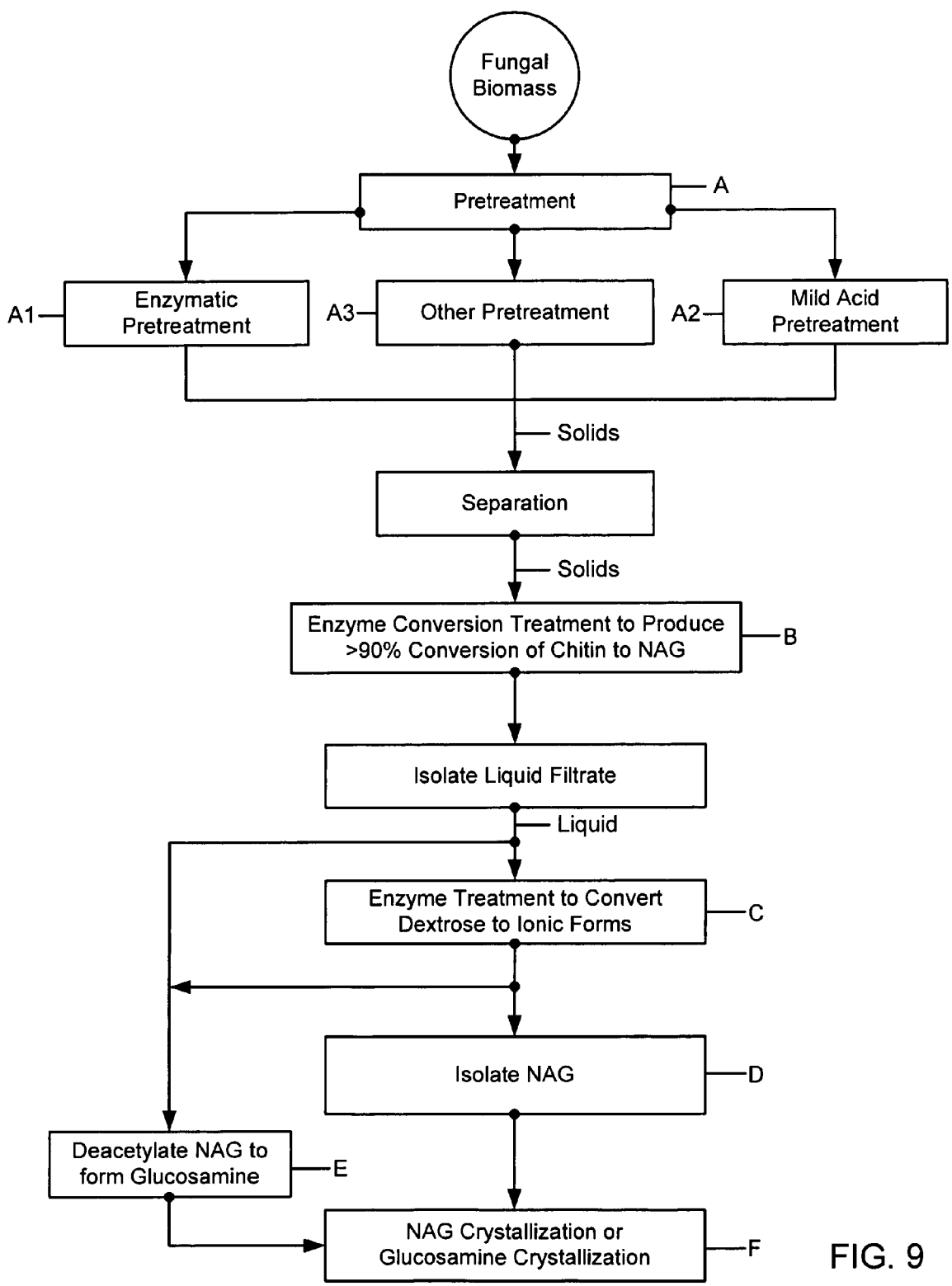
FIG. 9 is a flow diagram of certain of the disclosed methods for producing embodiments of the glucosamine and/or N-acetylglucosamine compositions.
Figure 10:
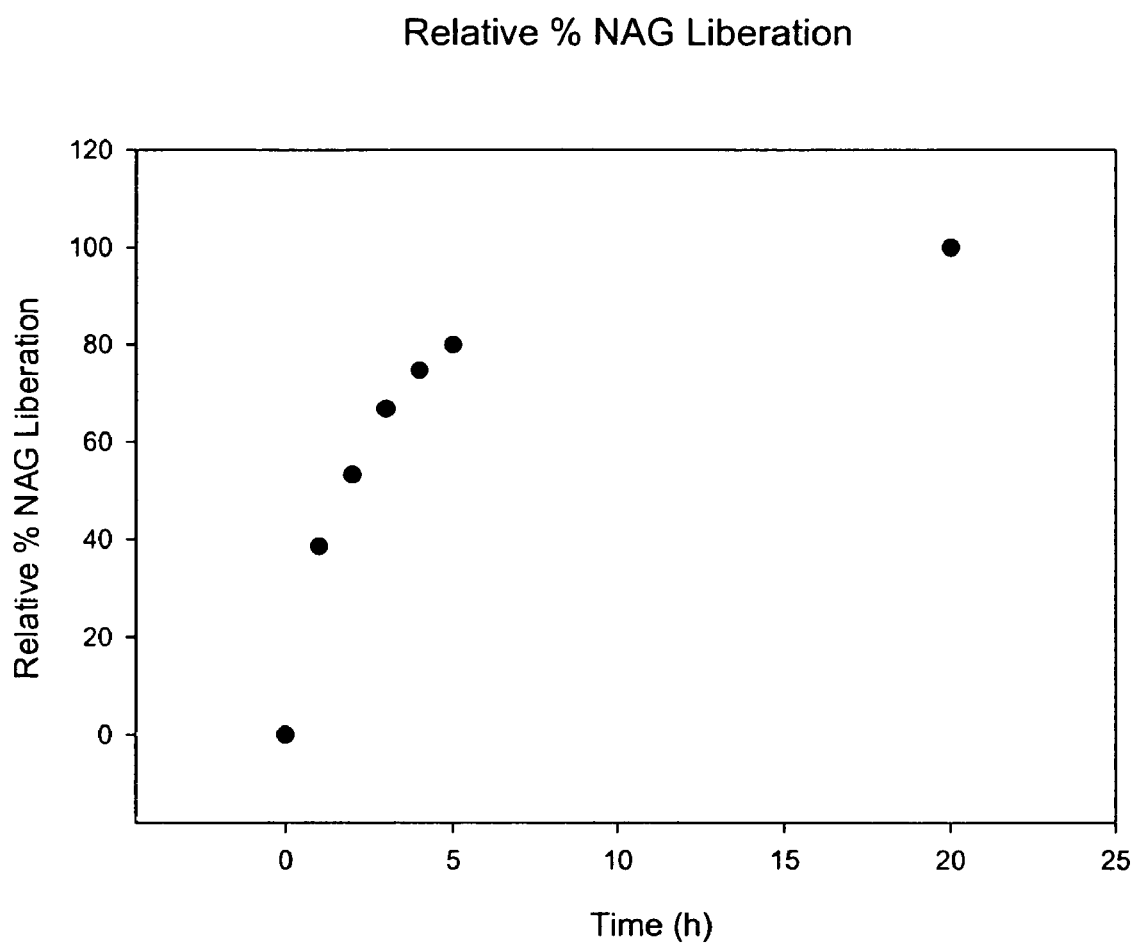
FIG. 10 is a graph illustrating the percent of N-acetylglucosamine obtained over time.
Figure 11:
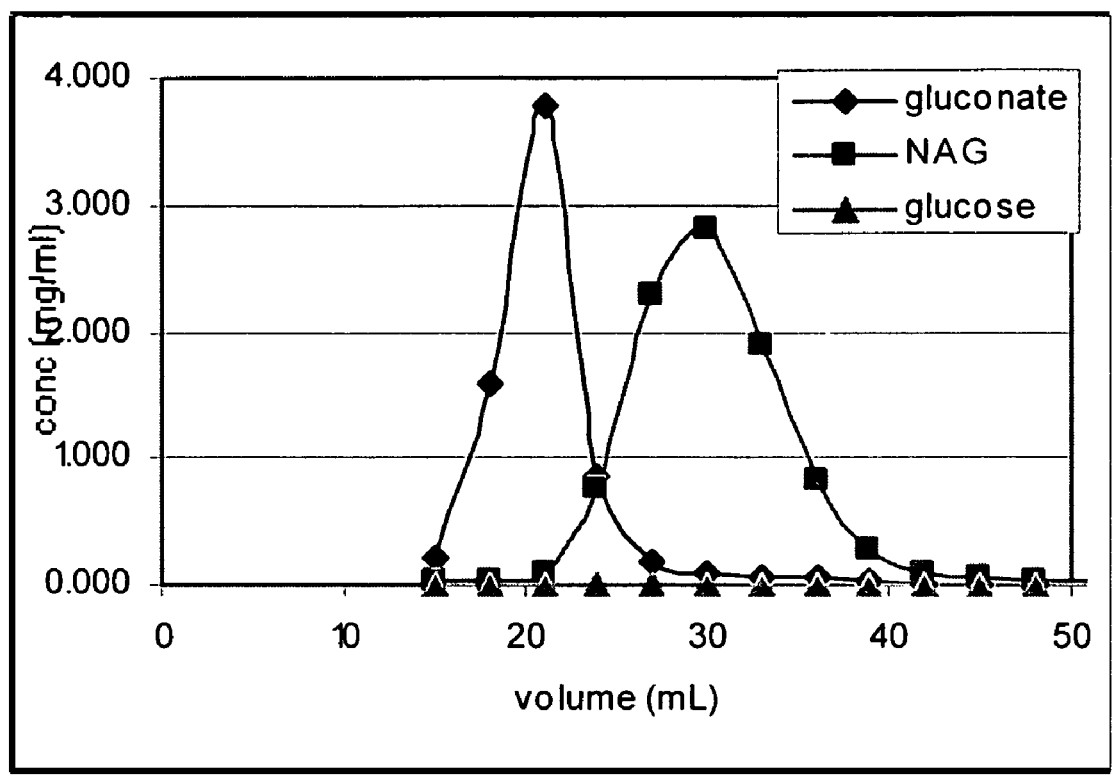
FIG. 11 is an HPLC chromatogram illustrating N-acetylglucosamine separated from other components using a cation exchange resin.

With reference to FIG. 9, the fungal biomass is subjected to a pretreatment step A. Pretreatment step A breaks down the at least a portion of the glucans in the biomass but does not act to convert a significant portion of the chitin to soluble forms, such as to N-acetylglucosamine or glucosamine. As used herein "a significant amount of chitin to soluble forms" in regard to the FIG. 9 described processes means less than an amount that would provide a low yield of glucosamine in the final glucosamine composition, e.g., less than about 30% of the original chitin, or less than 10% of the chitin, or less than 5% of the chitin, are converted to soluble forms. The undesirable glucans and other undesirable components of the biomass are separated from the chitin, for example, by filtration.

More specifically, the pretreatment step A removes at least some of the glucans, proteins, and/or lipids in the fungal biomass source by converting those to soluble forms, which are then separated from the solid fraction, e.g., by filtration, as described below (in certain embodiments, about 30% of the polysaccharides are converted to soluble forms). The remaining solids contain a significantly enhanced concentration of chitin, which in the treatment step converts the chitin to NAG or to glucosamine (described below). If a pretreatment step converted chitin to soluble forms, such as to glucosamine, NAG or oligomers of NAG, these soluble forms would be removed in the separation step between the pretreatment and treatment and result in yield losses. With the pretreatment step A, such as the mild acid pretreatment, e.g., a citric/high temperature method, there is little if any conversion of chitin to a soluble form. Thus, the mild acid pretreatment (discussed below) converts a significant portion of the glucans, polysaccharides, lipids and proteins to soluble forms without converting a significant portion of the chitin to soluble forms.

In pretreatment step A1, the biomass is mixed with enzymes so as to convert a significant portion (at least about 20%) of the glucans present in the biomass to soluble form(s). The enzymes are typically microorganism derived. The enzymes may be introduced to the biomass in the presence of the microorganisms from which they are derived, which has the advantage of avoiding a step of separating the enzymes from their source organisms. Inclusion of the source organisms can be advantageous in implementation where the microorganisms continue to create enzymes after having been added to the fungal biomass.

Suitable enzymes for the pretreatment step (A1 on FIG. 9) include glucanases, laminarases, proteases or cellulases, such as to partially break down fungal biomass cell walls and to convert solid glucans as well as lipids and/or proteins to soluble forms without converting a significant portion of the chitin to soluble forms, such as glucosamine or N-acetylglucosamine. The soluble glucans and other undesirable soluble components of the fungal biomass are then removed by separating (using conventional means such as filtration, centrifugation, decantation, or other reasonable separation methods) the solids from the liquids.

In alternative embodiments other pretreatment steps may be used in combination with or as alternatives to the enzymatic pretreatment step A1. In certain embodiments, the fungal biomass is pretreated with a mild acid pretreatment, see A2. Such a mild acid pretreatment step is described above in relation to the glucosamine composition methods.

Specifically, in certain embodiments, the biomass material may undergo a mild acid pretreatment (A2, FIG. 9) followed by the enzyme treatment (B, FIG. 9). Similar as shown in FIG. 3 for forming a glucosamine composition, in this embodiment for producing N-acetylglucosamine the chitin-containing biomass (a) first undergoes a mild acid pre-treatment (d). The acid pretreatment conditions (parameters comprising time, temperature, acid type, and acid concentration) used are "mild" in comparison to the aggressive acid treatment (f) as used in certain of the glucosamine producing methods. The acid hydrolysis that occurs under the relatively mild conditions allows removal of undesirable constituents from the biomass prior to the enzyme pretreatment A1 or the enzyme treatment B as shown in FIG. 9.

A mild acid can be used to break down the cell walls of the fungal biomass such that proteins, lipids and undesirable polysaccharides can be removed prior to converting the chitin to N-acetylglucosamine through enzyme treatment (B, FIG. 9). The acid concentration during mild acid treatment may be from 0.01 to 20% or 0.05 to 1% w/w acid, such as HCl or one or more organic acids, such as citric acid. Acid percentage ranges vary depend upon the pretreatment temperature and time. Higher concentrations of strong acid solutions or the use of different acids or mixed acids may be used to break down the cell walls more quickly, yet reaction conditions must be adapted to control the undesirable, premature conversion of the chitin to soluble forms. Likewise lower concentrations of strong acids, weak acids or mixed acids may be used (especially at relatively higher temperatures, for longer time periods, or at higher concentrations) such that the cell walls are sufficiently broken down to afford removal of a substantial or desirable portion of the extraneous biomass constituents, e.g., lipids, proteins and undesirable polysaccharides.

A mild acid treatment may be performed by reacting the following components: from 0.01 to 16% citric acid, and from 5 to 30% biomass (based upon dry weight). In certain implementations the mild acid reaction mixture comprises from 0.01 to 3% hydrochloric acid, and from 3 to 25% biomass (based upon dry weight). In yet another embodiment the solution amounts comprise from 0.05 to 5 percent hydrochloric acid and from 5 to 15 percent biomass (based upon dry weight).

The mild acid treatment may be carried out at a temperature of 60° C. to 200° C. or from 70° C. to 105° C., or at a temperature of 80° C. to 120° C. Higher temperatures (e.g., 100-200° C. with an organic acid, such as citric acid) may be used as long as it is not so high as to convert a significant amount of the chitin to soluble forms. Likewise, lower temperatures (such as 60° C.-90° C.) may be used (especially with relatively concentrated strong acids) as long as the cell walls are sufficiently broken down to release the waste products, e.g., lipids, proteins, and undesirable polysaccharides, without converting a significant amount of chitin to soluble forms. As used herein "a significant amount of chitin to soluble forms" means less than an amount that would provide a low yield of N-acetylglucosamine in the final N-acetylglucosamine composition, less than 10% of the chitin, or less than 5% of the chitin, or less than 2% of the chitin.

Prior to, following or instead of the enzyme pretreatment and/or the mild acid pretreatment, the fungal biomass (or the solids retained after the mild acid treatment and removal of the undesirable products) may optionally be treated with a mildly basic solution (A3, FIG. 9) as described above and as referenced in FIG. 3 in relation to the glucosamine composition methods. Although method steps are shown and described in specific orders, it is to be understood that the order of these steps may be varied without departing from the disclosed methods.

For example, in certain embodiments a concentration of less than 10 percent sodium hydroxide is added to the fungal biomass or the solids separated following the pretreatment using enzymes and/or mild acid pre-cook. The basic solution is heated to a relatively elevated temperature for a period of time sufficient to remove a desirable amount of the non-chitin containing material, such as proteins and lipids. This period of time may be less than two hours. One specific example of this pretreatment method involves heating the fungal biomass or separated solids to from 100° to 125° C. in a 1 to 8 percent solution of sodium hydroxide for 20 to 60 minutes. Alternatively, the sodium hydroxide concentration may be 1 to 4 percent. Embodiments wherein the biomass is treated with a basic solution, protein and glucans are hydrolyzed in the biomass. These byproducts are removed by, for example, filtration. The removal of such proteins and other waste products may be followed by treatment to remove soluble proteins, amino acids, and other impurities.

Yet another alternative to treating the biomass with an enzyme pretreatment or a mild acid or basic pretreatment may comprise mechanically and/or ultrasonically pre-treating the fungal biomass to physically break down the cell walls so that undesirable proteins and lipids within the cells can be removed prior to extracting the chitin from the cell walls themselves. Such mechanical treatment could be followed by any of the other disclosed pretreatments, A1-A3, FIG. 9.

Following pretreatment of the fungal biomass the solids are isolated using any suitable separation method, such as filtration, filter pressing, and/or decanter centrifuge. The separated solids are then subjected to the enzyme conversion treatment to convert the chitin to N-acetylglucosamine (B, FIG. 9). Again, the enzymes are typically microorganism derived. The enzymes may be introduced to the pretreated solids in the presence of the microorganisms from which they are derived, which has the advantage of avoiding a step of separating the enzymes from their source organisms. Inclusion of the source organisms can be advantageous in implementation where the microorganisms continue to create enzymes after having been added to the pretreated solids.

Suitable enzymes for the enzyme conversion treatment step (B on FIG. 9) include chitinases, glucanases, cellulases and other enzymes that have specific or non-specific activity that allows them to hydrolyze polymeric or oligomeric forms of chitin and/or glucan, such as laminarase, amylase, glucoamylase, and others. Combinations of enzymes may be used, such as chitinase and cellulase, as demonstrated in Table 4. Under certain reaction conditions, such as varying pH, buffer composition, and temperature, the inclusion of other enzymes, in addition to chitinase, results in more rapid or complete digestion of chitin to NAG.

The enzyme conversion treatment may take place at a temperature of from about 25° C. to about 90° C., or from a temperature of from about 50° C. to about 70° C., or preferably at about 50° C. to about 55° C. Conversion at such relatively high temperatures provides suppression or destruction of micro-contamination of the resulting N-acetylglucosamine composition with contaminants such as most bacteria, fungi, and yeast.

The pH of the enzyme conversion treatment (B, FIG. 9) may be about 3.0 to about 9.0, or from about 4.5 to about 8.0, or from about 5.0 to about 7.5. Buffers useful for practicing the enzyme conversion treatment include, any suitable buffers, such as acetates, phosphates, and citrates. The enzyme conversion treatment provides excellent yield of N-acetylglucosamine at a time period of from about 2 hours to about 24 hours, or from about 4 hours to about 16 hours, or for about 5 hours to about 10 hours.

Using the disclosed enzyme conversion treatment provides a high yield of chitin to N-acetylglucosamine conversion, certain embodiments convert at least about 90% or more of the chitin in the pretreated solids and in certain embodiments at least about 95% or more of the chitin is converted to NAG. (See Table 4.)

Following the enzyme conversion treatment the liquid filtrate is isolated using conventional separation methods such as centrifugation, filtration, etc. The filtrate is then treated to form glucosamine in certain embodiments of the invention (E, FIG. 9). This particular embodiment for forming glucosamine is discussed further below. If the filtrate is not to be treated to form glucosamine from the NAG, then this isolation step can be performed after the enzyme glucose treatment (C, FIG. 9).

The liquid filtrate obtained when the chitin is converted to N-acetylglucosamine also contains a significant amount of glucose (from about 10% to about 100% of the NAG concentration—this amount depending upon the extent and effectiveness of the pretreatment step as illustrated in the Examples below) as well as enzymes, buffers and residual ions from the biomass. Glucose can be separated from the N-acetylglucosamine using chromatographic resins or other similar methods but such separation methods are typically difficult and expensive. The liquid filtrate containing the N-acetylglucosamine and glucose (whether isolated as discussed above or not) in certain embodiments of the disclosed methods is thus treated to a second enzyme treatment to convert glucose to ionic forms of glucose that are more readily separable from the N-acetylglucosamine (C, FIG. 9). The glucose is thus preferably enzymatically treated to convert the glucose to ionic forms (C, FIG. 9), such as gluconic acid using glucose oxidase. The resulting NAG compositions

TABLE 4

NAG from Chitinase and Cellulase

| Treatment | pH | Theoretical NAG (g/l) | HPLC NAG (g/l) | Theoretical glucan(%) | Theoretical Glc (g/l) | HPLC Glc (g/l) | % NAG liberated | % Glc liberated | Undig. Solids (g/l) | Undig. Solids % |
|---|---|---|---|---|---|---|---|---|---|---|
| Cellulase | 4.5 | 10.54 | 1.5 | 0.624 | 17.68 | 5.983 | 14.23% | 33.84% | 18.3 | 70.9% |
| Chitinase/Cell | 4.5 | 9.96 | 7.81 | 0.624 | 16.72 | 6.571 | 78.35% | 39.31% | 9.53 | 39.2% |
| Chitinase | 4.5 | 8.56 | 6.18 | 0.624 | 14.37 | 4.728 | 72.12% | 32.91% | 9.64 | 46.1% |
| Cellulase | 5.5 | 10.54 | 1.04 | 0.624 | 17.68 | 4.649 | 9.85% | 26.29% | 20.05 | 77.9% |
| Chitinase/Cell | 5.5 | 9.96 | 10.52 | 0.624 | 16.72 | 6.773 | 106% | 40.52% | 6.72 | 27.6% |
| Chitinase | 5.5 | 8.56 | 7.00 | 0.624 | 14.37 | 5.47 | 81.71% | 38.08% | 8.06 | 38.5% |
| Cellulase | 6.5 | 10.54 | 0.858 | 0.624 | 17.68 | 3.838 | 8.14% | 21.71% | 21.0 | 81.8% |
| Chitinase/Cell | 6.5 | 9.96 | 10.29 | 0.624 | 16.72 | 6.712 | 103.3% | 40.15% | 6.86 | 28.2% |
| Chitinase | 6.5 | 8.56 | 8.60 | 0.624 | 14.37 | 5.372 | 100.4% | 37.39% | 6.58 | 31.4% |
| Cellulase | 7.5 | 8.56 | 0.835 | 0.624 | 14.37 | 3.71 | 9.75% | 25.82% | 16.3 | 78.1% |
| Chitinase/Cell | 7.5 | 9.96 | 10.05 | 0.624 | 16.72 | 6.786 | 100.8% | 40.59% | 7.10 | 29.2% |
| Chitinase | 7.5 | 10.54 | 9.38 | 0.624 | 17.68 | 5.042 | 89.00% | 28.52% | 11.0 | 42.6% |

Glc = glucose may include some minor amounts of remaining glucose as well as the gluconic acid salt or other ionic species, which are then separable from the neutral N-acetylglucosamine molecules along with the enzymes, buffers and other salts that may be present (see Examples below). Separation methods include ion exchange resins and electrodialysis.

Enzymes suitable for converting the glucose include but are not limited to glucose oxidase, glucose-1-dehydrogenase, and hexokinase.

The enzyme conversion treatment may take place at a temperature of from about 40° C. to about 60° C., or from a temperature of from about 45° C. to about 55° C., or preferably at about 50° C. to about 55° C. Conversion at such relatively high temperatures provides suppression or destruction of micro-contamination of the resulting N-acetylglucosamine composition with contaminants such as most bacteria, fungi, and yeast.

The pH of the enzyme conversion treatment may be about 3.5 to about 7.5, or from about 4.5 to about 7.0, or from about 5.0 to about 6.0. Buffers useful for practicing the enzyme conversion treatment include, any suitable buffers, such as acetates, phosphates, and citrates. The enzyme conversion treatment provides excellent conversion of glucose at a time period of from about 1 hour to about 24 hours, or from about 2 hours to about 16 hours, or for about 5 hours to about 10 hours.

Using the disclosed enzyme conversion treatment provides a high percent conversion of glucose to gluconic acid. Certain embodiments convert at least about 90% or more of the glucose in the liquid filtrate from treatment B and in certain embodiments at least about 95% or more of the glucose is converted to gluconic acid. (See Table 15.)

Alternatively, other methods may be used to separate glucose from the N-acetylglucosamine, such as, the use of chromatographic resins to separate N-acetylglucosamine from glucose, salts, buffers, and enzymes. Typical resins are based on affinities for the functional groups of the molecules. Resins based on polysulfones or with free amino groups are suitable for the separation rather than enzymatic treatment.

In certain embodiments for making N-acetylglucosamine compositions steps B and C (FIG. 9) are conducted simultaneously. That is, in certain embodiments the isolated pretreatment solids are treated with enzymes to convert chitin to N-acetylglucosamine and to convert glucose to ionic forms. Such embodiments include combinations of enzymes including chitinases or chitinases plus helper enzymes (such as glucanases, cellulases, laminarases, or others) that convert chitin to N-acetylglucosamine, together with glucose oxidase or other enzymes that convert glucose to ionic forms such as gluconic acid. Simultaneous running of steps B and C saves in process costs.

The combined enzyme conversion treatments described in steps B and C may take place at a temperature of from about 40° C. to about 60° C., or from a temperature of from about 45° C. to about 55° C., or preferably at about 50° C. to about 55° C. Conversion at such relatively high temperatures provides suppression or destruction of micro-contamination of the resulting N-acetylglucosamine composition with contaminants such as most bacteria, fungi, and yeast.

The pH of the enzyme conversion treatment may be about 3.5 to about 7.5, or from about 4.5 to about 7.0, or from about 5.0 to about 6.0. Buffers useful for practicing the enzyme conversion treatment include, any suitable buffers, such as acetates, phosphates, and citrates. The enzyme conversion treatment provides excellent conversion of chitin to N-acetylglucosamine and excellent conversion of glucose to gluconic acid at a time period of from about 1 hour to about 24 hours, or from about 2 hours to about 16 hours, or from about 5 hours to about 10 hours. (See Table 18)

Using the disclosed enzyme conversion treatment provides a simultaneous high percent conversion of glucose to gluconic acid, and high conversion of chitin to N-acetylglucosamine. (See Table 18)

With reference to FIG. 9, in certain embodiments, after the glucose enzyme conversion treatment (C, FIG. 9), the N-acetylglucosamine in the broth is converted to glucosamine (E, FIG. 9), as discussed below. In embodiments where a N-acetylglucosamine compositions are desired, the N-acetylglucosamine is separated from the broth (the broth containing the ionic forms of glucose and NAG) utilizing anion-exchange resins, such as Purolite PCR-822 (Purolite Co., Philadelphia, Pa.) or Diaion UBK530 (Mitshubishi Chemical Corp., Tokyo, Japan), (See Examples below), or affinity chromatography such as polysulfonic acid resins, etc. (D, FIG. 9), or by membrane filtration or electrodialysis. For ion-exchange resin separation, the pH of the broth is adjusted to a range of from about 5 to about 9 using, for example, sodium hydroxide or potassium hydroxide. Typically, the resins are operated at somewhat elevated temperatures, such as 40-80° C. or, more preferably, 50-60° C., to minimize microbiological contamination. The separated N-acetylglucosamine is then crystallized and dried (F, FIG. 9) using conventional methods such as evaporative crystallization or precipitation with water miscible solvents such as ethanol, isopropanol, or acetone, followed by a drying step such as flash drying, double-drum drying, or vacuum drying. Alternatively, the N-acetylglucosamine can be dried using spray drying or double-drum drying with or without a preliminary evaporation/concentration step. Membrane technology can also be used to remove at least some of the water from the N-acetylglucosamine compositions prior to drying, such as the Koch SR3 nanofiltration membrane. Because the N-acetylglucosamine compositions disclosed herein are formed utilizing enzyme conversion of chitin, unlike conventionally available N-acetylglucosamine compositions, the present compositions are not only kosher (not being formed from shell fish) and are shell-fish allergen free, but also are formed from a natural source. Conventional means for making N-acetylglucosamine include deacetylation and reacetylation processes that require chemical structural changes of the molecules.

In certain embodiments of the disclosed methods the N-acetylglucosamine in the filtrates from steps B and/or C is converted to glucosamine (E, FIG. 9). The N-acetylglucosamine is deacetylated to form glucosamine by, for example, acid hydrolysis or enzymatic deacetylation. The N-acetylglucosamine is converted to glucosamine by adding from about 10-800% molar excess HCL with respect to the N-acetylglucosamine present in the filtrate. For example, a 7 weight % N-acetylglucosamine filtrate would require between about 11 and 80 g HCl per kilogram of filtrate (about 1 to 8 weight %). Higher concentrations of acid yield faster hydrolysis rates and generally require lower hydrolysis temperatures. Other mineral acids, such as sulfuric and phosphoric acid can be used, but their use leads to more difficult purification steps later in the process due to their low volatilities. The HCl filtrate mixture is heated to a temperature of from about 80 to about 100° C. (e.g., about 95° C.) for from about 1 to about 6 hours (e.g., 3 hours). The N-acetylglucosamine can be deacetylated to glucosamine either without prior conversion of glucose or after the glucose enzyme conversion treatment (C, FIG. 9). If the N-acetylglucosamine is converted to glucosamine (E, FIG. 9) without prior conversion of glucose (after B, FIG. 9) then in certain embodiments of the disclosed methods a filter press may be used on the glucosamine composition prior to solidifying the glucosamine (F, FIG. 9). The glucosamine composition can be solidified (F, FIG. 9) by conventional methods such as evaporative crystallization, membrane-dewatering crystallization, evaporation or membrane dewatering followed by precipitation using an organic solvent such as ethanol or isopropanol, drying, freeze-drying, etc.

Forming glucosamine with the above-disclosed methods allows for the production of glucosamine using relatively small amounts of acids at relatively low concentrations (e.g., 3% HCl). More specifically, forming the glucosamine compositions from the N-acetylglucosamine compositions as described utilizes at least about 50% less HCl (or other acid) as compared to methods where the glucosamine is formed directly from the chitin. Lower amounts of acid provide lower costs due to less equipment corrosion and the ability to use certain equipment that is otherwise degraded when higher acid concentrations and amounts are needed. In addition, the glucosamine via N-acetylglucosamine conversion methods reduce safety hazards in the plant where the glucosamine is formed in part due to the lower acid concentrations and because the conversion to glucosamine takes place in acids at lower temperatures below the boiling points of the acids used and/or pressures. The lower amounts of acid and lower concentrations also reduce the amount of hazardous waste chemical that must be disposed.

E. β-glucan Compositions

Glucan can refer to a polymer of glucose in general. There are many types of glucans, which are further defined by the linkage (bonds) between the glucose molecules within the polymer. The glycosidic linkage can be in either an α or β form since glucose exists as two anomers. The β-glucans have been the focus of dietary fiber compositions, cholesterol lowering compositions and other health benefit uses as well as immunostimulants for animal feed, human use and for use with crops. The general formulas vary in the different β-glucan embodiments as to percentage of β-1,3, β-1,4, β-1,6, β-1,3,6, and the ratio of α glycosidic linkages to β glycosidic linkages, as well as chain lengths and molecular weight distributions.

As used herein, β-glucan composition or β-glucans mean, at least in part, a group of polysaccharides (sugars) composed of β-D-glucose monomers linked together by glycosidic bonds including β-1,3, β-1,4 and β-1,6 glycosidic bonds and may include branches comprising β-1,3,6 glycosidic linkages.

Also as used herein, soluble β-glucans means β-glucans soluble in aqueous systems by at least about 20 weight percent. Solubility is defined as the quantity of the β-glucans in the compositions producing stable solutions in aqueous systems, including neutral, acidic or basic solutions, with no visible signs of sedimentation. Solubility is measured by adding a known amount of the β-glucan composition to the solvent in excess of the solubility, then separating the soluble portion from the undissolved solids and measuring the dry solids in the resulting solution. Separation of the undissolved portion can be achieved by centrifugation or simple settling over time due to gravity. Alternatively, small quantities of the β-glucan composition are added to the solvent until dissolution no longer occurs within a reasonable period of time, e.g., one to two hours. The sum of the quantities added that produced a stable solution represents the solubility of the composition.

As used here, a stable solution has no visible or substantially no sedimentation, where solids are settling to the bottom or are at the top of the solution. Significantly or substantially no sedimentation means less than about 5% insoluble matter in a non-purified composition, or for a purified composition, less than about 2% insoluble matter and preferably less than about 1% insoluble matter, in the stable solution. Another manner in which to determine if the solution is a stable solution such that the solution is water soluble as defined herein is when a beam of light, such as that from a laser pointer used for presentations, largely exits a cuvette containing a sample solution with the same vector as the incident, or incoming, beam of light. If most or all of the light is scattered in many directions by the sample, it is not a solution, but a suspension—that is, it is not water soluble as defined herein.

For example, a sample of purified, precipitated β-glucan composition was tested by adding it to water at 5%, 10%, 15%, and 20% by weight. The solutions were mixed using a vortex mixer, then allowed to stand for two hours. At the end of that time, the sediment, if any, was too little to observe with the naked eye. A beam from a red laser pointer (VWR Scientific), transmitted through the solution and appeared on a piece of white paper behind the sample indicating that the light was not significantly scattered in many directions by the sample.

As used herein, fungal β-glucan or β-glucans means a group of fungal polysaccharides (sugars) composed predominately of β-D-glucose monomers linked together by glycosidic bonds including β-1,3, β-1,4 and β-1,6 glycosidic bonds and may include branches comprising β-1,3,6 glycosidic linkages. Soluble fungal β-glucan or β-glucans means a group of fungal polysaccharides (sugars) composed predominately of β-D-glucose monomers linked together by glycosidic bonds including β-1,3, β-1,4 and β-1,6 glycosidic bonds and may include branches comprising β-1,3,6 glycosidic linkages wherein the β-glucans are soluble in aqueous systems by at least about 20 weight percent. Having β-glucans from a fungal derived source is especially useful with the β-glucan composition when used in connection with treating crops. Fungal source β-glucans can be effective in protecting plants from fungal attack, as the β-1,3-glucans from fungal biomass can stimulate an antifungal immune response.

As used herein the term hydrolyze means to cleave bonds in a polymer or compound through the addition of water. Wherein, as used herein, water is not considered to be an acid.

The β-glucan compositions disclosed herein may be in purified or crude form and may be solids or liquids, such as syrups. The β-glucan compositions include aqueous system soluble β-glucans and certain embodiments include water soluble β-glucans. The disclosed soluble β-glucans are from fungal biomass and are in a natural state as chemicals (other than water) are not used in the disclosed processes such that the structure of the β-glucans in the disclosed compositions have minimal overall change to the chemical structure or the forms of the functional groups, such as those caused by oxidizing agents. Soluble β-glucan compositions are especially useful for certain applications. For example, soluble β-glucans are easily transported through the digestive track and are transportable into the circulatory system. In addition, with a soluble, purified β-glucan composition it is much easier to ensure that the dosage of β-glucan given has a measurable active parameter to ensure safety.

In certain embodiments the soluble β-glucans are collections of polysaccharides having an average molecular weight of from about 342 to about 1,000,000. In certain embodiments greater than about 80% by weight of the soluble β-glucans have an average molecular weight of from about 1,000 to about 1,000,000. The average molecular weight depends upon the process conditions, such as temperature, time and acidity, as discussed below. If purified by precipitation, the average molecular weight may also depend upon the ratio of organic solvent to water and temperature. A relatively high molecular weight β-glucan will have a lower solubility in a solvent, so a lower solvent water ratio leads to higher average molecular weight product.

Size Exclusion Chromatography using Dionex Summit Liquid Chromatography system (Dionex, Sunnyvale, Calif.) with TSK-GEL® columns, G4000PWXL, G3000PWXL and G2500PWXL 7.8 mm×30 cm (Tosoh Bioscience, Montgomeryville, Pa.), in series were employed for measurement of soluble 13-glucan molecular weight at 30° C. Water and Pullulan (Shodex, β-82, MW 5,650-710,500, American Polymer Standards, Mentor, Ohio), glucose, maltose, maltotriose, and maltohexose (Sigma, St. Louis, Mo.) were used as eluent and calibration standard. The flow rate was 0.5 mL/minute. The data was processed using Cirrus® GPC software (Polymer Laboratories, Amherst, Mass.).

Certain embodiments of the disclosed soluble β-glucan compositions meet the following criteria (all values are weight percent of dry product):

TABLE 5

| Component | Minimum | Maximum | Range |
| --- | --- | --- | --- |
| Lipids | 0 | 0.5 | 0.01 to 0.1 |
| Protein | 0 | 15 | 3.0-12.0 |
| Ash | 0 | 1 | 0.1-0.5 |
| Carbohydrates | 80 | 100 | 85-98 |
| Dietary Fibers | 80 | 100 | 80-98 |

Certain embodiments of the disclosed soluble fungal β-glucans meet the following criteria

TABLE 6

| Type of Glycosidic linkage | Percentage of total linkages |
| --- | --- |
| 1,3 | 81% |
| 1,4 | 10% |
| 1,6 | 5% |
| 1,3,6 | 3% |
| α/β ratio | 1/8 (89% β) or from about 1/20 to about 1/5 |

Other embodiments of the disclosed soluble fungal β-glucan compositions meet the criteria in Table 7.

TABLE 7

| Composition Characteristic | Range 1 | Range 2 | Range 3 |
| --- | --- | --- | --- |
| % Solubility in Water | 20-70 | 30-60 | 40-50 |
| Average Molecular Weight | 1000-2,000,000 | 2,000-1,000,000 | 5,000-500,000 |
| β-1,3 | 50-90 | 60-90 | 70-85 |

Certain embodiments of the soluble fungal β-glucan compositions disclosed herein were compared to non-fungal β-glucans to confirm the understanding that fungal β-glucans contain a large percent by weight β-1,3-glucan. Specifically, soluble fungal β-glucan of the present disclosure formed using methods as disclosed herein to isolate β-glucans from an *A. niger* source were compared to barley glucans with results as shown below in Table 8.

TABLE 8

| Glucan Source Characteristic | *A. niger* 80%-1,3 linkage and slightly branched (3%) | Barley Unbranched chain with single β-1,3 linked cellotriosyl and cellotetraosyl units arranged randomly |
| --- | --- | --- |
| -1,3 | 81% | 30% |
| -1,4 | 10% | 70% |
| -1,6 | 5% | None |
| -1,3,6 | 3% | None |
| % β linkages | 89% | 100% |
| Molecular Weight Range | 342 to 5500 × $10^3$ | 9000 to 5400 × $10^3$ |
| Solubility | 40-45% (r.t.) | N/A |

Certain of the β-glucan compositions are useful as dietary fiber constituents. Dietary fiber is not digested before reaching the colon, i.e., the portion of polysaccharides not digested in the small intestine is considered dietary fiber. The digestibility is a key measure of dietary fiber. Digestibility measures the fraction of the glucans that are broken down to glucose before reaching the colon. Certain embodiments of the fungal β-glucans include glucans wherein 79-87 weight % of the glucans are not digestible in the small intestine, and are thus considered dietary fiber.

To determine digestibility of the β-glucan compositions, an in vitro digestibility assay as follows was used. The test determines the fraction of digestible fiber in a sample by exposing the sample to reconstituted rat intestinal powder. This material contains all the contents of the rat intestine including the intestinal enzymes. Indigestible fiber is considered dietary fiber. First, 2 ml of a 2% β-glucan solution was mixed with 0.1 g of rat intestinal powder (Sigma, I1630, St. Louis, Mo.), 20 μL of 5% $NaN_3$, 0.5 ml of 20 mM phosphate buffer, pH 6.5, and 1.48 ml of water. The reaction mixture was incubated at 37° C. with slight shaking. A 0.5 ml fraction of the samples were taken at time 0 and 4 hr with a graduated disposable pipet after thorough mixing, and mixed with 1 ml of 1.0 N HCl to stop further enzyme activities. The reaction mixture was filtered using a syringe filter. The glucose content was determined by HPLC using a Varian MetaCarb H Plus column, 300×7.8 mm (Varian, Walnut Creek, Calif.). The mobile phase was 0.01 N $H_2SO_4$ and the flow rate was 0.4 mL/min. Refractive index detector was used as the detector.

The digestibility was calculated as follows:

$$Glc(\%)_{Sample} = [C_{Standard} \times (PA_{Sample}/PA_{Standard}) \times 1.5\ mL \times D] \times 100/C_{Sample}$$

Where:

Glc $(\%)_{Sample}$ = glucose % by weight in the sample $C_{Standard}$ = conc. of the standard in mg/mL $PA_{Sample}$ = peak area of the sample $PA_{Standard}$ = peak area of the standard D = dilution factor, 6

$C_{Sample}$ = conc. of the sample in mg/10 mL $$Digestibility = [Glc(\%)_{4hr} - Glc(\%)_{0hr}]/(1 - Glc(\%)_{0hr})$$

TABLE 9

| Sample | Digestibility (%) |
|---|---|
| Fungal β-Glucan 1 | 13.09 |
| Fungal β-Glucan 2 | 7.96 |
| Barley Beta Fiber | 10.98 |
| FiberSol 2H | 18.83 |

Barley beta fiber was obtained from Cargill Health & Food Technologies (Excelsior, Minn.). FiberSol 2H, Matsutani Chemical (Japan).

Purity as defined herein refers to the percentage of the β-glucan composition susceptible to depolymerization by specific enzymes. A purity test serves two functions, in that it reports the percentage of the composition susceptible to the enzyme(s) used, and it serves to illustrate the differences between glucan compositions.

Purity of certain embodiments of the disclosed fungal β-glucan compositions were determined using an enzymatic test that determines the fraction converted to glucose by specific enzymes. This test arose on the basis that glucans can be complex mixtures of different biopolymers, so the test determines the "purity" of the particular glucan structure susceptible to the specific enzymes in the test kit. Enzymes comprising lichenase and β-glucosidase, obtainable from Megazyme International Ireland Limited (Bray, Co. of Wicklow, Ireland), are designed to measure the "purity" of glucans derived from grains, such as oats or barley. These enzymes are highly origin specific. That is to say grain-originated glucans require grain-originated enzyme system and fungal glucans require fungal enzyme systems. Different enzyme systems require different conditions such as temperature, pH, buffer system for optimal activities. The grain enzymes do not affect significantly the glucans from fungal biomass such as *A. niger*. If an enzyme, such as Genencor β-glucanase 750L available from Genencor, Rochester, N.Y., is utilized, certain embodiments of the disclosed fungal β-glucan compositions have a glucan purity of from about 60% to as high as 100% by weight, depending on test conditions, certain fungal biomass glucan compositions have a 100% by weight glucan purity. The specificity of the enzymes required to break down the glucans differentiates the structures of glucans from various sources.

TABLE 10

Glucan Purity Results Utilizing Different Enzyme Systems

| | Purity (weight %) | | |
|---|---|---|---|
| Sample | MegaZyme Test Kit[1] | Sigma *A. niger* β-Glucanase[2] | Genencor β-Glucanase[3] |
| Barley Flour[4] | 4.08 | Not tested | Not tested |
| Fungal Glucan 1[5] | 36.45 | 19.54 | 89.17 |
| Fungal Glucan 2[5] | 12.49 | 21.91 | 90.50 |

[1]MegaZyme Test Kit comprising enzymes lichenase and β-glucosidase the procedure provided by the manufacturer was strictly followed to test the glucan purity of a barley flour standard (provided by the manufacturer, MegaZyme International, Ireland) and glucans isolated from fungal biomass. The end product, glucose percentage was determined by an HPLC method.
[2]Sigma *A. niger* β-glucanase (available from Sigma, #49101, St. Louis, MO) was used in excess enzyme capacity at the optimal condition: 50 mM sodium acetate buffer, pH 5.0, 37° C. for 1 hour.
[3]Genencor β-glucanase 750L (102-03338-001, Genencor, Rochester, NY) was used in excess enzyme capacity at pH 4.0, at 60° C. for 17 hours.
[4]Barley flour standard was provided by the test kit manufacturer (MegaZyme International, Ireland). The reported β-glucan content is 4.19% by weight.
[5]Two batches of β-glucans were prepared in-house (see Example G3).

There is no one universal enzymatic method to determine the purity of all different kinds of glucans. Therefore the purity of glucan is dependent on the enzyme system and its reaction condition used for determination. Thus, disclosed is the specific test method used to determine purity of the disclosed glucan compositions.

Embodiments of the soluble fungal β-glucan compositions were analyzed for purity levels as follows. An amount of 20 mg of the β-glucan composition was dissolved in 25 mL of water. A fraction comprising 0.1 mL of the sample was transferred into a 16×100 mm test tube having a Teflon-lined screw cap. A fraction of 1 mL of enzyme solution was mixed with the sample. The mixture was then incubated at 60° C. in a water bath for 17 hours. At the end of the incubation, 3.9 mL of water was added. The reaction mixture was filtered and the glucose content was measured using a Dionex HPLC consisting of a Model LC25 column oven, GP50 gradient pump, ED40 electrochemical detector, AS40 autosampler, and EG40 eluent generator with PAD (pulsed amperometric detector).

For each sample a sample blank was prepared by adding 1 mL of water instead of 1 mL of enzyme solution.

The β-glucan composition purity was calculated as follows:

$$Purity(\%) = C_{Std} \times [(PA_{Sample} - PA_{Sample\ Blank})/PA_{Std}] \times 50 \times 25\ mL \times (162/180)/W_{Sample}$$

F. Methods for Producing Fungal β-glucan Compositions

Figure 12:
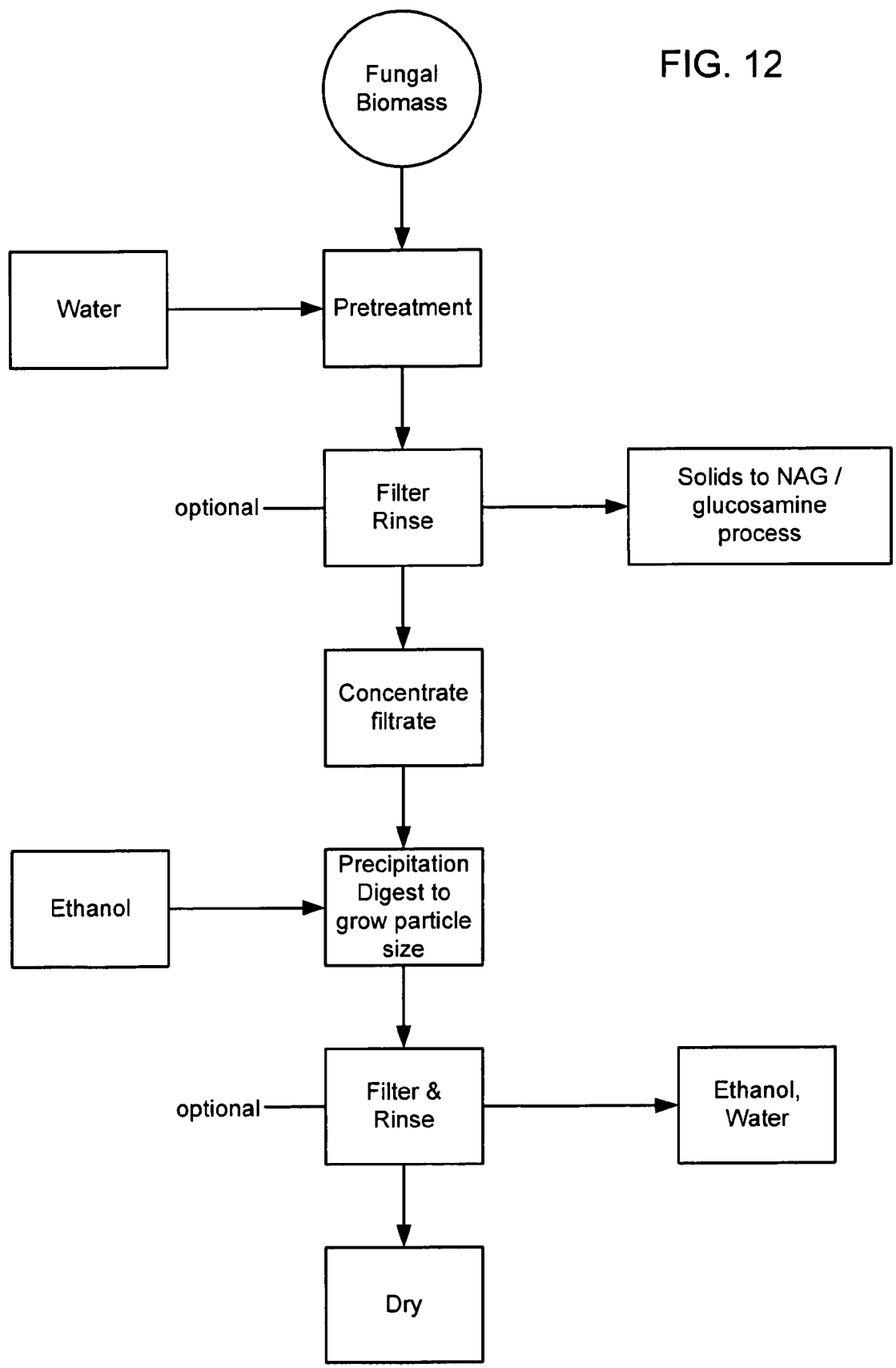
FIG. 12 is a flow diagram of certain of the disclosed methods for producing embodiments of purified, dry β-glucan compositions.

Also disclosed are methods for making soluble β-glucan compositions from fungal biomass. With reference to FIG. 12, the fungal biomass is chosen as discussed above. In certain embodiments the biomass is typically composed of about 60-65 weight % glucan, 18-22% chitin and proteins, lipids, mannans, and galactans. The biomass starting material may be *A. niger* which may have been first used to produce citric acid (thus there may be residual citric acid in the starting material) and may then have been used to produce glucosamine and/or N-acetylglucosamine. Thus, the soluble glucan compositions may be formed as a by-product of any or all of these other methods and products.

Water is added to the biomass to obtain an about 5-18% or 8-14% solids mixture. (The biomass may contain certain acids, depending on the source of the biomass or certain acids could be added, such as polycarboxylic acids, e.g., citric acid, oxalic acid, maleic acid, itaconic acid, succinic acid or mixtures thereof.) In some embodiments water is added to obtain between about 9-13% solids in the mixture. The mixture is then put into a precook tank and may be agitated gently (low shear) as well as heated to above the boiling point of water, e.g., about 110° C. or such as from about 110° to about 200° C. for 10 minutes to about 15 hours, or 1-8 hours or for several hours such as from about 4 to about 6 hours. This step is performed to solubilize the β-glucans—in other words, the starting material glucans in the fungal biomass are insoluble prior to this treatment and are soluble at about 20 to 70 wt % after this treatment step. The time, temperature and citric acid content of the starting material are intertwined parameters. So, if there is a higher citric acid content then the time and temperature can both be lowered and the β-glucans still solubilized. In a preferred embodiment the mixture is heated and gently agitated for 4-6 hours when the starting material includes about 0.4% citric acid.

The mixture is then cooled for to less than 80° C. The product is filtered and in preferred embodiments it is rinsed to increase the recovery of soluble glucans and decrease the saccharide loading (for portions that will be used to form glucosamine and/or N-acetylglucosamine products. The separation is alternatively performed using other separations methods such as a decanter centrifuge, filter press, vacuum filter, or rotary drum filter. The rinse is typically an aqueous rinse.

The filtrate is then concentrated using, e.g., membrane filtration (increases solids and allows selection of molecular weight range of the product). Other concentration methods can be used, such as thermal evaporation with vacuum, infrared drying, drum drying, spray drying from about 2-10 DS to about 40-50 DS, where DS is the total percent dry solids in the solution.

The product is then precipitated using ethanol (or any water miscible solvent, such as isopropanol, n-propanol, acetone, or acetonitrile). The ratio of solvent to water can range from about 1:2 to about 6:1, depending on the solvent used and the desired molecular weight range of the β-glucan composition. The mixture is allowed to digest for 15 minutes to about four hours to increase the average particle size of the precipitate and reduce the inclusion of impurities. There are typically impurities present such as glucose, salts and other impurities from the biomass such that concentration and precipitation leaves certain of these impurities in solution, while the desired β-glucan composition becomes insoluble. In certain embodiments the precipitation is unneeded if membrane filtration was utilized as that would remove the impurities. So certain embodiments after evaporating the material with membrane filtration the ethanol precipitation step may be avoided and the product simply dried. The membrane filtration can be utilized to select desired average molecular weight ranges for the soluble glucans by selecting membranes of appropriate pore size. Membrane filters are specified in large part by their MWCO (molecular weight cutoff). Using a membrane filter with a MWCO of 2000 would remove most salts, monosaccharides, and small oligomers having molecular weights of less than about 2000. Membrane filters with MWCO of for example, 5,000, 20,000, or 100,000 can be used separately or in series to provide β-glucan compositions of desired molecular weight ranges and with most impurities removed.

The product is optionally filtered and rinsed again as discussed above. The undesirable filtrate typically includes ethanol, water, glucose and other impurities such as small oligomers, etc. that did not precipitate when the ethanol was added (as shown in FIG. 12).

The product is then dried by flash drying, vacuum drying, freeze drying, infrared drying, double-drum drying, spray drying and other drying methods known to those of ordinary skill in the art. Preferably the moisture is reduced to about 20 weight percent or less.

Figure 13:
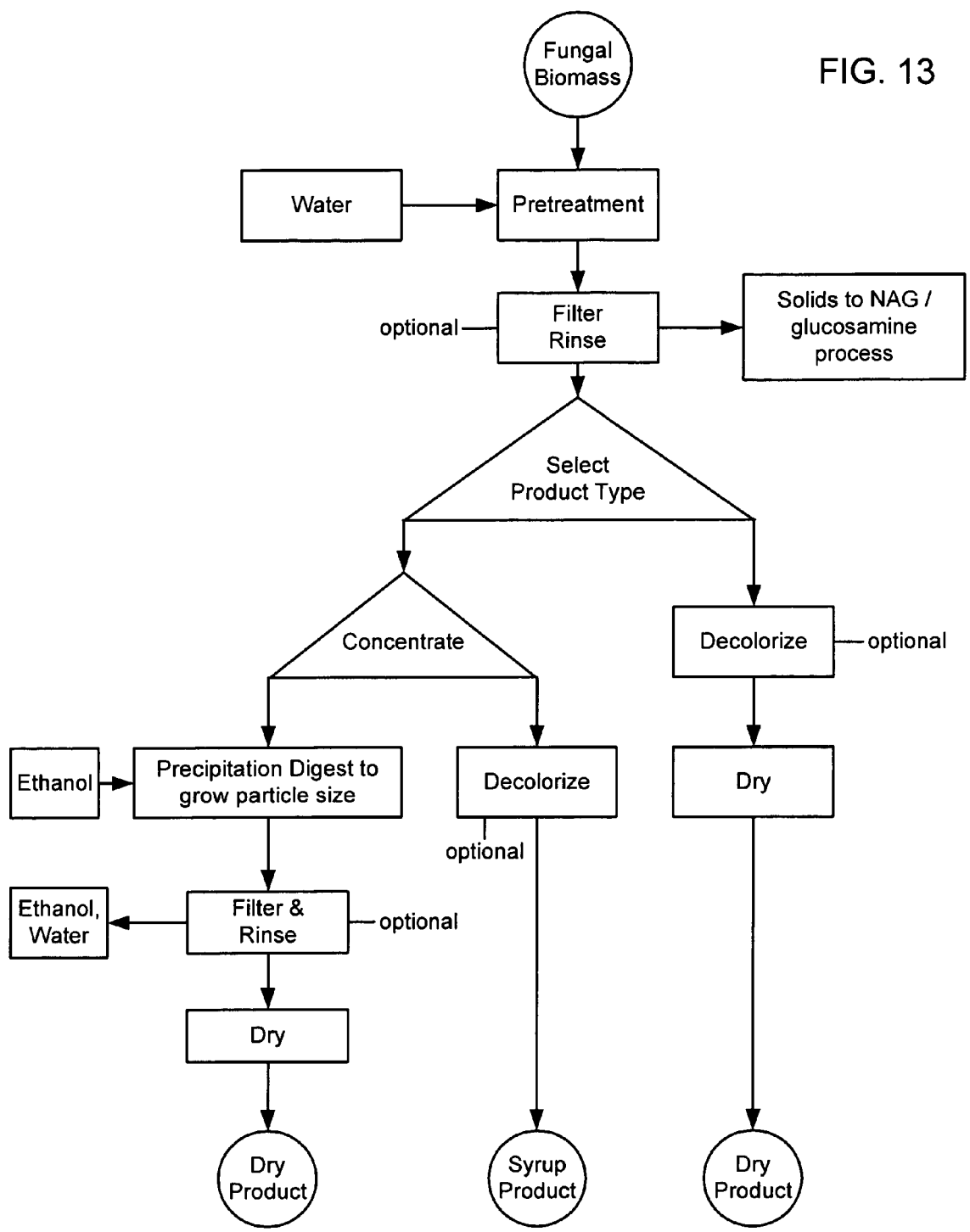
FIG. 13 is a flow diagram of certain of the disclosed methods for producing embodiments of purified or non-purified, liquid or solid β-glucan compositions.

With reference to FIG. 13, the product may be de-colorized by methods available to those of ordinary skill, e.g., resin treatments, through use of activated carbon, decolorizing resins, or other known methods to whiten the β-glucan composition. Products for cosmetics or human consumption may prefer a higher purity, lower color. The de-colorized product is then dried using tray drying, flash drying, freeze drying, vacuum drying, spray drying, fluidized bed drying, or other known methods. The drying is preferably carried out at temperatures less than about 95° C. or such temperatures as might cause color formation, so as to avoid colorizing the de-colorized product. As shown in FIG. 13, optionally a syrup may be obtained by not drying the product. The syrup is typically a low viscosity (e.g., 26 centipose). The syrup is an aqueous solution of β-glucan with from about 10 to about 50% solids by weight at room temperature.

G. Examples

The invention will be further explained by the following non-limiting illustrative examples. Unless otherwise indicated, all amounts are expressed in parts by weight.

Example 1

Fungal biomass was pretreated with a 4 percent aqueous sodium hydroxide (NaOH) solution in an autoclave at 120° C. for 1 hour. This step removed excess proteins and other undesirable materials. The biomass was then thoroughly washed with de-ionized water until its pH was approximately 7.0. This washed material was mixed with concentrated hydrochloric acid (HCl) and water to form a mixture of 10 to 15 percent HCl and 5 to 6 percent biomass, based upon dry weight of the biomass. This mixture was heated at reflux. Samples were taken from time to time, and the reaction analyzed with a high-pressure liquid chromatograph available from Dionex HPLC under the trade designation "DX-500".

Figure 4:
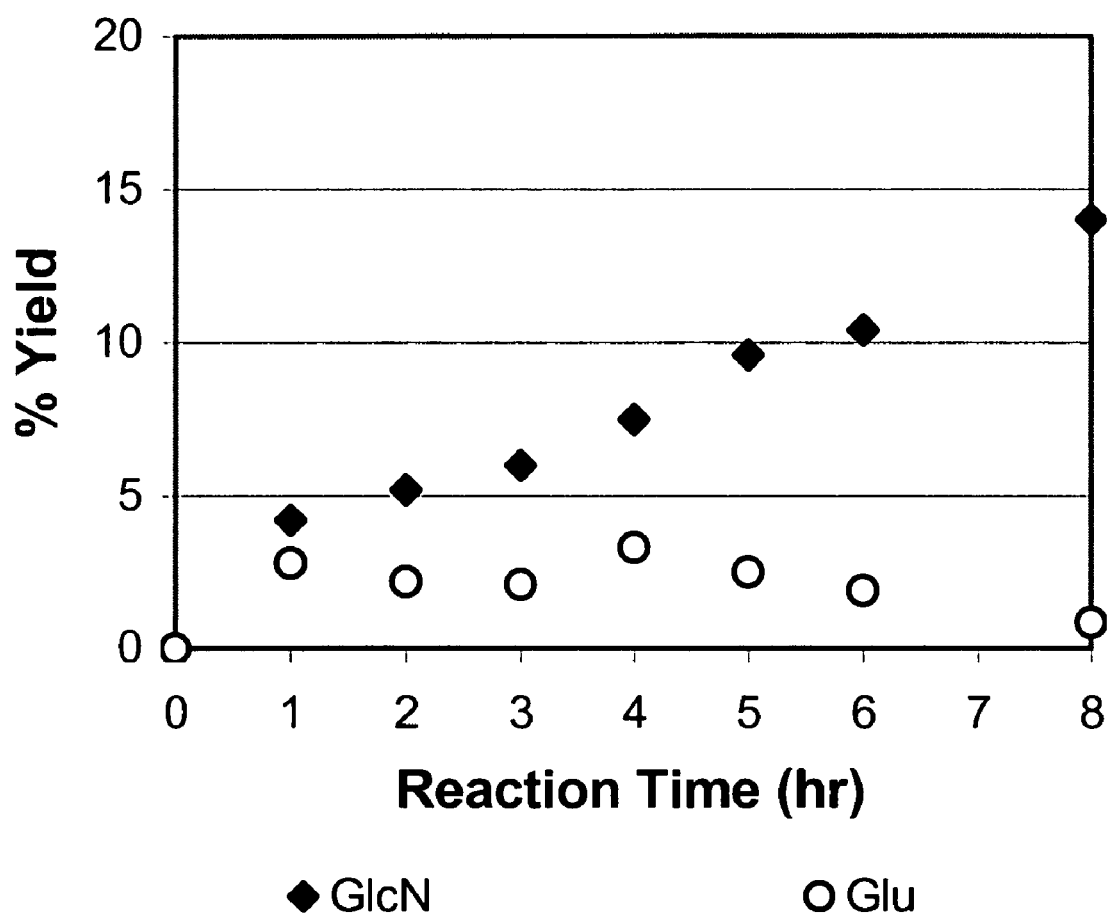
FIG. 4 is chart showing the percent yield of glucosamine in an embodiment of the disclosed glucosamine composition produced using an embodiment of the glucosamine composition methods.
Figure 5:
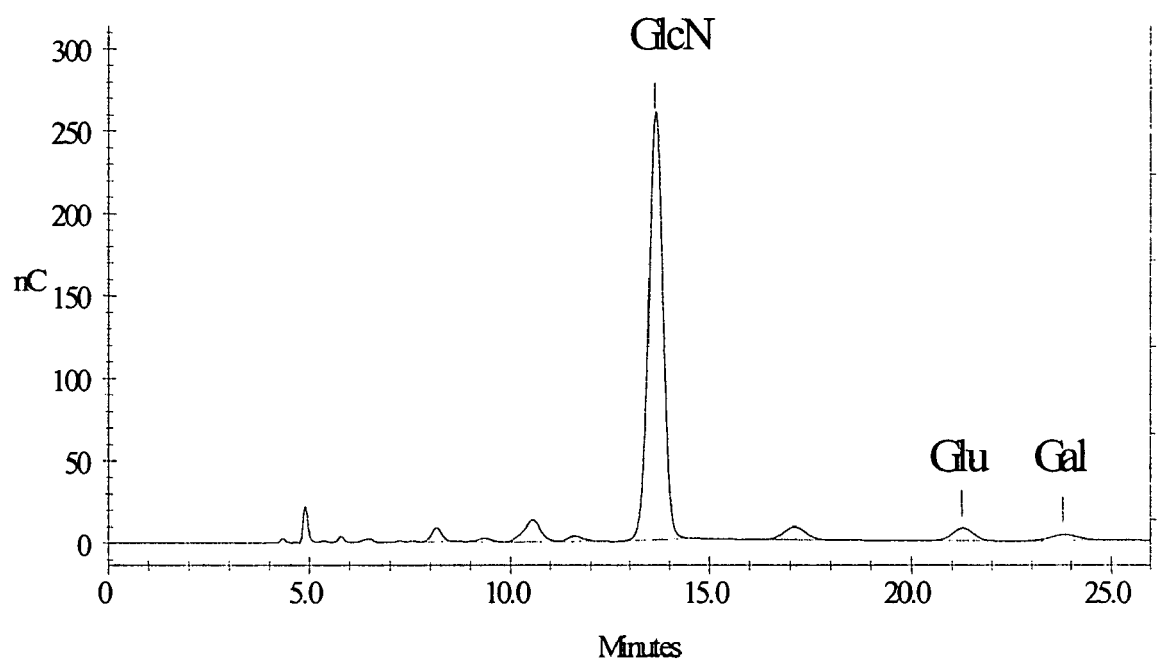
FIG. 5 is a liquid chromatogram of an embodiment of the disclosed glucosamine compositions.

The results are provided in FIG. 4, which shows a chart indicating glucosamine production, and shows that the glucosamine was increasingly produced as the reaction ran through 8 hours, but that the amount of glucose diminished after 4 hours. After 8 hours the glucosamine produced in the yield of 14 percent. A chromatogram of the product is shown in FIG. 5.

Figure 6:
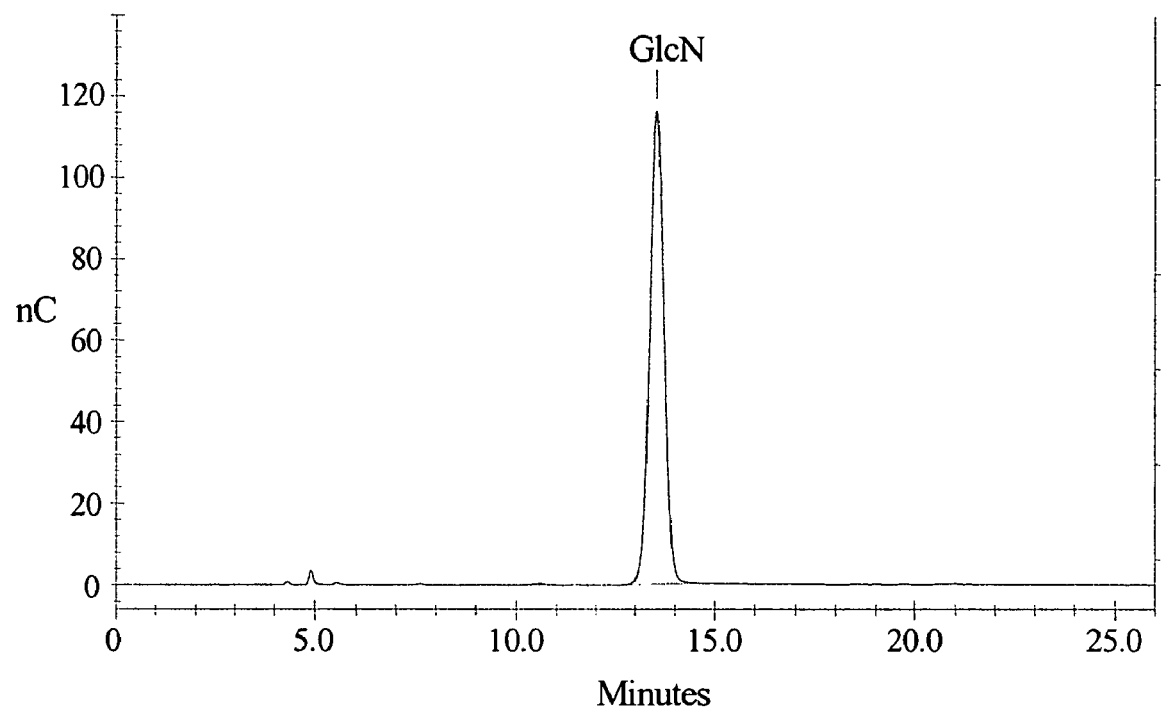
FIG. 6 is a liquid chromatogram of an embodiment of the disclosed glucosamine compositions.

Following reaction, the mixture was filtered, and the filtrate evaporated using a rotating evaporator manufactured by RotaVap to increase the glucosamine concentration of the solution. The final volume was reduced to 10 to 20 ml. To this solution was added 20 ml of ethanol and the solution swirled to promote precipitation of glucosamine and enhance yield. These glucosamine precipitates were obtained by filtration and were further washed with alcohol until the color became white. FIG. 6 shows a chromatogram of the product, indicating greater than 97 percent glucosamine in the glucosamine composition.

Example 2

Example 1 was repeated, but the pretreated biomass was maintained under reflux conditions for 13 hours. The resulting glucosamine composition contained greater than 98 percent glucosamine.

The foregoing detailed description and examples have been given for clarity of understanding only. No unnecessary limitations are to be understood from this description or examples. The invention is not limited to the exact details shown and described, for variations will be included within the invention defined by the claims.

Example 3

Filtered biomass (3900 g) from a citric acid production process was combined with 100 mL concentrated hydrochloric acid and 4.5 L water. The resulting solution (0.5% HCl, 7.8% biomass solids) was maintained at 90-100° C. for 2 hours. The reaction mixture (71.9 g) was filtered and washed with 5 portions of water at 60-70° C. for a total of 400 mL wash. The washed biomass solids weighed 31.5 g and were found to contain 12.5% solids upon drying. The washed biomass solids therefore contained 3.9 g solids out of 71.9 g, or 5.4% solids after mild acid treatment as described above. When compared to the initial 7.8% solids prior to the mild acid treatment a 31% reduction in biomass solids was calculated.

To estimate the amount of the desirable component of the filtered biomass (chitin) sacrificed during the mild acid treatment an aggressive acid treatment was conducted using both pretreated and non-pretreated biomass to produce glucosamine hydrochloride in the following manner:

Dried (pretreated or non-pretreated) biomass (0.40 g) was combined with 3.60 g of 22.5% hydrochloric acid in a small test tube. The resulting solutions (20% HCl, 10.0% biomass solids) were held at 105° C. for 2.5 hours in a heat block. Dionex HPLC analysis of the two acid hydrolyzed samples allowed the percent glucosamine hydrochloride by weight to be determined and compared. Specifically, the amount of free glucosamine was determined using high performance anion-exchange chromatography with pulsed amperometric detection (HPAEC-PAD). The system consisted of an EG40 eluent generator, GP50 gradient pump, AS40 autosampler, LC25 column oven, and ED40 electrochemical detector, all produced by Dionex Corporation, Sunnyvale, Calif., U.S.A. The method was adapted from Dionex Corporation Technical Note 40, incorporated herein by reference. A Dionex Carbo-Pac PA-20 column was used rather than a PA-10 column. The eluent was 8 mM KOH at 0.5 mL/min. The column and detector were maintained at 30° C. The injection volume was 10 µL. The standard was glucosamine hydrochloride at 10.8 mg/L. Samples were diluted with deionized water, ASTM Type II, and filtered through 0.2 µm vial filters in an autosampler. Multiple standards were analyzed before and after each sample set.

The non-pretreated biomass sample contained 2.1% glucosamine hydrochloride. The maximum theoretical amount of glucosamine hydrochloride attainable from the pretreated biomass is 3.0% (assumes all 31% reduction in biomass solids is non-chitin). The pretreated biomass sample was measured at 2.7% glucosamine hydrochloride by weight. Thus, mild acid pretreatment resulted in a 29% chitin-enrichment of the biomass solids, yet reduced the yield of glucosamine hydrochloride from the original biomass by 10%.

Example 4

Filtered biomass (3900 g) from a citric acid production process was combined with 100 mL concentrated hydrochloric acid and 4.5 L water. The resulting solution (0.5% HCl, 7.8% biomass solids) was held at 90-100° C. for 20 hours. The reaction mixture (95.2 g) was filtered and washed with 5 portions of water at 54-70° C. for a total of 320 mL wash. The washed biomass solids weighed 26.9 g and were found to contain 16.0% solids upon drying. The washed biomass solids therefore contained 4.3 g solids out of 95.2 g, or 4.5% solids after a mild acid treatment as described above. When compared to the initial 7.8% solids prior to the mild acid treatment one can calculate a 42% reduction in biomass solids was obtained.

To estimate the amount of the desirable component of the filtered biomass (chitin) sacrificed during the mild acid treatment, an aggressive acid treatment was conducted using both pretreated and non-pretreated biomass to produce glucosamine hydrochloride in the following manner:

Dried (pretreated or non-pretreated) biomass (0.40 g) was combined with 3.60 g of 22.5% hydrochloric acid in a small test tube. The resulting solutions (20% HCl, 10.0% biomass solids) were held at 105° C. for 2.5 hours in a heat block. Dionex HPLC analysis (performed as described in Example 4) of the two acid hydrolyzed samples allowed the percent glucosamine hydrochloride by weight to be determined and compared. The non-pretreated biomass sample contained 2.1% glucosamine hydrochloride. The maximum theoretical amount of glucosamine hydrochloride attainable from the pretreated biomass is 3.6% (assuming all 42% reduction in biomass solids is non-chitin). The pretreated biomass sample was measured at 3.0% glucosamine hydrochloride by weight. Thus, mild acid pretreatment resulted in a 43% chitin-enrichment of the biomass solids yet reduced the yield of glucosamine hydrochloride from the original biomass by 17%.

Example 5

Filtered biomass (2000 g) from a citric acid production process was combined with 3000 g of a 7.5% hydrochloric acid solution. The resulting solution (4.5% HCl, 6.0% biomass solids) was held at 90-100° C. for 2 hours. A portion (40.7 g) of the reaction mixture was transferred to a 50 mL centrifuge tube. The sample was centrifuged and the liquor was decanted. The remaining solids were subsequently washed five times with 25-30 mL portions of NaOH solution (pH 13.1) then washed four times with 25 mL portions of HCl solution (pH 1.3). A final adjustment of the pH to near neutral afforded the isolation of washed biomass solids by decantation. The biomass solids weighed 5.9 g and were found to contain 14.2% solids upon drying. The washed biomass solids therefore contained 0.84 g solids out of 40.7 g, or 2.1% solids after mild acid treatment as described above. When compared to the initial 6.0% solids prior to the mild acid treatment a 65% reduction in biomass solids was calculated.

To estimate the amount of the desirable component of the filtered biomass (chitin) sacrificed during the mild acid treatment an aggressive acid treatment was conducted using both pretreated and non-pretreated biomass to produce glucosamine hydrochloride in the following manner:

Dried (pretreated or non-pretreated) biomass (0.10 g) was combined with 1.90 g of 20.3% hydrochloric acid in a small test tube. The resulting solutions (19.3% HCl, 5.0% biomass solids) were held at 105° C. for 4 hours in a heat block. Dionex HPLC analysis (performed as described above) of the two acid hydrolyzed samples allowed the percent glucosamine hydrochloride by weight to be determined and compared. The non-pretreated biomass sample contained 1.0% glucosamine hydrochloride. The maximum theoretical amount of glucosamine hydrochloride attainable from the pretreated biomass is 2.9% (assuming all 65% reduction in biomass solids is non-chitin). The pretreated biomass sample was measured at 2.1% glucosamine hydrochloride by weight. Thus, mild acid pretreatment resulted in a 110% chitin-enrichment of the biomass solids, yet reduced the yield of glucosamine hydrochloride from the original biomass by 28%.

Example 6

Filtered biomass (3000 g) from a citric acid production process was combined with 3000 g of 8.7% sodium hydroxide solution. The resulting solution (4.4% NaOH, 8.1% biomass solids) was held at 90-100° C. for 45 minutes. The reaction mixture was filtered and washed with water at 40-50° C. until the percent NaOH remaining in the washed biomass solids was less than 0.06%. The washed biomass solids weighed 1479 g and were found to contain 22.9% solids upon drying. The washed biomass solids therefore contained 339 g solids out of 6000 g or 5.7% solids after mild base treatment as described above. When compared to the initial 8.1% solids prior to the mild base treatment a 30% reduction in biomass solids was calculated.

The washed biomass solids obtained from mild base treatment were subsequently subjected to a mild acid treatment. The washed biomass solids (1310 g) was combined with 3665 g of 5.5% hydrochloric acid solution and 25 g of glacial acetic acid. The resulting solution (4.0% HCl, 0.5% acetic acid, 6.0% biomass solids) was held at 90-100° C. for 3.5 hours. At this time a portion, 944 g, of the reaction mixture was filtered and washed with 1409 g water in two portions. The washed biomass solids weighed 298 g and were found to contain 12.5% solids upon drying. The washed biomass solids therefore contained 37.3 g solids out of 944 g, or 4.0% solids after mild acid treatment. When compared to the initial 6.0% solids of the mild acid treatment a 33% reduction in biomass solids was calculated. An overall reduction of 53% in biomass solids resulted from the combined effect of mild base treatment followed by mild acid treatment.

To estimate the amount of the desirable component of the filtered biomass (chitin) sacrificed during the mild base and mild acid treatments, an aggressive acid treatment was conducted using both pretreated and non-pretreated biomass to produce glucosamine hydrochloride in the following manner:

Dried (pretreated or non-pretreated) biomass (0.10 g) was combined with 1.90 g of 22.8% hydrochloric acid in a small test tube. The resulting solutions (21.6% HCl, 5.1% biomass solids) were held at 105° C. for 4 hours in a heat block. Dionex HPLC analysis (performed as described above) of the three acid hydrolyzed samples allowed the percent glucosamine hydrochloride by weight to be determined and compared. The non-pretreated biomass sample contained 0.92% glucosamine hydrochloride. The maximum theoretical amount of glucosamine hydrochloride attainable from the mild base pretreated biomass is 1.3% (assuming all 30% reduction in biomass solids is non-chitin). The mild base pretreated biomass sample was measured at 1.3% glucosamine hydrochloride by weight. Thus, mild base pretreatment resulted in a 41% chitin-enrichment of the biomass solids without a reduction in the yield of glucosamine hydrochloride from the original biomass. The maximum theoretical amount of glucosamine hydrochloride attainable from the mild acid pretreated biomass is 2.0% (assumes the overall 54% reduction in biomass solids is non-chitin). The mild acid pretreated biomass sample was measured at 1.5% glucosamine hydrochloride by weight. Thus, mild acid pretreatment following the mild base pretreatment resulted in a 63% chitin-enrichment of the original biomass solids, yet reduced the yield of glucosamine hydrochloride from the original biomass by 25%.

Example 7

A biomass sample from a citric acid fermentation process was combined with HCl to form a slurry of 13% HCl and 10.5% biomass solids. The slurry was placed in a sealed reactor and brought to 113° C. for 10 hours. Samples of the resulting composition were taken at one hour intervals and were analyzed for glucosamine. These results were then converted to a yield based on the theoretical amount of chitin in the biomass.

This procedure was repeated using slurries of 11% and 9% HCl, with biomass solids of 12%. The results are shown in Table 11.

TABLE 11

| % wt/wt HCl | Average Temperature, ° C. | Average Pressure, psig | Time in hours | % yield glucosamine based on original biomass theoretical chitin |
|---|---|---|---|---|
| 13 | 113 | 13 | 5.3 | 79 |
| 11 | 113 | 13 | 6.8 | 75 |
| 9 | 113 | 12 | 11 | 70 |

Example 8

Citric acid fermentation biomass (*A. niger*) was mixed with hydrochloric acid (JT Baker's 37 percent Reagent Grade) and placed in a sealed small scale microwave digestion bomb, available from Alltech. Prepared samples were placed in a laboratory vacuum oven with no vacuum applied. The oven was capable of maintaining a temperature of 160° C. Samples were prepared and treated under the conditions listed in Table 12 below.

Samples were diluted with nanopure water to a concentration range of within the standard range (<10 mg/L glucosamine) using a Dionex HPLC system (performing the analyses as described above). Specifically, two dilutions were performed, a 1:50 dilution followed by a 1:6 dilution. The diluted samples were filtered through a 0.45 μm filter and analyzed for glucose and glucosamine concentrations using a Dionex HPLC system.

The results are tabulated in Table 12 below. Because each trial had (at the most) four sample points, the highest glucosamine results for each trial were recorded. The sample results were not corrected for any evaporative losses in the sample during the reaction.

TABLE 12

| Acid Conc (wt. %) | Biomass Conc (wt. %) | Time (hours) | Temperature (° C.) | % glucosamine yield based on original biomass theoretical chitin |
|---|---|---|---|---|
| 2.2 | 3.9 | 4 | 160 | 18.2 |
| 2.2 | 3.9 | 4 | 160 | 10.2 |
| 2.2 | 3.9 | 2.5 | 160 | 12.6 |
| 2.2 | 3.9 | 7 | 140 | 11.6 |
| 6.2 | 5.2 | 5.5 | 140 | 17.0 |
| 6.2 | 10.1 | 5.5 | 140 | 17.9 |
| 5.7 | 5.8 | 6 | 160 | 16.3 |
| 6.2 | 10.0 | 4 | 140 | 18.4 |

*Percent glucosamine yields based on 24% theoretical chitin in dry biomass Glucosamine yields are not adjusted for evaporative losses. The evaporative loss is shown to provide an indication of a source of error in the bench top test.

The results of these embodiments of the glucosamine compositions as shown in Examples 8 and 9 indicate that using the disclosed increased temperature and or pressure methods for making the same indicate that significantly lower amounts or concentrations of hydrochloric acid are required to produce significant yields of the glucosamine compositions.

For all sample points selected for Table 12 the glucose concentrations were close to zero.

Example 9

A variety of embodiments of food supplements incorporating particular embodiments of the glucosamine compositions is shown in Table 13 below (the same basic approach could be used for the disclosed N-acetylglucosamine and/or the soluble glucans compositions and these can be added alone or in addition to glucosamine). The food supplements in these particular examples are in tablet, capsule, chewable, liquid, or food bar, form but could be in any suitable food supplement physical form.

TABLE 13

| Tablet Composition Components | % |
|---|---|
| Glucosamine HCl | 57 |
| Binder | 40 |
| Dispersant | 2 |
| Flow Enhancer | 0.7 |
| Lubricant | 0.3 |
| Juice-Based Beverage Composition Components | |
| Water | 92.93 |
| 43 High Fructose Corn Syrup | 6.0 |
| 25% Citric Acid | 0.5 |
| Fruit Punch Flavor | 0.1 |
| Glucosamine HCl | 0.312 |
| Sodium Chloride | 0.05 |
| Carboxymethyl Cellulose | 0.05 |
| 10% Red 40 | 0.035 |
| Monopotassium Phosphate | 0.025 |
| Potassium Benzoate | 0.00021 |
| Chew Composition Components | |
| 43 High Maltose Corn Syrup | 23.17 |
| 42 High Fructose Corn Syrup | 18.75 |
| Sucrose | 10.19 |
| Glucosamine HCl | 16.68 |
| Evaporated Milk | 7.39 |
| Water | 7.39 |
| Coconut oil, 92° F. Melting Point | 6.49 |
| Lecithin | 0.14 |
| Glycerol Monostearate | 0.14 |
| Salt | 0.3 |
| Chocolate-coating for bar | 9.29 |
| Flavor | 0.1 |
| Nutrition Bar Composition Components | |
| High Fructose Corn Syrup | 20 |
| Dark Chocolate Confectionery Wafers | 20 |
| Soy Protein Isolate | 15 |
| High Maltose Corn Syrup | 10 |
| Honey | 6 |
| Whey Protein Concentrate | 7 |
| Gerkens 10/12 Russet Plus Cocoa | 5 |
| Maltodextrin | 4 |
| Water | 3 |
| Canola Oil | 4 |
| Unsweetened Chocolate | 2 |
| Glycerine | 2 |

TABLE 13-continued

| | % |
|---|---|
| Fine Flake Salt | 1 |
| Glucosamine HCl | 1 |

Example 10

An Embodiment of the Process for Making N-Acetylglucosamine Using Mild Acid Pretreatment and Enzymatic Conversion to N-acetylglucosamine A 121.5 g sample of fungal biomass containing citric acid and 78.5 g water were mixed in a pressure reactor. The mixture, having 12.0% solid content and 0.6% citric acid, was heated at 150° C. under mild agitation. After 4 hours, the reaction was cooled to room temperature. The reaction mixture was filtered through a filter cloth followed by washing with water. A 63% portion of the solids in the biomass was removed in the soluble fraction. The residual solid biomass and soluble glucans in filtrates were subjected to further treatment.

The residual solid biomass was enzymatically treated to convert the chitin to N-acetylglucosamine. Specifically, 4.00 g of wet mild acid precooked biomass (equivalent to 0.8 g dry wt) were weighed into each of four 50 ml screw cap tubes. Acetate buffer of pH 4.5, pH 5.5, pH 6.5, or pH 7.5 was added to separate tubes to bring the volume of each to 25.0 ml. The pH of each tube was adjusted to match that of the starting buffer. A 6 mL aliquot of each biomass suspension was distributed into 3 separate 15 ml screw-cap tubes. Chitinase was suspended at 0.0030 g/ml in each of the 4 different pH buffers. Treatments having only chitinase received 2 ml of the appropriate pH suspension. Treatments in which chitinase was combined with cellulase received 0.5 ml of chitinase suspension and cellulase was added at 0.5 ml per treatment to those samples receiving only cellulase, and at 0.375 ml to those samples that also received chitinase. Cellulase can be obtained from Genencor International (Rochester, N.Y.)—GC880 Cellulase or from Dyadic International, Inc. (Jupiter, Fla.)—Neutral Fungal Cellulase. Tubes were incubated at 50° C. for 16 hours. Samples were analyzed for NAG and glucose content by HPLC. Treatments labeled KC contain cellulase. Treatments labeled Ch contain chitinase.

TABLE 14

| Treatment | pH | Theoretical NAG (g/l) | HPLC NAG (g/l) | Theoretical glucan(%) | Theoretical Glc (g/l) | Glc (g/l) | HPLC % NAG liberated | % Glc liberated | Undig. Solids (g/l) | Undig. Solids % |
|---|---|---|---|---|---|---|---|---|---|---|
| KC | 4.5 | 10.54 | 1.5 | 0.6244 | 17.68 | 5.983 | 14.23% | 33.84% | 18.26 | 70.9% |
| KC + Ch | 4.5 | 9.96 | 7.807 | 0.6244 | 16.72 | 6.571 | 78.35% | 39.31% | 9.53 | 39.2% |
| Ch | 4.5 | 8.56 | 6.176 | 0.6244 | 14.37 | 4.728 | 72.12% | 32.91% | 9.64 | 46.1% |
| KC | 5.5 | 10.54 | 1.038 | 0.6244 | 17.68 | 4.649 | 9.85% | 26.29% | 20.05 | 77.9% |
| KC + Ch | 5.5 | 9.96 | 10.515 | 0.6244 | 16.72 | 6.773 | 105.53% | 40.52% | 6.72 | 27.6% |
| Ch | 5.5 | 8.56 | 6.997 | 0.6244 | 14.37 | 5.47 | 81.71% | 38.08% | 8.06 | 38.5% |
| KC | 6.5 | 10.54 | 0.858 | 0.6244 | 17.68 | 3.838 | 8.14% | 21.71% | 21.05 | 81.8% |
| KC + Ch | 6.5 | 9.96 | 10.293 | 0.6244 | 16.72 | 6.712 | 103.30% | 40.15% | 6.86 | 28.2% |
| Ch | 6.5 | 8.56 | 8.595 | 0.6244 | 14.37 | 5.372 | 100.37% | 37.39% | 6.58 | 31.4% |
| KC | 7.5 | 8.56 | 0.835 | 0.6244 | 14.37 | 3.71 | 9.75% | 25.82% | 16.34 | 78.1% |
| KC + Ch | 7.5 | 9.96 | 10.048 | 0.6244 | 16.72 | 6.786 | 100.84% | 40.59% | 7.10 | 29.2% |
| Ch | 7.5 | 10.54 | 9.38 | 0.6244 | 17.68 | 5.042 | 89.00% | 28.52% | 10.96 | 42.6% |

These results demonstrate that the effective pH of the enzyme is broad, but at the same time, enzyme activity is a function of pH. As one of ordinary skill in the art can understand from these examples, under certain pH conditions, the combination of chitinase and cellulase provides substantially higher NAG concentrations as compared to either of the enzymes by themselves. With the mixed enzyme embodiments the concentration of chitinase in the mix could be decreased, while still retaining high levels of chitin degradation (i.e., NAG generation). These embodiments of the disclosed methods of making NAG are very useful where the chitinase enzyme is expensive, and the combination of helper enzyme plus reduced concentration chitinase provides a more favorable economic alternative to chitinase alone. It appears that cellulase alone was able to generate modest concentrations of NAG. This suggests that either the cellulase has limited non-specific chitinase activity, or that the microorganism used to produce the cellulase also produced some level of chitinase. Non-limiting examples of other enzymes that provide a helper function are glucanases, laminarases, amylases, glucoamylases, and others.

A sample was treated to remove the glucose by post-hydrolysis glucose oxidase treatment. This embodiment utilized a NAG/glucose suspension generated from the mild acid pretreatment treated biomass using chitinase and cellulase enzyme treatment. HPLC analysis of the sample indicated concentrations of 8.7 g/l NAG and 6.3 g/l glucose. A 50 ml aliquot of the NAG-glucose solution was pH adjusted to 5.25 with 1N $H_2SO_4$. A 10 ml aliquot was added to each of 4, 15 ml screw-cap tubes. Individual tubes were dosed with 0, 4 µl (dose A), 40 µl (dose B), and 200 µl (dose C) of Genencor OxyGO 1500 glucose oxidase. Tubes were placed in a 50° C. water bath. After 2, 4, an 8 hours, 1.0 ml of sample was removed and analyzed by HPLC for NAG, glucose, and gluconic acid content using R1 and UV detectors.

TABLE 15

| Treatment | wt % glucose 2 hr | % Conversion | wt % glucose 4 hr | % Conversion | wt % glucose 8 hr | % Conversion | wt % glucose 22 hr | % Conversion |
|---|---|---|---|---|---|---|---|---|
| Control | 100 | 0.00% | 100 | 0.00% | 100 | 0.00% | 100 | 0.00% |
| Dose A | 93.0 | 6.99% | 78.7 | 21.27% | 68.0 | 32.02% | 35.5 | 64.45% |
| Dose B | 88.2 | 11.85% | 61.5 | 38.52% | 52.2 | 47.83% | 15.1 | 84.94% |
| Dose C | 2.82 | 97.18% | 2.64 | 97.36% | 2.55 | 97.45% | 2.79 | 97.21% |

TABLE 16

| Time (h) | % Glucose Conversion Control | Dose A | Dose B | Dose C | g/l Gluconic Dose C | Control NAG (g/l) | Dose C NAG (g/l) |
|---|---|---|---|---|---|---|---|
| 0 | 0 | 0 | 0 | 0 | 0 | | |
| 2 | 0 | 6.99 | 11.85 | 98.69 | 1.743 | 9.426 | 9.225 |
| 4 | 0 | 21.27 | 38.52 | 97.36 | 2.754 | 9.401 | 9.173 |
| 8 | 0 | 32.02 | 47.83 | 97.45 | | | |
| 22 | 0 | 64.45 | 84.94 | 97.45 | 7.627 | 9.33 | 9.142 |

These data demonstrate that glucose oxidase is capable of converting over 95% of the glucose in the NAG/glucose solution to gluconic acid. The depletion of glucose is accompanied by an increase in gluconic acid concentration. NAG loss over the 22 hour reaction period is approximately 1% in both the control and Dose C treatments. Therefore, no NAG loss is attributed to glucose oxidase activity.

Next the N-acetylglucosamine is separated from salts and gluconates and other components using Purolite PCR-822 cation exchange resin. The separation was monitored by collecting fractions eluting from the column, then analyzing the fractions by HPLC.

TABLE 17

Glucose Oxidase treated broth; $N_2$ Purge of mobile phase; Purolite resin

| Based on Gluconate and NAG Only | | | Based on Gluconate, Acetate, Citrate and NAG | | |
|---|---|---|---|---|---|
| 01/09 | Mg NAG | % purity of NAG | 01/11 | Mg NAG | % purity of NAG |
| 5 | 0.094 | 8.51 | 3 | 0.037 | 5.87 |
| 6 | 0.094 | 1.56 | 4 | 0.062 | 2.02 |
| 7 | 0.273 | 2.12 | 5 | 0.747 | 6.71 |
| 8 | 2.332 | 35.88 | 6 | 3.491 | 46.98 |
| 9 | 6.847 | 82.28 | 7 | 6.659 | 86.23 |
| 10 | 8.401 | 94.70 | 8 | 6.673 | 94.29 |
| 11 | 5.698 | 91.05 | 9 | 4.254 | 92.91 |
| 12 | 2.498 | 86.67 | 10 | 1.954 | 88.96 |
| 13 | 0.865 | 74.53 | 11 | 0.754 | 83.21 |
| 14 | 0.310 | 57.67 | 12 | 0.268 | 78.23 |
| 15 | 0.144 | 32.11 | 13 | 0.113 | 74.17 |
| 16 | 0.096 | 1.64 | 14 | 0.070 | 28.03 |
| 17 | 0.094 | 0.00 | | | |
| pool 9-14 | | | pool 7-11 | | |
| pool purity | | 94.96 | pool purity | | 90.27 |
| total mg | | 24.62 | total mg | | 20.29 |
| % recovery | | 88.73 | % recovery | | 80.91 |

The portion of Table 17 on the left illustrates the degree of separation of NAG from gluconate. If fractions 9-14 are collected and the rest of the fractions discarded, 88.7% of the total NAG is recovered with nearly 95% purity. If acetate buffer is used for pH control during the enzymatic process, then some acetate impurities are incorporated into the product, as shown in the right side of the table, decreasing NAG purity to about 90% with about 81% recovery. The same or similar resins are incapable of separating NAG from glucose, as they are both neutral molecules.

Example 11

Embodiment of the Process for Simultaneously Converting Chitin to N-Acetylglucosamine and Glucose to Gluconate The biomass was treated with the mild acid pretreatment described in Example 10 (Steps A and A2 in FIG. 9). The pre-treated biomass was then enzymatically treated to produce N-acetylglucosamine and gluconate. Reactions were performed by suspending 1.0 g of pretreated biomass (0.2 g dry wt) in 50 mM acetate or citrate buffer to a volume of 6.0 ml in 15 ml screw-cap tubes. To each tube was added 2.0 ml of chitinase (0.0030 g/ml) dissolved in buffer similar to the treatments to which it was added. The tubes were incubated at 50° C. for 22 hours. Treatments 1 through 3 were treated with chitinase alone for 22 hours, after which glucose oxidase was added and the tubes were incubated for an additional 2 hours. Treatments 4 and 5 received both chitinase and glucose oxidase (160 µl of Genencor OxyGO 1500) simultaneously. Samples were analyzed at 2, 4, 7, and 22 hours for the supernatant for NAG, glucose and gluconic acid (GA) by HPLC.

TABLE 18

| | Buffer & pH | 2 hr | | 4 hr | | 7 hr | | 22 hr | | 22 hr + GO for 2 hr | |
|---|---|---|---|---|---|---|---|---|---|---|---|
| Enzyme | | NAG (g/l) | GA (g/l) | NAG (g/l) | GA (g/l) | NAG (g/l) | GA (g/l) | NAG (g/l) | GA (g/l) | NAG (g/l) | GA (g/l) |
| 1 Chitinase | OAc, 6.5 | 5.273 | 0 | 6.31 | 0 | 7.55 | 0 | 7.601 | 0 | 7.111 | 4.16 |
| 2 Chitinase | OAc, 6.0 | 5.88 | 0 | 6.45 | 0 | | | 7.996 | 0 | 7.766 | 4.4 |
| 3 Chitinase | Cit, 6.0 | 6.182 | 0 | 6.765 | 0 | 8.238 | | 8.319 | 0 | 8.113 | 4.16 |
| 4 Chitinase + GO | OAc, 6.0 | 5.765 | 2.07 | 6.255 | 3.11 | 7.543 | 4.31 | 7.624 | 4.42 | | |
| 5 Chitinase + GO | Cit, 6.0 | 5.936 | 1.76 | 5.286 | 2.24 | 8.025 | 3.97 | 8.221 | 4.11 | | |

Chitinase appeared to have slightly increased activity in pH 6.0 citrate buffer than acetate buffer. Conversely, glucose oxidase had slightly higher activity in pH 6.0 acetate buffer than in citrate buffer. In treatments 4 and 5 it was demonstrated that chitinase and glucose oxidase reactions can occur simultaneously. The amount of gluconic acid generated after 22 hours in the simultaneous reactions was the same as that obtained in Treatments 1, 2, and 3 where glucose oxidase was added independently after the chitinase reaction had occurred. Therefore, glucose oxidase treatment can be run separately or in combination with chitinase.

The resulting solution was then treated similarly to the resin separation in Example 10.

Example 12

Embodiment of the Disclosed Process for Preparing Glucosamine from N-Acetylglucosamine Produced Enzymatically The N-acetylglucosamine from Example 10 (Step B FIG. 9) was treated at 95° C. in 3% and 6% HCl for the time periods indicated in the table below to produce glucosamine hydrochloride. The data show that the 6% HCl performed slightly better than the 3% HCl under these conditions. The lower acid level can be used with either higher temperatures or longer reaction times. Under these mild conditions, very little of the glucose reacted. Acetic acid is formed by the hydrolysis.

TABLE 19

| | NAG (mmol) | | Glucose (mmol) | | Acetic (mmol) | |
|---|---|---|---|---|---|---|
| Hours | 3% HCl (weight) | 6% HCl (weight) | 3% HCl (weight) | 6% HCl (weight) | 3% HCl (weight) | 6% HCl (weight) |
| 0 | 0.55 | 0.50 | 0.54 | 0.47 | 0.21 | 0.19 |
| 1 | | 0.12 | | 0.45 | | 0.35 |
| 2 | 0.22 | 0.03 | 0.50 | 0.45 | 0.34 | 0.40 |
| 3 | 0.19 | | 0.51 | | 0.35 | |
| 4 | 0.13 | 0.00 | 0.50 | 0.47 | 0.38 | 0.45 |
| 5 | 0.09 | | 0.48 | | 0.39 | |
| 6 | 0.06 | 0.00 | 0.50 | 0.43 | 0.42 | 0.47 |

After four hours, about 90% of the NAG was converted, while 100% was converted between three and four hours. The glucose was virtually unchanged within the analytical error.

Example 13

Embodiment of the Disclosed Process Using a Mild-Acid Pretreatment Followed by Aggressive Acid Digestion to Produce Glucosamine First 120.1 g wet fungal biomass containing citric acid and 80.0 g water were mixed in a pressure reactor. The mixture was 12.7% dry solids and 0.31% citric acid and was heated at 150° C. under mild agitation. After 4 hours the reaction was cooled to room temperature. The reaction mixture was filtered through a filter cloth followed by washing with water. A portion comprising 55.2% of solid in biomass was removed.

Next 9.77 g of the wet pre-cooked biomass and 8.25 g of 37% HCl were mixed in a pressure reactor. The mixture containing 13.3% solid content and 16.9% HCl was heated at 100° C. with stirring. After 8 hours, the reaction was cooled to room temperature. The reaction mixture was filtered through a filter cloth followed by washing with water. Chromatographic data showed glucosamine yield was 38.8% based on pre-cooked biomass and the total glucosamine yield was 18.5% based on the original starting biomass material.

Example 14

One embodiment of the disclosed soluble fungal β-glucan compositions was produced utilizing 101.7 g wet fungal biomass containing citric acid and 98.3 g water mixed in a pressure reactor. The mixture having 12.0% solid content and 0.144% citric acid was heated at 150° C. under mild agitation. After 7 hours, the reaction was cooled to room temperature. The reaction mixture was filtered through a filter cloth followed by washing with water. Upon testing of the solids remaining after this step, it was determined that 46.6% of solids in the starting biomass material was hydrolyzed. The molecular weight distribution was measured by SEC (size exclusion chromatography) using a refractive index detector (RID). An RID measures the mass of comparable materials flowing through the detector cell, such as polysaccharides. An area % output indicates the percentage of the total measured polysaccharides eluting at times relative to the pullulan standards used to calibrate the instrument. Approximately 76% of the β-glucan mass had molecular weights between 1,000 and 1,000,000. The molecular weight breakdown was as follows:

TABLE 20

| 7 hr at 150 C. | | |
|---|---|---|
| High End | Low End | % Area |
| 10,084,549 | 1,000,000 | 5.339 |
| 1,000,000 | 500,000 | 0.42 |
| 500,000 | 250,000 | 0.945 |
| 250,000 | 100,000 | 3.072 |
| 100,000 | 50,000 | 4.541 |
| 50,000 | 25,000 | 7.031 |
| 25,000 | 10,000 | 8.591 |
| 10,000 | 5,000 | 13.729 |
| 5,000 | 2,500 | 18.127 |
| 2,500 | 1,000 | 20.131 |
| 1,000 | 500 | 10.459 |
| 500 | 273 | 7.615 |

Area % = percentage of the soluble β-glucans eluting in their respective molecular weight ranges compared to known standards.

Example 15

An embodiment of the disclosed soluble fungal β-glucan compositions was produced utilizing 75.6 g fungal biomass containing citric acid and 74.9 g water were mixed in a pressure reactor. The mixture having 11.9% solid content and 0.16% citric acid was heated at 150° C. under mild agitation. After 5 hours, the reaction was cooled down to room temperature. The reaction mixture was filtered through a filter cloth followed by washing with water. Upon testing of the solubility of the resulting β-glucan composition, it was determined that 40.1% of solid in the starting biomass material was hydrolyzed. The average weight molecular weight of the soluble β-glucans was 232,500.

Example 16

The fungal glucan 1 described in the purity test was prepared by heating 32 kg of fungal biomass at 12 weight % solids for 5 hr at 136° C. The citric acid concentration was 0.22 wt %. Fungal glucan 1 had an average molecular weight about 35,000.

The Fungal glucan 2 described in the purity test was prepared by heating 170 Kg of fungal biomass at 12 weight % solids for four hours at 132° C. The citric acid concentration was 0.6 wt %. Fungal glucan 2 had an average molecular weight about 450,000.

While the methods and compositions disclosed herein may be modified, specifics thereof have been shown by way of example and are described in detail. It should be understood, however, that the specific embodiments disclosed and described are not to be interpreted as limiting the claimed invention.

We claim:

1. A process comprising:
   providing a source of fungal biomass containing β-glucans, the fungal biomass not comprising yeast;
   treating the fungal biomass with water, heat from about 110° C. to about 200° C., and from about 0.01% to not more than 5% by weight organic acid, to convert at least a portion of the β-glucans into water soluble β-glucans and form a mixture including water soluble β-glucans and treated water insoluble fungal biomass; and
   recovering the water soluble β-glucans to form a water soluble β-glucan composition.

2. The process of claim 1, wherein the organic acid is selected from the group consisting of: citric acid, malic acid, maleic acid, itaconic acid, and succinic acid, and the organic acid comprises at least 0.1% by weight of the biomass, water, and acid mixture.

3. The process of claim 1, wherein the organic acid comprises citric acid.

4. The process of claim 1, further comprising purifying and/or decolorizing the water soluble β-glucan composition.

5. The process of claim 1, further comprising forming a syrup from the water soluble β-glucan composition.

6. The process of claim 1, wherein the water soluble β-glucan composition includes water soluble β-glucans having an average molecular weight of less than about 1,000,000.

7. The process of claim 3, wherein the water soluble β-glucan composition comprises β-glucans at least about 20 weight % soluble in water.

8. A process comprising:
   providing a source of fungal biomass containing β-glucans, and at least about 5% chitin, proteins, and lipids;
   treating the fungal biomass using from about 0.01% to about 5% by weight organic acid and heat from about 110° C. to about 200° C. to hydrolyze at least a portion of the β-glucans into water soluble β-glucans and form a mixture of water soluble β-glucans, water insoluble β-glucans, chitin, proteins, and lipids; and
   separating and recovering the water soluble β-glucans from the mixture to form a water soluble β-glucan composition, wherein the water soluble β-glucans in the water soluble β-glucan composition are at least about 20 weight % soluble in water.

9. The process of claim 8, wherein the separated water soluble β-glucans in the water soluble β-glucan composition have an average molecular weight of less than about 1,000,000.

10. The process of claim 8, wherein the fungal biomass is hydrolyzed using water, heat, and less than about 5% by weight of citric acid.

11. The process of claim 8, wherein the water soluble β-glucans in the water soluble β-glucan composition are at least about 30 weight % soluble in water.

12. The process of claim 8, wherein the water soluble β-glucans in the water soluble β-glucan composition include glucans having 1,3-, 1,4-, and 1,6-glycosidic linkages.

13. The process of claim 8, wherein the β-glucans in the water soluble β-glucan composition comprise soluble β-glucans having 1,4-glycosidic linkages.

14. The process of claim 8, wherein the water soluble β-glucan composition comprises at least about 50% of water soluble β-glucans having 1,3-glycosidic linkages.

15. The process of claim 8, wherein the water soluble β-glucan composition comprises at least about 70% of the water soluble β-glucans having 1,3-glycosidic linkages.

16. A method comprising:
    a) providing a source of fungal biomass having β-glucans;
    b) adding water and from about 0.01 to not more than 5% by weight citric acid, to the fungal biomass to form an about 5% to about 18% solids mixture;
    c) heating the mixture from b) to at least about 110° C. to solubilize at least a portion of the β-glucans; and
    d) separating and recovering the water soluble β-glucans from the mixture to form a water soluble β-glucan composition.

17. The method of claim 16, wherein the fungal biomass source includes at least about 0.1% by weight citric acid.

18. The method of claim 16, wherein the mixture remaining after the water soluble β-glucans are separated therefrom is treated to form glucosamine.

19. The method of claim 18, wherein the mixture remaining after the water soluble β-glucans are separated therefrom is treated to form N-acetylglucosamine.

20. The method of claim 16, wherein the composition of water soluble β-glucans is at least about 20 weight % water soluble.

21. The process of claim 16, wherein the water soluble β-glucan composition comprises water soluble glucans having 1,3-, 1,4-, and 1,6-glycosidic linkages.

22. The process of claim 16, wherein the water soluble β-glucan composition comprises water soluble glucans having at least about 50% 1,3-glycosidic linkages.

23. The process of claim 16, further comprising treating the fungal biomass to form a composition comprising at least about 70% of the water soluble glucans having 1,3-glycosidic linkages.

24. A method comprising:
    providing a source of fungal biomass containing β-glucans, chitin, proteins, lipids and from about 0.01% to 5% by weight citric acid;

adding water and not more than 5% of a second acid, to the fungal biomass to form an about 5 to about 18% solids mixture;

heating the mixture to at least about 110° C. to hydrolyze at least a portion of the β-glucans;

separating a filtrate from the mixture, the filtrate comprising a composition including water soluble β-glucans;

concentrating the composition; and precipitating the water soluble β-glucans to purify the composition, wherein the composition comprises water soluble glucans having 1,3-, 1,4-, and 1,6-glycosidic linkages.

25. The method of claim 24, wherein the fungal biomass source includes at least about 0.1% by weight citric acid.

26. The method of claim 24, wherein the mixture remaining after the water soluble β-glucans are separated therefrom is treated to form glucosamine.

27. The method of claim 24, wherein the mixture remaining after the water soluble β-glucans are separated therefrom is treated to form N-acetylglucosamine.

28. A process comprising:

providing a source of fungal biomass containing β-glucans, and at least about 5% chitin, proteins, and lipids;

treating the fungal biomass with water and about 0.01% to not more than 5% by weight organic acid at a temperature from about 110° C. to about 200° C. to convert at least a portion of the β-glucans into water soluble β-glucans and form a mixture including water soluble β-glucans and treated water insoluble fungal biomass; and recovering the water soluble β-glucans to form a water soluble β-glucan composition.

* * * * *